US011434495B2

(12) United States Patent
Tuttle et al.

(10) Patent No.: US 11,434,495 B2
(45) **Date of Patent: *Sep. 6, 2022**

(54) FORMULATION AND METHODS FOR CONTROL OF WEEDY SPECIES

(71) Applicant: Terramera, Inc., Vancouver (CA)

(72) Inventors: Chris Tuttle, Sooke (CA); Layne Woodfin, Surrey (CA)

(73) Assignee: Terramera, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,909

(22) Filed: Jan. 19, 2018

(65) Prior Publication Data

US 2018/0201945 A1 Jul. 19, 2018

Related U.S. Application Data

(63) Continuation of application No. 14/783,341, filed as application No. PCT/IB2014/060565 on Apr. 9, 2014, now Pat. No. 9,909,132.

(60) Provisional application No. 61/810,024, filed on Apr. 9, 2013.

(51) Int. Cl.
*C12N 15/82* (2006.01)
*A01N 61/00* (2006.01)

(52) U.S. Cl.
CPC ......... *C12N 15/8218* (2013.01); *A01N 61/00* (2013.01); *C12N 15/8206* (2013.01); *C12N 15/8261* (2013.01); *Y02A 40/146* (2018.01)

(58) Field of Classification Search
CPC .................................................. C12N 15/8218
USPC .......................................................... 800/286
See application file for complete search history.

(56) References Cited

U.S. PATENT DOCUMENTS

| | | | | |
|---|---|---|---|---|
| 7,148,400 | B1 | 12/2006 | Meulewaeter et al. | |
| 7,741,086 | B2 | 6/2010 | Shi et al. | |
| 9,909,132 | B2 * | 3/2018 | Tuttle | C12N 15/8206 |
| 2003/0113785 | A1 | 6/2003 | Zayed et al. | |
| 2005/0044591 | A1 * | 2/2005 | Yao | C12N 9/90 800/287 |
| 2011/0296556 | A1 | 12/2011 | Sammons et al. | |

OTHER PUBLICATIONS

Thomas et al. The Plant Journal 25(4):417-425 (Year: 2001).*

* cited by examiner

*Primary Examiner* — Li Zheng
(74) *Attorney, Agent, or Firm* — Oyen Wiggs Green & Mutala LLP

(57) ABSTRACT

A formulation is provided for application to a host plant to reduce, inhibit or impair one or more of growth and development of the host plant. A method of inhibiting growth plant growth and development is also provided as a means of controlling weedy species. The method comprises: selecting a suitable gene for growth suppression in a target plant; identifying an at least one target site accessible to base pairing in the suitable gene; identifying an at least one divergent site in the at least one target site; designing a construct complementary to the at least one divergent site; adding an at least one RNAi inducer to the construct; and delivering the construct to the target plant.

21 Claims, 11 Drawing Sheets

Specification includes a Sequence Listing.

SEQUENCE LISTING

<160> NUMBER OF SEQ ID NOS: 71

<210> SEQ ID NO 1
<211> LENGTH: 21
<212> TYPE: RNA
<213> ORGANISM: Artificial Sequence
<220> FEATURE:
<223> OTHER INFORMATION: Actin 2 si-RNA-A strand 1

<400> SEQUENCE: 1
uuguagaaag ugugaugccu u 21

<210> SEQ ID NO 2
<211> LENGTH: 21
<212> TYPE: RNA
<213> ORGANISM: Artificial Sequence
<220> FEATURE:
<223> OTHER INFORMATION: Actin 2 si-RNA-B strand 1

<400> SEQUENCE: 2
uaauucauag uucuucucgu u 21

<210> SEQ ID NO 3
<211> LENGTH: 21
<212> TYPE: RNA
<213> ORGANISM: Artificial Sequence
<220> FEATURE:
<223> OTHER INFORMATION: CHI1 siRNA-A strand 1

<400> SEQUENCE: 3
uuccaguucc ucuaucuccu u 21

<210> SEQ ID NO 4
<211> LENGTH: 21
<212> TYPE: RNA
<213> ORGANISM: Artificial Sequence
<220> FEATURE:
<223> OTHER INFORMATION: CHI1 siRNA-B Strand 1

<400> SEQUENCE: 4
uugcagaaga agauguuccu u 21

<210> SEQ ID NO 5
<211> LENGTH: 21
<212> TYPE: RNA
<213> ORGANISM: Artificial Sequence
<220> FEATURE:
<223> OTHER INFORMATION: 18S siRNA-A Strand 1

<400> SEQUENCE: 5
uuuauuguca cuaccucccu u 21

<210> SEQ ID NO 6
<211> LENGTH: 21
<212> TYPE: RNA
<213> ORGANISM: Artificial Sequence
<220> FEATURE:
<223> OTHER INFORMATION: 18S siRNA-B Strand1

<400> SEQUENCE: 6
uuaucuaaua aaugcguccu u 21

<210> SEQ ID NO 7
<211> LENGTH: 23
<212> TYPE: DNA
<213> ORGANISM: Artificial Sequence
<220> FEATURE:
<223> OTHER INFORMATION: Actin 2 DNA encoding siRNA-A strand 1

<400> SEQUENCE: 7
aattgtagaa agtgtgatgc ctt 23

<210> SEQ ID NO 8
<211> LENGTH: 23
<212> TYPE: DNA
<213> ORGANISM: Artificial Sequence
<220> FEATURE:
<223> OTHER INFORMATION: Actin 2 DNA encoding siRNA-B strand 1

<400> SEQUENCE: 8
aataattcat agttcttctc gtt 23

<210> SEQ ID NO 9
<211> LENGTH: 23
<212> TYPE: DNA
<213> ORGANISM: Artificial Sequence
<220> FEATURE:
<223> OTHER INFORMATION: CHI1 DNA encoding siRNA-A strand 1

<400> SEQUENCE: 9
aattccagtt cctctatctc ctt 23

<210> SEQ ID NO 10
<211> LENGTH: 23
<212> TYPE: DNA
<213> ORGANISM: Artificial Sequence
<220> FEATURE:
<223> OTHER INFORMATION: CHI1 DNA encoding siRNA-b strand 1

<400> SEQUENCE: 10
aattgcagaa gaagatgttc ctt 23

<210> SEQ ID NO 11
<211> LENGTH: 23
<212> TYPE: DNA
<213> ORGANISM: Artificial Sequence
<220> FEATURE:
<223> OTHER INFORMATION: 18S DNA encoding siRNA-A strand 1

<400> SEQUENCE: 11
aatttattgt cactacctcc ctt 23

<210> SEQ ID NO 12
<211> LENGTH: 23
<212> TYPE: DNA
<213> ORGANISM: Artificial Sequence
<220> FEATURE:
<223> OTHER INFORMATION: 18S DNA encoding siRNA-b strand 1

<400> SEQUENCE: 12
aattatctaa taaatgcgtc ctt 23

<210> SEQ ID NO 13
<211> LENGTH: 492
<212> TYPE: DNA
<213> ORGANISM: Artificial Sequence
<220> FEATURE:
<223> OTHER INFORMATION: Synthetic construct targeting CHLI1 in A. thaliana, B. rapa, M. truncatula, Z. mays, N. tobacum

<400> SEQUENCE: 13
attccaacca gaagcagctg aatccaaaag aacatcaacc aaatgatcat ccaagagatt 60

-continued

```
aacttcatca acataaagaa tccctctatt agctttagcc tcgtaactca gcatccctaa    120

ccgtccctac ttgcgcgtgg ccctgaggtt aaagagagtg tgtgaatgga agggttggaa    180

gaaggagaag aaaggtaacg tgaaggaaga aatgcaatgg aagaaggata aactggcctc    240

gcactcttct ttgaatcaaa cttccctaca gttgtagatt ttccagttcc tctatctccc    300

ataatcataa aaacgagctc tttcctcaac tatcttcact ctcagctctg catctctcac    360

ggtccccact tagtgaagcc attttgttta gaatttttca gtgaagaaga agaagaagaa    420

ttttggggca aatgggggag gaggaaggtt ttgaggaagg agaagagagt gaaggagaag    480

cccagattgc ag                                                          492

<210> SEQ ID NO 14
<211> LENGTH: 818
<212> TYPE: DNA
<213> ORGANISM: Artificial Sequence
<220> FEATURE:
<223> OTHER INFORMATION: Synthetic construct targeting mGFP5er, Acdl1,
      Acd2, Cat1, Cat2 and Lsdl in B. rapa pekinensis

<400> SEQUENCE: 14

gtgcaactcg ctgatcatta tcaacaaaat actccaattg gcgatggccc cgcagagagg     60

ccgcttcgta aaatctcaac tgctttcaaa gaactagcag ccaccgtgag ctcgccgagt    120

cctgaagtct ccgtggctca gttctctcac gcttgctctc tcgtctcgcc tctctttggt    180

tgcctcggga tcgccttcaa gatattgagg caaactgtgt aaggaaagct ggtagtcata    240

ctagaaacct tttgagggta gagctaatgg ttgatctcat gtcgacgctg gaggatcgcc    300

tccactctca aagagagtgg tgggagaaga agagaaactg gagctggaaa gaagagataa    360

aagcttcaga aggaagagca tcaccaccaa ctctggtgct cctgtatgga acaacaactc    420

ctccatgacc gttggaccca gaggtcccca cgcgcttaaa ccaaacccta aatctcacat    480

tcaagaaaac tgaacctcac ttgtgctgac ttcctcagag ctccaggtgt tcaaactccg    540

gtcattcctg tccgctgcgc cgagaaagtt cctatcccta ccaaatccta cactggaata    600

agaacaaatg tatcctagag gagcaaccaa tgtgcgttgt gcgttatgtc acattgtcaa    660

catggttcct cttcatccta cccttacggt gcatcatctg ttaaatgcgc tgtttgccag    720

tttgttacta acgttaacaa aacttaccct taaatttatt tgcactactg gaaaactacc    780

tgttccatgg ccaacacttg tcactacttt ctcttatg                            818

<210> SEQ ID NO 15
<211> LENGTH: 742
<212> TYPE: DNA
<213> ORGANISM: Artificial Sequence
<220> FEATURE:
<223> OTHER INFORMATION: Synthetic construct targetingAtg5, Cat1, Jazh,
      MC2, Beclin1 in Nicotiana sylvestris

<400> SEQUENCE: 15

tctgaccagg tctcatcgtg tcgacggagg aagtgaagca cagaaatgga acaaaaataa     60

aaccttgggg tactctttga tcttctttgc aagaatgtaa tgaatatccc tgattacttt    120

cttcatatac cgtccgtcaa gtgccttcaa ttgctgaagc caaatcctaa atcccatacc    180

acaagattac aggcatagag tctcgaagca ttattaataa ctcattggcg atcaaattaa    240

gatgaatgtc agtttattaa aggaaaaagt aaagaacaag aacaaaatca tttggcactt    300

ttcatactac aaccatcgac aaaattagct gctgccactg cttctttgac atgtaatacg    360
```

-continued

```
ggagactcac tgctatttca ttatttggct caaggcaaag gaattaggag atgaagtgga    420

tggatatgat gaaagctcct ccgccaccac ctaatcaata caatagcagc agtagtacta    480

ataaccttag ccaaagcaaa gaaatcagag aagaagaaga gcgaaaaagc ttgccttctt    540

ctccatacaa tccggccaaa gtttcaatat ccggatcatg gacaccaata acaatactta    600

taggatcact atacagcaaa cgagatgcaa ttttagctaa gacagaagtt tcacaagctc    660

atttagagct gttaaagaag actaatgaag cagcaataga agaaacagag aagcaatctc    720

gagctcctga gacctggtcc tc                                             742


<210> SEQ ID NO 16
<211> LENGTH: 749
<212> TYPE: DNA
<213> ORGANISM: Artificial Sequence
<220> FEATURE:
<223> OTHER INFORMATION: Synthetic construct targeting Acd2, Bl-l, Llsl,
      NtTCTP, Beclinl in Nicotiana sylvestris

<400> SEQUENCE: 16

tctgaccagg tctcatcgtg tcgacatggt tgaacttata tcgactgtgg aggaaacaca     60

attagacgaa cagagacaat tgacagagga tgaaagttgg caaagaggga taaaataatt    120

aagaataaga caattgagat agaatggagt cttgcacatc gttcttcaat ttggagttac    180

gattctctta agaacttccg ccagatctct ccctttgttc aaactcatct caaaaatctg    240

gtatctctat ccttttgctc aatttcatca cattacccaa tggcttcttc tctattatac    300

tccaccacca actcctcaaa ttctttcact tttcattctt ctctccctac taaaacccaa    360

tttgggtgct gatgaagatg aaggtggaga agcccaagaa gcatttaaaa agaacattga    420

atcagcaact aagttcctca tagtacttcc tgaactgttt cttaatgtta taagcagcag    480

tagtactaat aaccttagcc aaagcaaaga aatcagagaa gaagaagagc gaaaaagctt    540

gccttcttct ccatacaatc cggccaaagt ttcaatatcc ggatcatgga caccaataac    600

aatacttata ggatcactat acagcaaact gtctgataaa cttgataagg acatacaagc    660

ctacgaagga gaaattgaag atagaacgga acgattaaca actttgccga ctttgcaaat    720

tcaactcgag ctcctgagac ctggtcctc                                      749


<210> SEQ ID NO 17
<211> LENGTH: 7883
<212> TYPE: DNA
<213> ORGANISM: Artificial Sequence
<220> FEATURE:
<223> OTHER INFORMATION: Synthetic construct consisting of CaMV35s
      promoter, TRV Ppk20 RNAI, ribozyme sequence and NOS terminator
<220> FEATURE:
<221> NAME/KEY: misc_feature
<222> LOCATION: (7256)..(7256)
<223> OTHER INFORMATION: n is a, c, g or t

<400> SEQUENCE: 17

aagcttgcat gcctgcaggt caacatggtg gagcacgaca ctctcgtcta ctccaagaat     60

atcaaagata cagtctcaga agaccagagg gctattgaga cttttcaaca aagggtaata    120

tcgggaaacc tcctcggatt ccattgccca gctatctgtc acttcatcga aaggacagta    180

gaaaaggaag atggcttcta caaatgccat cattgcgata aaggaaaggc tatcgttcaa    240

gatgcctcta ccgacagtgg tcccaaagat ggacccccac ccacgaggaa catcgtggaa    300

aaagaagacg ttccaaccac gtcttcaaag caagtggatt gatgtgatgg tcaacatggt    360

ggagcacgac actctcgtct actccaagaa tatcaaagat acagtctcag aagaccagag    420
```

-continued

```
ggctattgag acttttcaac aaagggtaat atcgggaaac ctcctcggat tccattgccc    480
agctatctgt cacttcatcg aaaggacagt agaaaaggaa gatggcttct acaaatgcca    540
tcattgcgat aaaggaaagg ctatcgttca agatgcctct accgacagtg gtcccaaaga    600
tggaccccca cccacgagga acatcgtgga aaaagaagac gttccaacca cgtcttcaaa    660
gcaagtggat tgatgtgata tctccactga cgtaagggat gacgcacaat cccactatcc    720
ttcgcaagac ccttcctcta tataaggaag ttcatttcat ttggagagga taaaacattt    780
caatcctttg aacgcggtag aacgtgctaa ttggattttg gtgagaacgc ggtagaacgt    840
acttatcacc tacagtttta ttttgttttt ctttttggtt taatctatcc agcttagtac    900
cgagtggggg aaagtgactg gtgtgcctaa aacctttttct ttgatacttt gtaaaaatac    960
atacagatac aatggcgaac ggtaacttca agttgtctca attgctcaat gtggacgaga   1020
tgtctgctga gcagaggagt catttctttg acttgatgct gactaaacct gattgtgaga   1080
tcgggcaaat gatgcaaaga gttgttgttg ataaagtcga tgacatgatt agagaaagaa   1140
agactaaaga tccagtgatt gttcatgaag ttctttctca gaaggaacag aacaagttga   1200
tggaaattta tcctgaattc aatatcgtgt ttaaagacga caaaaacatg gttcatgggt   1260
ttgcggctgc tgagcgaaaa ctacaagctt tattgctttt agatagagtt cctgctctgc   1320
aagaggtgga tgacatcggt ggtcaatggt cgttttgggt aactagaggt gagaaaagga   1380
ttcattcctg ttgtccaaat ctagatattc gggatgatca gagagaaatt tctcgacaga   1440
tatttcttac tgctattggt gatcaagcta gaagtggtaa gagacagatg tcggagaatg   1500
agctgtggat gtatgaccaa tttcgtgaaa atattgctgc gcctaacgcg gttaggtgca   1560
ataatacata tcagggttgt acatgtaggg gtttttctga tggtaagaag aaaggcgcgc   1620
agtatgcgat agctcttcac agcctgtatg acttcaagtt gaaagacttg atggctacta   1680
tggttgagaa gaaaactaaa gtggttcatg ctgctatgct ttttgctcct gaaagtatgt   1740
tagtggacga aggtccatta ccttctgttg acggttacta catgaagaag aacgggaaga   1800
tctatttcgg ttttgagaaa gatccttcct tttcttacat tcatgactgg gaagagtaca   1860
agaagtatct actggggaag ccagtgagtt accaagggaa tgtgttctac ttcgaaccgt   1920
ggcaggtgag aggagacaca atgctttttt cgatctacag gatagctgga gttccgagga   1980
ggtctctatc atcgcaagag tactaccgaa gaatatatat cagtagatgg gaaaacatgg   2040
ttgttgtccc aattttcgat ctggtcgaat caacgcgaga gttggtcaag aaagacctgt   2100
ttgtagagaa acaattcatg gacaagtgtt tggattacat agctaggtta tctgaccagc   2160
agctgaccat aagcaatgtt aaatcatact tgagttcaaa taattgggtc ttattcataa   2220
acggggcggc cgtgaagaac aagcaaagtg tagattctcg agatttacag ttgttggctc   2280
aaactttgct agtgaaggaa caagtggcga gacctgtcat gagggagttg cgtgaagcaa   2340
ttctgactga gacgaaacct atcacgtcat tgactgatgt gctgggttta atatcaagaa   2400
aactgtggaa gcagtttgct aacaagatcg cagtcggcgg attcgttggc atggttggta   2460
ctctaattgg attctatcca aagaaggtac taacctgggc gaaggacaca ccaaatggtc   2520
cagaactatg ttacgagaac tcgcacaaaa ccaaggtgat agtatttctg agtgttgtgt   2580
atgccattgg aggaatcacg cttatgcgtc gagacatccg agatggactg gtgaaaaaac   2640
tatgtgatat gtttgatatc aaacgggggg cccatgtctt agacgttgag aatccgtgcc   2700
gctattatga aatcaacgat ttctttagca gtctgtattc ggcatctgag tccggtgaga   2760
```

-continued

```
ccgttttacc agatttatcc gaggtaaaag ccaagtctga taagctattg cagcagaaga   2820
aagaaatcgc tgacgagttt ctaagtgcaa aattctctaa ctattctggc agttcggtga   2880
gaacttctcc accatcggtg gtcggttcat ctcgaagcgg actgggtctg ttgttggaag   2940
acagtaacgt gctgacccaa gctagagttg gagtttcaag aaaggtagac gatgaggaga   3000
tcatggagca gtttctgagt ggtcttattg acactgaagc agaaattgac gaggttgttc   3060
cagcctttte agctgaatgt gaaagagggg aaacaagcgg tacaaaggtg ttgtgtaaac   3120
ctttaacgcc accaggattt gagaacgtgt tgccagctgt caaacctttg gtcagcaaag   3180
gaaaaacggt caaacgtgtc gattacttcc aagtgatggg aggtgagaga ttaccaaaaa   3240
ggccggttgt cagtggagac gattctgtgg acgctagaag agagtttctg tactacttag   3300
atgcggagag agtcgctcaa aatgatgaaa ttatgtctct gtatcgtgac tattcgagag   3360
gagttattcg aactggaggt cagaattacc cgcacggact gggagtgtgg gatgtggaga   3420
tgaagaactg gtgcatacgt ccagtggtca ctgaacatgc ttatgtgttc caaccagaca   3480
aacgtatgga tgattggtcg ggatacttag aagtggctgt ttgggaacga ggtatgttgg   3540
tcaacgactt cgcggtcgaa aggatgagtg attatgtcat agtttgcgat cagacgtatc   3600
tttgcaataa caggttgatc ttggacaatt taagtgccct ggatctagga ccagttaact   3660
gttcttttga attagttgac ggtgtacctg gttgtggtaa gtcgacaatg attgtcaact   3720
cagctaatcc ttgtgtcgat gtggttctct ctactgggag agcagcaacc gacgacttga   3780
tcgagagatt cgcgagcaaa ggttttccat gcaaattgaa aaggagagtg aagacggttg   3840
attctttttt gatgcattgt gttgatggtt ctttaaccgg agacgtgttg catttcgatg   3900
aagctctcat ggcccatgct ggtatggtgt acttttgcgc tcagatagct ggtgctaaac   3960
gatgtatctg tcaaggagat cagaatcaaa tttctttcaa gcctagggta tctcaagttg   4020
atttgaggtt ttctagtctg gtcggaaagt ttgacattgt tacagaaaaa agagaaactt   4080
acagaagtcc agcagatgtg gctgccgtat tgaacaagta ctatactgga gatgtcagaa   4140
cacataacgc gactgctaat tcgatgacgg tgaggaagat tgtgtctaaa gaacaggttt   4200
ctttgaagcc tggtgctcag tacataactt tccttcagtc tgagaagaag gagttggtaa   4260
atttgttggc attgaggaaa gtggcagcta aagtgagtac agtacacgag tcgcaaggag   4320
agacattcaa agatgtagtc ctagtcagga cgaaacctac ggatgactca atcgctagag   4380
gtcgggagta cttaatcgtg gcgttgtcgc gtcacacaca atcacttgtg tatgaaactg   4440
tgaaagagga cgatgtaagc aaagagatca gggaaagtgc cgcgcttacg aaggcggctt   4500
tggcaagatt ttttgttact gagaccgtct tatgacggtt tcggtctagg tttgatgtct   4560
ttagacatca tgaagggcct tgcgccgttc cagattcagg tacgattacg gacttggaga   4620
tgtggtacga cgctttgttt ccgggaaatt cgttaagaga ctcaagccta gacgggtatt   4680
tggtggcaac gactgattgc aatttgcgat tagacaatgt tacgatcaaa agtggaaact   4740
ggaaagacaa gtttgctgaa aaagaaacgt ttctgaaacc ggttattcgt actgctatgc   4800
ctgacaaaag gaagactact cagttggaga gtttgttagc attgcagaaa aggaaccaag   4860
cggcacccga tctacaagaa aatgtgcacg caacagttct aatcgaagag acgatgaaga   4920
agttgaaatc tgttgtctac gatgtgggaa aaattcgggc tgatcctatt gtcaatagag   4980
ctcaaatgga gagatggtgg agaaatcaaa gcacagcggt acaggctaag gtagtagcag   5040
atgtgagaga gttacatgaa atagactatt cgtcttacat gtatatgatc aaatctgacg   5100
tgaaacctaa gactgattta acaccgcaat ttgaatactc agctctacag actgttgtgt   5160
```

-continued atcacgagaa gttgatcaac tcgttgttcg gtccaatttt caaagaaatt aatgaacgca 5220
agttggatgc tatgcaacca cattttgtgt tcaacacgag aatgacatcg agtgatttaa 5280
acgatcgagt gaagttctta aatacggaag cggcttacga ctttgttgag atagacatgt 5340
ctaaattcga caagtcggca aatcgcttcc atttacaact gcagctggag atttacaggt 5400
tatttgggct agatgagtgg gcggccttcc tttgggaggt gtcgcacact caaactactg 5460
tgagagatat tcaaaatggt atgatggcgc atatttggta ccaacaaaag agtggagatg 5520
ctgatactta taatgcaaat tcagatagaa cactgtgtgc actcttgtct gaattaccat 5580
tggagaaagc agtcatggtt acatatggag gagatgactc actgattgcg tttcctagag 5640
gaacgcagtt tgttgatccg tgtccaaagt tggctactaa gtggaatttc gagtgcaaga 5700
tttttaagta cgatgtccca atgttttgtg ggaagttctt gcttaagacg tcatcgtgtt 5760
acgagttcgt gccagatccg gtaaaagttc tgacgaagtt ggggaaaaag agtataaagg 5820
atgtgcaaca tttagccgag atctacatct cgctgaatga ttccaataga gctcttggga 5880
actacatggt ggtatccaaa ctgtccgagt ctgtttcaga ccggtatttg tacaaaggtg 5940
attctgttca tgcgctttgt gcgctatgga agcatattaa gagttttaca gctctgtgta 6000
cattattccg agacgaaaac gataaggaat tgaacccggc taaggttgat tggaagaagg 6060
cacagagagc tgtgtcaaac ttttacgact ggtaatatgg aagacaagtc attggtcacc 6120
ttgaagaaga agactttcga agtctcaaaa ttctcaaatc taggggccat tgaattgttt 6180
gtggacggta ggaggaagag accgaagtat tttcacagaa gaagagaaac tgtcctaaat 6240
catgttggtg ggaagaagag tgaacacaag ttagacgttt ttgaccaaag ggattacaaa 6300
atgattaaat cttacgcgtt tctaaagata gtaggtgtac aactagttgt aacatcacat 6360
ctacctgcag atacgcctgg gttcattcaa atcgatctgt tggattcgag acttactgag 6420
aaaagaaaga gaggaaagac tattcagaga ttcaaagctc gagcttgcga taactgttca 6480
gttgcgcagt acaaggttga atacagtatt tccacacagg agaacgtact tgatgtctgg 6540
aaggtgggtt gtatttctga gggcgttccg gtctgtgacg gtacataccc tttcagtatc 6600
gaagtgtcgc taatatgggt tgctactgat tcgactaggc gcctcaatgt ggaagaactg 6660
aacagttcgg attacattga aggcgatttt accgatcaag aggttttcgg tgagttcatg 6720
tctttgaaac aagtggagat gaagacgatt gaggcgaagt acgatggtcc ttacagacca 6780
gctactacta gacctaagtc attattgtca agtgaagatg ttaagagagc gtctaataag 6840
aaaaactcgt cttaatgcat aaagaaattt attgtcaata tgacgtgtgt actcaagggt 6900
tgtgtgaatg aagtcactgt tcttggtcac gagacgtgta gtatcggtca tgctaacaaa 6960
ttgcgaaagc aagttgctga catggttggt gtcacacgta ggtgtgcgga aaataattgt 7020
ggatggtttg tctgtgttgt tatcaatgat tttacttttg atgtgtataa ttgttgtggc 7080
cgtagtcacc ttgaaaagtg tcgtaaacgt gttgaaacaa gaaatcgaga aatttggaaa 7140
caaattcgac gaaatcaagc tgaaaacatg tctgcgacag ctaaaaagtc tcataattcg 7200
aagacctcta agaagaaatt caaagaggac agagaatttg ggacaccaaa aagatnttaa 7260
gagatgatgt tcctttcggg attgatcgtt tgtttgcttt ttgattttat tttatattgt 7320
tatctgtttc tgtgtataga ctgtttgaga ttggcgcttg gccgactcat tgtcttacca 7380
taggggaacg gactttgttt gtgttgttat tttatttgta ttttattaaa attctcaatg 7440
atctgaaaag gcctcgaggc taagagatta ttgggggtg agtaagtact tttaaagtga 7500

-continued tgatggttac aaaggcaaaa ggggtaaaac ccctcgccta cgtaagcgtt attacgcccg 7560
tctgtactta tatcagtaca ctgacgagtc cctaaaggac gaaacgggcc cctcgaattt 7620
ccccgatggg cgttcaaaca tttggcaata aagtttctta agattgaatc ctgttgccgg 7680
tcttgcgatg attatcatat aatttctgtt gaattacgtt aagcatgtaa taattaacat 7740
gtaatgcatg acgttattta tgagatgggt ttttatgatt agagtcccgc aattatacat 7800
ttaatacgcg atagaaaaca aaatatagcg cgcaaactag gataaattat cgcgcgcggt 7860
gtcatctatg ttactagatc ggg 7883

<210> SEQ ID NO 18
<211> LENGTH: 9663
<212> TYPE: DNA
<213> ORGANISM: Artificial Sequence
<220> FEATURE:
<223> OTHER INFORMATION: TRV RNA2-MCS for transcription in plant cells

<400> SEQUENCE: 18
ataaaacatt gcacctatgg tgttgccctg gctggggtat gtcagtgatc gcagtagaat 60
gtactaattg acaagttgga gaatacggta gaacgtcctt atccaacaca gcctttatcc 120
ctctccctga cgaggttttt gtcagtgtaa tatttctttt tgaactatcc agcttagtac 180
cgtacgggaa agtgactggt gtgcttatct ttgaaatgtt actttgggtt tcggttcttt 240
aggttagtaa gaaagcactt gtcttctcat acaaaggaaa acctgagacg tatcgcttac 300
gaaagtagca atgaaagaaa ggtggtggtt ttaatcgcra ccgcaaaaac gatggggtcg 360
ttttaattaa cttctcctac gcaagcgtct aaacggacgt tggggttttg ctagtttctt 420
tagagaaaac tagctaagtc tttaatgtta tcattagaga tggcataaat ataatacttg 480
tgtctgctga taagatcatt ttaatttgga cgattagact tgttgaacta caggttactg 540
aatcacttgc gctaatcaac atgggagata tgtacgatga atcatttgac aagtcgggcg 600
gtcctgctga cttgatggac gattcttggg tggaatcagt ttcgtggaaa gatctgttga 660
agaagttaca cagcataaaa tttgcactac agtctggtag agatgagatc actgggttac 720
tagcggcact gaatagacag tgtccttatt caccatatga gcagtttcca gataagaagg 780
tgtatttcct tttagactca cgggctaaca gtgctcttgg tgtgattcag aacgcttcag 840
cgttcaagag acgagctgat gagaagaatg cagtggcggg tgttacaaat attcctgcga 900
atccaaacac aacggttacg acgaaccaag ggagtactac tactaccaag gcgaacactg 960
gctcgacttt ggaagaagac ttgtacactt attacaaatt cgatgatgcc tctacagctt 1020
tccacaaatc tctaacttcg ttagagaaca tggagttgaa gagttattac cgaaggaact 1080
ttgagaaagt attcgggatt aagtttggtg gagcagctgc tagttcatct gcaccgcctc 1140
cagcgagtgg aggtccgata cgtcctaatc cctagggatt taaggacgtg aactctgttg 1200
agatctctgt gaaattcaga gggtgggtga taccatattc actgatgcca ttagcgacat 1260
ctaaataggg ctaattgtga ctaatttgag ggaatttcct ttaccattga cgtcagtgtc 1320
gttggtagca tttgagtttc gcaatgcacg aattacttag gaagtggctt gacgacacta 1380
atgtgttatt gttagataat ggtttggtgg tcaaggtacg tagtagagtc ccacatattc 1440
gcacgtatga agtaattgga aagttgtcag tttttgataa ttcactggga gatgatacgc 1500
tgtttgaggg aaaagtagag aacgtatttg tttttatgtt caggcggttc ttgtgtgtca 1560
acaaagatgg acattgttac tcaaggaagc acgatgagct ttattattac ggacgagtgg 1620
acttagattc tgtgagtaag gttaccgaat tctctagaag gcctccatgg ggatccggta 1680

-continued

```
ccgagctcac gcgtctcgag gcccgggcat gtcccgaaga cattaaacta cggttcttta   1740
agtagatccg tgtctgaagt tttaggttca atttaaacct acgagattga cattctcgac   1800
tgatcttgat tgatcggtaa gtcttttgta atttaatttt ctttttgatt ttattttaaa   1860
ttgttatctg tttctgtgta tagactgttt gagatcggcg tttggccgac tcattgtctt   1920
accatagggg aacggacttt gtttgtgttg ttattttatt tgtattttat taaaattctc   1980
aacgatctga aaaagcctcg cggctaagag attgttgggg ggtgagtaag tacttttaaa   2040
gtgatgatgg ttacaaaggc aaaaggggta aaacccctcg cctacgtaag cgttattacg   2100
cccgtctgta cttatatcag tacactgacg agtccctaaa ggacgaaacg ggagaacgct   2160
agccaccacc accaccacca cgtgtgaatt acaggtgacc agctcgaatt tccccgatcg   2220
ttcaaacatt tggcaataaa gtttcttaag attgaatcct gttgccggtc ttgcgatgat   2280
tatcatataa tttctgttga attacgttaa gcatgtaata attaacatgt aatgcatgac   2340
gttatttatg agatgggttt ttatgattag agtcccgcaa ttatacattt aatacgcgat   2400
agaaaacaaa atatagcgcg caaactagga taaattatcg cgcgcggtgt catctatgtt   2460
actagatcgg gaattaaact atcagtgttt gacaggatat attggcgggt aaacctaaga   2520
gaaaagagcg tttattagaa taacggatat ttaaaagggc gtgaaaaggt ttatccgttc   2580
gtccatttgt atgtgcatgc caaccacagg gttcccctcg ggatcaaagt actttgatcc   2640
aacccctccg ctgctatagt gcagtcggct tctgacgttc agtgcagccg tcttctgaaa   2700
acgacatgtc gcacaagtcc taagttacgc gacaggctgc cgccctgccc ttttcctggc   2760
gttttcttgt cgcgtgtttt agtcgcataa agtagaatac ttgcgactag aaccggagac   2820
attacgccat gaacaagagc gccgccgctg gcctgctggg ctatgcccgc gtcagcaccg   2880
acgaccagga cttgaccaac caacgggccg aactgcacgc ggccggctgc accaagctgt   2940
tttccgagaa gatcaccggc accaggcgcg accgcccgga gctggccagg atgcttgacc   3000
acctacgccc tggcgacgtt gtgacagtga ccaggctaga ccgcctggcc cgcagcaccc   3060
gcgacctact ggacattgcc gagcgcatcc aggaggccgg cgcgggcctg cgtagcctgg   3120
cagagccgtg ggccgacacc accacgccgg ccggccgcat ggtgttgacc gtgttcgccg   3180
gcattgccga gttcgagcgt tccctaatca tcgaccgcac ccggagcggg cgcgaggccg   3240
ccaaggcccg aggcgtgaag tttggccccc gccctaccct caccccggca cagatcgcgc   3300
acgcccgcga gctgatcgac caggaaggcc gcaccgtgaa agaggcggct gcactgcttg   3360
gcgtgcatcg ctcgaccctg taccgcgcac ttgagcgcag cgaggaagtg acgcccaccg   3420
aggccaggcg gcgcggtgcc ttccgtgagg acgcattgac cgaggccgac gccctggcgg   3480
ccgccgagaa tgaacgccaa gaggaacaag catgaaaccg caccaggacg gccaggacga   3540
accgtttttc attaccgaag agatcgaggc ggagatgatc gcggccgggt acgtgttcga   3600
gccgcccgcg cacgtctcaa ccgtgcggct gcatgaaatc ctggccggtt tgtctgatgc   3660
caagctggcg gcctggccgg ccagcttggc cgctgaagaa accgagcgcc gccgtctaaa   3720
aaggtgatgt gtatttgagt aaaacagctt gcgtcatgcg gtcgctgcgt atatgatgcg   3780
atgagtaaat aaacaaatac gcaaggggaa cgcatgaagg ttatcgctgt acttaaccag   3840
aaaggcgggt caggcaagac gaccatcgca acccatctag cccgcgccct gcaactcgcc   3900
ggggccgatg ttctgttagt cgattccgat ccccagggca gtgcccgcga ttgggcggcc   3960
gtgcgggaag atcaaccgct aaccgttgtc ggcatcgacc gcccgacgat tgaccgcgac   4020
```

-continued

```
gtgaaggcca tcggccggcg cgacttcgta gtgatcgacg gagcgcccca ggcggcggac   4080
ttggctgtgt ccgcgatcaa ggcagccgac ttcgtgctga ttccggtgca gccaagccct   4140
tacgacatat gggccaccgc cgacctggtg gagctggtta agcagcgcat tgaggtcacg   4200
gatggaaggc tacaagcggc ctttgtcgtg tcgcgggcga tcaaaggcac gcgcatcggc   4260
ggtgaggttg ccgaggcgct ggccgggtac gagctgccca ttcttgagtc ccgtatcacg   4320
cagcgcgtga gctacccagg cactgccgcc gccggcacaa ccgttcttga atcagaaccc   4380
gagggcgacg ctgcccgcga ggtccaggcg ctggccgctg aaattaaatc aaaactcatt   4440
tgagttaatg aggtaaagag aaaatgagca aaagcacaaa cacgctaagt gccggccgtc   4500
cgagcgcacg cagcagcaag gctgcaacgt tggccagcct ggcagacacg ccagccatga   4560
agcgggtcaa ctttcagttg ccggcggagg atcacaccaa gctgaagatg tacgcggtac   4620
gccaaggcaa gaccattacc gagctgctat ctgaatacat cgcgcagcta ccagagtaaa   4680
tgagcaaatg aataaatgag tagatgaatt ttagcggcta aaggaggcgg catggaaaat   4740
caagaacaac caggcaccga cgccgtggaa tgccccatgt gtggaggaac gggcggttgg   4800
ccaggcgtaa gcggctgggt tgtctgccgg ccctgcaatg gcactggaac ccccaagccc   4860
gaggaatcgg cgtgacggtc gcaaaccatc cggcccggta caaatcggcg cggcgctggg   4920
tgatgacctg gtggagaagt tgaaggccgc gcaggccgcc cagcggcaac gcatcgaggc   4980
agaagcacgc cccggtgaat cgtggcaagc ggccgctgat cgaatccgca aagaatcccg   5040
gcaaccgccg gcagccggtg cgccgtcgat taggaagccg cccaagggcg acgagcaacc   5100
agatttttc gttccgatgc tctatgacgt gggcacccgc gatagtcgca gcatcatgga   5160
cgtggccgtt ttccgtctgt cgaagcgtga ccgacgagct ggcgaggtga tccgctacga   5220
gcttccagac gggcacgtag aggtttccgc agggccggcc ggcatggcca gtgtgtggga   5280
ttacgacctg gtactgatgg cggtttccca tctaaccgaa tccatgaacc gataccggga   5340
agggaaggga gacaagcccg gccgcgtgtt ccgtccacac gttgcggacg tactcaagtt   5400
ctgccggcga gccgatggcg gaaagcagaa agacgacctg gtagaaacct gcattcggtt   5460
aaacaccacg cacgttgcca tgcagcgtac gaagaaggcc aagaacggcc gcctggtgac   5520
ggtatccgag ggtgaagcct tgattagccg ctacaagatc gtaaagagcg aaaccgggcg   5580
gccggagtac atcgagatcg agctagctga ttggatgtac cgcgagatca cagaaggcaa   5640
gaacccggac gtgctgacgg ttcaccccga ttactttttg atcgatcccg gcatcggccg   5700
ttttctctac cgcctggcac gccgcgccgc aggcaaggca gaagccagat ggttgttcaa   5760
gacgatctac gaacgcagtg gcagcgccgg agagttcaag aagttctgtt tcaccgtgcg   5820
caagctgatc gggtcaaatg acctgccgga gtacgatttg aaggaggagg cggggcaggc   5880
tggcccgatc ctagtcatgc gctaccgcaa cctgatcgag ggcgaagcat ccgccggttc   5940
ctaatgtacg gagcagatgc tagggcaaat tgccctagca ggggaaaaag gtcgaaaagg   6000
tctctttcct gtggatagca cgtacattgg gaacccaaag ccgtacattg ggaaccggaa   6060
cccgtacatt gggaacccaa agccgtacat tgggaaccgg tcacacatgt aagtgactga   6120
tataaaagag aaaaaaggcg atttttccgc ctaaaactct ttaaaactta ttaaaactct   6180
taaaacccgc ctggcctgtg cataactgtc tggccagcgc acagccgaag agctgcaaaa   6240
agcgcctacc cttcggtcgc tgcgctccct acgccccgcc gcttcgcgtc ggcctatcgc   6300
ggccgctggc cgctcaaaaa tggctggcct acggccaggc aatctaccag ggcgcggaca   6360
agccgcgccg tcgccactcg accgccggcg cccacatcaa ggcaccctgc ctcgcgcgtt   6420
```

-continued tcggtgatga cggtgaaaac ctctgacaca tgcagctccc ggagacggtc acagcttgtc 6480
tgtaagcgga tgccgggagc agacaagccc gtcagggcgc gtcagcgggt gttggcgggt 6540
gtcggggcgc agccatgacc cagtcacgta gcgatagcgg agtgtatact ggcttaacta 6600
tgcggcatca gagcagattg tactgagagt gcaccatatg cggtgtgaaa taccgcacag 6660
atgcgtaagg agaaaatacc gcatcaggcg ctcttccgct tcctcgctca ctgactcgct 6720
gcgctcggtc gttcggctgc ggcgagcggt atcagctcac tcaaaggcgg taatacggtt 6780
atccacagaa tcaggggata acgcaggaaa gaacatgtga gcaaaaggcc agcaaaaggc 6840
caggaaccgt aaaaaggccg cgttgctggc gtttttccat aggctccgcc cccctgacga 6900
gcatcacaaa aatcgacgct caagtcagag gtggcgaaac ccgacaggac tataaagata 6960
ccaggcgttt ccccctggaa gctccctcgt gcgctctcct gttccgaccc tgccgcttac 7020
cggatacctg tccgcctttc tcccttcggg aagcgtggcg ctttctcata gctcacgctg 7080
taggtatctc agttcggtgt aggtcgttcg ctccaagctg ggctgtgtgc acgaaccccc 7140
cgttcagccc gaccgctgcg ccttatccgg taactatcgt cttgagtcca acccggtaag 7200
acacgactta tcgccactgg cagcagccac tggtaacagg attagcagag cgaggtatgt 7260
aggcggtgct acagagttct tgaagtggtg gcctaactac ggctacacta gaaggacagt 7320
atttggtatc tgcgctctgc tgaagccagt taccttcgga aaaagagttg gtagctcttg 7380
atccggcaaa caaaccaccg ctggtagcgg tggttttttt gtttgcaagc agcagattac 7440
gcgcagaaaa aaaggatctc aagaagatcc tttgatcttt tctacggggt ctgacgctca 7500
gtggaacgaa aactcacgtt aagggatttt ggtcatgcat tctaggtact aaaacaattc 7560
atccagtaaa atataatatt ttattttctc ccaatcaggc ttgatcccca gtaagtcaaa 7620
aaatagctcg acatactgtt cttccccgat atcctccctg atcgaccgga cgcagaaggc 7680
aatgtcatac cacttgtccg ccctgccgct tctcccaaga tcaataaagc cacttacttt 7740
gccatctttc acaaagatgt tgctgtctcc caggtcgccg tgggaaaaga caagttcctc 7800
ttcgggcttt tccgtcttta aaaaatcata cagctcgcgc ggatctttaa atggagtgtc 7860
ttcttcccag ttttcgcaat ccacatcggc cagatcgtta ttcagtaagt aatccaattc 7920
ggctaagcgg ctgtctaagc tattcgtata gggacaatcc gatatgtcga tggagtgaaa 7980
gagcctgatg cactccgcat acagctcgat aatcttttca gggctttgtt catcttcata 8040
ctcttccgag caaaggacgc catcggcctc actcatgagc agattgctcc agccatcatg 8100
ccgttcaaag tgcaggacct ttggaacagg cagctttcct tccagccata gcatcatgtc 8160
cttttcccgt tccacatcat aggtggtccc tttataccgg ctgtccgtca tttttaaata 8220
taggttttca ttttctccca ccagcttata taccttagca ggagacattc cttccgtatc 8280
ttttacgcag cggtattttt cgatcagttt tttcaattcc ggtgatattc tcattttagc 8340
catttattat ttccttcctc ttttctacag tatttaaaga taccccaaga agctaattat 8400
aacaagacga actccaattc actgttcctt gcattctaaa accttaaata ccagaaaaca 8460
gctttttcaa agttgttttc aaagttggcg tataacatag tatcgacgga gccgattttg 8520
aaaccgcggt gatcacaggc agcaacgctc tgtcatcgtt acaatcaaca tgctaccctc 8580
cgcgagatca tccgtgtttc aaacccggca gcttagttgc cgttcttccg aatagcatcg 8640
gtaacatgag caaagtctgc cgccttacaa cggctctccc gctgacgccg tcccggactg 8700
atgggctgcc tgtatcgagt ggtgattttg tgccgagctg ccggtcgggg agctgttggc 8760

```
tggctggtgg caggatatat tgtggtgtaa acaaattgac gcttagacaa cttaataaca   8820

cattgcggac gtttttaatg tactgaatta acgccgaatt aattcctagg ccaccatgtt   8880

gggcccggcg cgccaagctt gcatgcctgc aggtcaacat ggtggagcac gacactctcg   8940

tctactccaa gaatatcaaa gatacagtct cagaagacca gagggctatt gagacttttc   9000

aacaaagggt aatatcggga aacctcctcg gattccattg cccagctatc tgtcacttca   9060

tcgaaaggac agtagaaaag gaagatggct tctacaaatg ccatcattgc gataaaggaa   9120

aggctatcgt tcaagatgcc tctaccgaca gtggtcccaa agatggaccc ccacccacga   9180

ggaacatcgt ggaaaaagaa gacgttccaa ccacgtcttc aaagcaagtg gattgatgtg   9240

atggtcaaca tggtggagca cgacactctc gtctactcca agaatatcaa agatacagtc   9300

tcagaagacc agagggctat tgagactttt caacaaaggg taatatcggg aaacctcctc   9360

ggattccatt gcccagctat ctgtcacttc atcgaaagga cagtagaaaa ggaagatggc   9420

ttctacaaat gccatcattg cgataaagga aaggctatcg ttcaagatgc ctctaccgac   9480

agtggtccca aagatggacc cccacccacg aggaacatcg tggaaaaaga agacgttcca   9540

accacgtctt caaagcaagt ggattgatgt gatatctcca ctgacgtaag ggatgacgca   9600

caatcccact atccttcgca agacccttcc tctatataag gaagttcatt tcatttggag   9660

agg                                                                 9663
```

<210> SEQ ID NO 19
<211> LENGTH: 7117
<212> TYPE: DNA
<213> ORGANISM: Artificial Sequence
<220> FEATURE:
<223> OTHER INFORMATION: Truncated T7 driven Tobacco Rattle Virus RNA1( T7-RNA1 inducer)

<400> SEQUENCE: 19

```
taatacgact cactatagat aaaacatttc aatcctttga acgcggtaga acgtgctaat     60

tggattttgg tgagaacgcg gtagaacgta cttatcacct acagttttat tttgtttttc    120

tttttggttt aatctatcca gcttagtacc gagtggggga aagtgactgg tgtgcctaaa    180

accttttctt tgatactttg taaaaataca tacagataca atggcgaacg gtaacttcaa    240

gttgtctcaa ttgctcaatg tggacgagat gtctgctgag cagaggagtc atttctttga    300

cttgatgctg actaaacctg attgtgagat cgggcaaatg atgcaaagag ttgttgttga    360

taaagtcgat gacatgatta gagaaagaaa gactaaagat ccagtgattg ttcatgaagt    420

tctttctcag aaggaacaga acaagttgat ggaaatttat cctgaattca atatcgtgtt    480

taaagacgac aaaaacatgg ttcatgggtt tgcggctgct gagcgaaaac tacaagcttt    540

attgctttta gatagagttc ctgctctgca agaggtggat gacatcggtg gtcaatggtc    600

gttttgggta actagaggtg agaaaaggat tcattcctgt tgtccaaatc tagatattcg    660

ggatgatcag agagaaattt ctcgacagat atttcttact gctattggtg atcaagctag    720

aagtggtaag agacagatgt cggagaatga gctgtggatg tatgaccaat ttcgtgaaaa    780

tattgctgcg cctaacgcgg ttaggtgcaa taatacatat cagggttgta catgtagggg    840

tttttctgat ggtaagaaga aaggcgcgca gtatgcgata gctcttcaca gcctgtatga    900

cttcaagttg aaagacttga tggctactat ggttgagaag aaaactaaag tggttcatgc    960

tgctatgctt tttgctcctg aaagtatgtt agtggacgaa ggtccattac cttctgttga   1020

cggttactac atgaagaaga acgggaagat ctatttcggt tttgagaaag atccttcctt   1080
```

-continued

```
ttcttacatt catgactggg aagagtacaa gaagtatcta ctggggaagc cagtgagtta   1140
ccaagggaat gtgttctact tcgaaccgtg gcaggtgaga ggagacacaa tgcttttttc   1200
gatctacagg atagctggag ttccgaggag gtctctatca tcgcaagagt actaccgaag   1260
aatatatatc agtagatggg aaaacatggt tgttgtccca attttcgatc tggtcgaatc   1320
aacgcgagag ttggtcaaga aagacctgtt tgtagagaaa caattcatgg acaagtgttt   1380
ggattacata gctaggttat ctgaccagca gctgaccata agcaatgtta aatcatactt   1440
gagttcaaat aattgggtct tattcataaa cggggcggcc gtgaagaaca agcaaagtgt   1500
agattctcga gatttacagt tgttggctca aactttgcta gtgaaggaac aagtggcgag   1560
acctgtcatg agggagttgc gtgaagcaat tctgactgag acgaaaccta tcacgtcatt   1620
gactgatgtg ctgggtttaa tatcaagaaa actgtggaag cagtttgcta acaagatcgc   1680
agtcggcgga ttcgttggca tggttggtac tctaattgga ttctatccaa agaaggtact   1740
aacctgggcg aaggacacac caaatggtcc agaactatgt tacgagaact cgcacaaaac   1800
caaggtgata gtatttctga gtgttgtgta tgccattgga ggaatcacgc ttatgcgtcg   1860
agacatccga gatggactgg tgaaaaaact atgtgatatg tttgatatca aacggggggc   1920
ccatgtctta gacgttgaga atccgtgccg ctattatgaa atcaacgatt tctttagcag   1980
tctgtattcg gcatctgagt ccggtgagac cgttttacca gatttatccg aggtaaaagc   2040
caagtctgat aagctattgc agcagaagaa agaaatcgct gacgagtttc taagtgcaaa   2100
attctctaac tattctggca gttcggtgag aacttctcca ccatcggtgg tcggttcatc   2160
tcgaagcgga ctgggtctgt tgttggaaga cagtaacgtg ctgacccaag ctagagttgg   2220
agtttcaaga aaggtagacg atgaggagat catggagcag tttctgagtg gtcttattga   2280
cactgaagca gaaattgacg aggttgttcc agccttttca gctgaatgtg aaagagggga   2340
aacaagcggt acaaaggtgt tgtgtaaacc tttaacgcca ccaggatttg agaacgtgtt   2400
gccagctgtc aaacctttgg tcagcaaagg aaaaacggtc aaacgtgtcg attacttcca   2460
agtgatggga ggtgagagat taccaaaaag gccggttgtc agtggagacg attctgtgga   2520
cgctagaaga gagtttctgt actacttaga tgcggagaga gtcgctcaaa atgatgaaat   2580
tatgtctctg tatcgtgact attcgagagg agttattcga actggaggtc agaattaccc   2640
gcacggactg ggagtgtggg atgtggagat gaagaactgg tgcatacgtc cagtggtcac   2700
tgaacatgct tatgtgttcc aaccagacaa acgtatggat gattggtcgg gatacttaga   2760
agtggctgtt tgggaacgag gtatgttggt caacgacttc gcggtcgaaa ggatgagtga   2820
ttatgtcata gtttgcgatc agacgtatct ttgcaataac aggttgatct tggacaattt   2880
aagtgccctg gatctaggac cagttaactg ttcttttgaa ttagttgacg gtgtacctgg   2940
ttgtggtaag tcgacaatga ttgtcaactc agctaatcct tgtgtcgatg tggttctctc   3000
tactgggaga gcagcaaccg acgacttgat cgagagattc gcgagcaaag gttttccatg   3060
caaattgaaa aggagagtga agacggttga ttcttttttg atgcattgtg ttgatggttc   3120
tttaaccgga gacgtgttgc atttcgatga agctctcatg gcccatgctg gtatggtgta   3180
cttttgcgct cagatagctg gtgctaaacg atgtatctgt caaggagatc agaatcaaat   3240
ttctttcaag cctagggtat ctcaagttga tttgaggttt tctagtctgg tcggaaagtt   3300
tgacattgtt acagaaaaaa gagaaactta cagaagtcca gcagatgtgg ctgccgtatt   3360
gaacaagtac tatactggag atgtcagaac acataacgcg actgctaatt cgatgacggt   3420
gaggaagatt gtgtctaaag aacaggtttc tttgaagcct ggtgctcagt acataacttt   3480
```

-continued

```
ccttcagtct gagaagaagg agttggtaaa tttgttggca ttgaggaaag tggcagctaa   3540
agtgagtaca gtacacgagt cgcaaggaga gacattcaaa gatgtagtcc tagtcaggac   3600
gaaacctacg gatgactcaa tcgctagagg tcgggagtac ttaatcgtgg cgttgtcgcg   3660
tcacacacaa tcacttgtgt atgaaactgt gaaagaggac gatgtaagca aagagatcag   3720
ggaaagtgcc gcgcttacga aggcggcttt ggcaagattt tttgttactg agaccgtctt   3780
atgacggttt cggtctaggt ttgatgtctt tagacatcat gaagggcctt gcgccgttcc   3840
agattcaggt acgattacgg acttggagat gtggtacgac gctttgtttc cgggaaattc   3900
gttaagagac tcaagcctag acgggtattt ggtggcaacg actgattgca atttgcgatt   3960
agacaatgtt acgatcaaaa gtggaaactg gaaagacaag tttgctgaaa aagaaacgtt   4020
tctgaaaccg gttattcgta ctgctatgcc tgacaaaagg aagactactc agttggagag   4080
tttgttagca ttgcagaaaa ggaaccaagc ggcacccgat ctacaagaaa atgtgcacgc   4140
aacagttcta atcgaagaga cgatgaagaa gttgaaatct gttgtctacg atgtgggaaa   4200
aattcgggct gatcctattg tcaatagagc tcaaatggag agatggtgga gaaatcaaag   4260
cacagcggta caggctaagg tagtagcaga tgtgagagag ttacatgaaa tagactattc   4320
gtcttacatg tatatgatca aatctgacgt gaaacctaag actgatttaa caccgcaatt   4380
tgaatactca gctctacaga ctgttgtgta tcacgagaag ttgatcaact cgttgttcgg   4440
tccaattttc aaagaaatta atgaacgcaa gttggatgct atgcaaccac attttgtgtt   4500
caacacgaga atgacatcga gtgatttaaa cgatcgagtg aagttcttaa atacggaagc   4560
ggcttacgac tttgttgaga tagacatgtc taaattcgac aagtcggcaa atcgcttcca   4620
tttacaactg cagctggaga tttacaggtt atttgggcta gatgagtggg cggccttcct   4680
ttgggaggtg tcgcacactc aaactactgt gagagatatt caaaatggta tgatggcgca   4740
tatttggtac caacaaaaga gtggagatgc tgatacttat aatgcaaatt cagatagaac   4800
actgtgtgca ctcttgtctg aattaccatt ggagaaagca gtcatggtta catatggagg   4860
agatgactca ctgattgcgt ttcctagagg aacgcagttt gttgatccgt gtccaaagtt   4920
ggctactaag tggaatttcg agtgcaagat ttttaagtac gatgtcccaa tgttttgtgg   4980
gaagttcttg cttaagacgt catcgtgtta cgagttcgtg ccagatccgg taaaagttct   5040
gacgaagttg gggaaaaaga gtataaagga tgtgcaacat ttagccgaga tctacatctc   5100
gctgaatgat tccaatagag ctcttgggaa ctacatggtg gtatccaaac tgtccgagtc   5160
tgtttcagac cggtatttgt acaaaggtga ttctgttcat gcgctttgtg cgctatggaa   5220
gcatattaag agttttacag ctctgtgtac attattccga gacgaaaacg ataaggaatt   5280
gaacccggct aaggttgatt ggaagaaggc acagagagct gtgtcaaact tttacgactg   5340
gtaatatgga agacaagtca ttggtcacct tgaagaagaa gactttcgaa gtctcaaaat   5400
tctcaaatct aggggccatt gaattgtttg tggacggtag gaggaagaga ccgaagtatt   5460
ttcacagaag aagagaaact gtcctaaatc atgttggtgg gaagaagagt gaacacaagt   5520
tagacgtttt tgaccaaagg gattacaaaa tgattaaatc ttacgcgttt ctaaagatag   5580
taggtgtaca actagttgta acatcacatc tacctgcaga tacgcctggg ttcattcaaa   5640
tcgatctgtt ggattcgaga cttactgaga aaagaaagag aggaaagact attcagagat   5700
tcaaagctcg agcttgcgat aactgttcag ttgcgcagta caaggttgaa tacagtattt   5760
ccacacagga gaacgtactt gatgtctgga aggtgggttg tatttctgag ggcgttccgg   5820
```

```
tctgtgacgg tacataccct ttcagtatcg aagtgtcgct aatatgggtt gctactgatt   5880

cgactaggcg cctcaatgtg gaagaactga acagttcgga ttacattgaa ggcgatttta   5940

ccgatcaaga ggttttcggt gagttcatgt ctttgaaaca agtggagatg aagacgattg   6000

aggcgaagta cgatggtcct tacagaccag ctactactag acctaagtca ttattgtcaa   6060

gtgaagatgt taagagagcg tctaataaga aaaactcgtc ttaatgcata aagaaattta   6120

ttgtcaatat gacgtgtgta ctcaagggtt gtgtgaatga agtcactgtt cttggtcacg   6180

agacgtgtag tatcggtcat gctaacaaat tgcgaaagca agttgctgac atggttggtg   6240

tcacacgtag gtgtgcggaa aataattgtg gatggtttgt ctgtgttgtt atcaatgatt   6300

ttacttttga tgtgtataat tgttgtggcc gtagtcacct tgaaaagtgt cgtaaacgtg   6360

ttgaaacaag aaatcgagaa atttggaaac aaattcgacg aaatcaagct gaaaacatgt   6420

ctgcgacagc taaaaagtct cataattcga agacctctaa gaagaaattc aaagaggaca   6480

gagaatttgg gacaccaaaa agatttttaa gagatgatgt tcctttcggg attgatcgtt   6540

tgtttgcttt ttgattttat tttatattgt tatctgtttc tgtgtataga ctgtttgaga   6600

ttggcgcttg gccgactcat tgtcttacca taggggaacg gactttgttt gtgttgttat   6660

tttatttgta ttttattaaa attctcaatg atctgaaaag gcctcgaggc taagagatta   6720

ttgggggtg agtaagtact tttaaagtga tgatggttac aaaggcaaaa ggggtaaaac   6780

ccctcgccta cgtaagcgtt attacgcccg tctgtactta tatcagtaca ctgacgagtc   6840

cctaaaggac gaaacgggcc cgggcgttca aacatttggc aataaagttt cttaagattg   6900

aatcctgttg ccggtcttgc gatgattatc atataatttc tgttgaatta cgttaagcat   6960

gtaataatta acatgtaatg catgacgtta tttatgagat gggtttttat gattagagtc   7020

ccgcaattat acatttaata cgcgatagaa aacaaaatat agcgcgcaaa ctaggataaa   7080

ttatcgcgcg cggtgtcatc tatgttacta gatcggg                           7117
```

```
<210> SEQ ID NO 20
<211> LENGTH: 10665
<212> TYPE: DNA
<213> ORGANISM: Artificial Sequence
<220> FEATURE:
<223> OTHER INFORMATION: Synthetic sequence consisting of optimized TRV
      coat protein driven by T7 promoter and a strong RBS and TRV Ppk20
      TNAI and ribozyme sequence driven by T7 promoter.  All elements
      are in the pUC57 vector

<400> SEQUENCE: 20

gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300

ctgaagatca gttgggtgca cgagtgggtt acatcgaact ggatctcaac agcggtaaga    360

tccttgagag ttttcgcccc gaagaacgtt ttccaatgat gagcactttt aaagttctgc    420

tatgtggcgc ggtattatcc cgtattgacg ccgggcaaga gcaactcggt cgccgcatac    480

actattctca gaatgacttg gttgagtact caccagtcac agaaaagcat cttacggatg    540

gcatgacagt aagagaatta tgcagtgctg ccataaccat gagtgataac actgcggcca    600

acttacttct gacaacgatc ggaggaccga aggagctaac cgcttttttg cacaacatgg    660
```

-continued

```
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgactaat acgactcact atagggagac cacaacggtt   2100
tccctctaga aataattttg tttaacttta agaaggagat ataccatggc ggacatgtac   2160
gacgagtcgt tcgataagtc cggtggcccg gccgacttga tggacgacag ctgggtggaa   2220
tccgtcagct ggaaagattt gctgaaaaag ctccattcta tcaagtttgc gttacaatcc   2280
ggtcgtgatg agattaccgg cctgctggcg gccctgaacc gccagtgccc gtacagcccg   2340
tatgagcaat tcccagacaa aaaagtctat ttcctgctgg atagccgtgc taatagcgcc   2400
ctgggcgtta ttcagaatgc gtctgcgttt aagcgccgcg cggacgagaa gaacgcggtg   2460
gcgggcgtta ccaatatccc ggctaacccg aacaccacgg ttacgaccaa tcaaggtagc   2520
actaccacca ccaaggctaa caccggctcg accctggaag aggacttgta cacttactat   2580
aaatttgacg acgcgtcgac cgcattccac aaatcgctga cctccttgga aaatatggaa   2640
ctgaagtctt attaccgccg taacttcgag aaagtgtttg gtattaaatt tggtggcgca   2700
gccgcatcca gctcggcgcc gccaccggcg agcggtggcc cgattcgtcc gaatccttaa   2760
atgtcaggct cccttataca cagggtctca ctccgagctc gaatttcccc gatcgttcaa   2820
acatttggca ataaagtttc ttaagattga atcctgttgc cggtcttgcg atgattatca   2880
tataatttct gttgaattac gttaagcatg taataattaa catgtaatgc atgacgttat   2940
ttatgagatg ggtttttatg attagagtcc cgcaattata catttaatac gcgatagaaa   3000
acaaaatata gcgcgcaaac taggataaat tatcgcgcgc ggtgtcatct atgttactag   3060
```

-continued

```
atcggaggtt tcccgactgg aaagcgggca gtgagcgcaa cgcaattaat acgactcact   3120
atagataaaa catttcaatc ctttgaacgc ggtagaacgt gctaattgga ttttggtgag   3180
aacgcggtag aacgtactta tcacctacag ttttattttg tttttctttt tggtttaatc   3240
tatccagctt agtaccgagt gggggaaagt gactggtgtg cctaaaacct tttctttgat   3300
actttgtaaa aatacataca gatacaatgg cgaacggtaa cttcaagttg tctcaattgc   3360
tcaatgtgga cgagatgtct gctgagcaga ggagtcattt ctttgacttg atgctgacta   3420
aacctgattg tgagatcggg caaatgatgc aaagagttgt tgttgataaa gtcgatgaca   3480
tgattagaga aagaaagact aaagatccag tgattgttca tgaagttctt tctcagaagg   3540
aacagaacaa gttgatggaa atttatcctg aattcaatat cgtgtttaaa gacgacaaaa   3600
acatggttca tgggtttgcg gctgctgagc gaaaactaca agctttattg cttttagata   3660
gagttcctgc tctgcaagag gtggatgaca tcggtggtca atggtcgttt tgggtaacta   3720
gaggtgagaa aaggattcat tcctgttgtc caaatctaga tattcgggat gatcagagag   3780
aaatttctcg acagatattt cttactgcta ttggtgatca agctagaagt ggtaagagac   3840
agatgtcgga gaatgagctg tggatgtatg accaatttcg tgaaaatatt gctgcgccta   3900
acgcggttag gtgcaataat acatatcagg gttgtacatg taggggtttt tctgatggta   3960
agaagaaagg cgcgcagtat gcgatagctc ttcacagcct gtatgacttc aagttgaaag   4020
acttgatggc tactatggtt gagaagaaaa ctaaagtggt tcatgctgct atgctttttg   4080
ctcctgaaag tatgttagtg gacgaaggtc cattaccttc tgttgacggt tactacatga   4140
agaagaacgg gaagatctat ttcggttttg agaaagatcc ttccttttct tacattcatg   4200
actgggaaga gtacaagaag tatctactgg ggaagccagt gagttaccaa gggaatgtgt   4260
tctacttcga accgtggcag gtgagaggag acacaatgct tttttcgatc tacaggatag   4320
ctggagttcc gaggaggtct ctatcatcgc aagagtacta ccgaagaata tatatcagta   4380
gatgggaaaa catggttgtt gtcccaattt tcgatctggt cgaatcaacg cgagagttgg   4440
tcaagaaaga cctgtttgta gagaaacaat tcatggacaa gtgtttggat tacatagcta   4500
ggttatctga ccagcagctg accataagca atgttaaatc atacttgagt tcaaataatt   4560
gggtcttatt cataaacggg gcggccgtga agaacaagca aagtgtagat tctcgagatt   4620
tacagttgtt ggctcaaact ttgctagtga aggaacaagt ggcgagacct gtcatgaggg   4680
agttgcgtga agcaattctg actgagacga aacctatcac gtcattgact gatgtgctgg   4740
gtttaatatc aagaaaactg tggaagcagt ttgctaacaa gatcgcagtc ggcggattcg   4800
ttggcatggt tggtactcta attggattct atccaaagaa ggtactaacc tgggcgaagg   4860
acacaccaaa tggtccagaa ctatgttacg agaactcgca caaaaccaag gtgatagtat   4920
ttctgagtgt tgtgtatgcc attggaggaa tcacgcttat gcgtcgagac atccgagatg   4980
gactggtgaa aaaactatgt gatatgtttg atatcaaacg gggggcccat gtcttagacg   5040
ttgagaatcc gtgccgctat tatgaaatca acgatttctt tagcagtctg tattcggcat   5100
ctgagtccgg tgagaccgtt ttaccagatt tatccgaggt aaaagccaag tctgataagc   5160
tattgcagca gaagaaagaa atcgctgacg agtttctaag tgcaaaattc tctaactatt   5220
ctggcagttc ggtgagaact tctccaccat cggtggtcgg ttcatctcga agcggactgg   5280
gtctgttgtt ggaagacagt aacgtgctga cccaagctag agttggagtt tcaagaaagg   5340
tagacgatga ggagatcatg gagcagtttc tgagtggtct tattgacact gaagcagaaa   5400
```

-continued

```
ttgacgaggt tgttccagcc ttttcagctg aatgtgaaag aggggaaaca agcggtacaa   5460
aggtgttgtg taaaccttta acgccaccag gatttgagaa cgtgttgcca gctgtcaaac   5520
ctttggtcag caaaggaaaa acggtcaaac gtgtcgatta cttccaagtg atgggaggtg   5580
agagattacc aaaaaggccg gttgtcagtg gagacgattc tgtggacgct agaagagagt   5640
ttctgtacta cttagatgcg gagagagtcg ctcaaaatga tgaaattatg tctctgtatc   5700
gtgactattc gagaggagtt attcgaactg gaggtcagaa ttacccgcac ggactgggag   5760
tgtgggatgt ggagatgaag aactggtgca tacgtccagt ggtcactgaa catgcttatg   5820
tgttccaacc agacaaacgt atggatgatt ggtcgggata cttagaagtg gctgtttggg   5880
aacgaggtat gttggtcaac gacttcgcgg tcgaaaggat gagtgattat gtcatagttt   5940
gcgatcagac gtatctttgc aataacaggt tgatcttgga caatttaagt gccctggatc   6000
taggaccagt taactgttct tttgaattag ttgacggtgt acctggttgt ggtaagtcga   6060
caatgattgt caactcagct aatccttgtg tcgatgtggt tctctctact gggagagcag   6120
caaccgacga cttgatcgag agattcgcga gcaaaggttt tccatgcaaa ttgaaaagga   6180
gagtgaagac ggttgattct mttgatgcat tgtgttgatg gttctttaac cggagacgtg   6240
ttgcatttcg atgaagctct catggcccat gctggtatgg tgtacttttg cgctcagata   6300
gctggtgcta aacgatgtat ctgtcaagga gatcagaatc aaatttcttt caagcctagg   6360
gtatctcaag ttgatttgag gttttctagt ctggtcggaa agtttgacat tgttacagaa   6420
aaaagagaaa cttacagaag tccagcagat gtggctgccg tattgaacaa gtactatact   6480
ggagatgtca gaacacataa cgcgactgct aattcgatga cggtgaggaa gattgtgtct   6540
aaagaacagg tttctttgaa gcctggtgct cagtacataa ctttccttca gtctgagaag   6600
aaggagttgg taaatttgtt ggcattgagg aaagtggcag ctaaagtgag tacagtacac   6660
gagtcgcaag gagagacatt caaagatgta gtcctagtca ggacgaaacc tacggatgac   6720
tcaatcgcta gaggtcggga gtacttaatc gtggcgttgt cgcgtcacac acaatcactt   6780
gtgtatgaaa ctgtgaaaga ggacgatgta agcaaagaga tcagggaaag tgccgcgctt   6840
acgaaggcgg ctttggcaag attttttgtt actgagaccg tcttatgacg gtttcggtct   6900
aggtttgatg tctttagaca tcatgaaggg ccttgcgccg ttccagattc aggtacgatt   6960
acggacttgg agatgtggta cgacgctttg tttccgggaa attcgttaag agactcaagc   7020
ctagacgggt atttggtggc aacgactgat tgcaatttgc gattagacaa tgttacgatc   7080
aaaagtggaa actggaaaga caagtttgct gaaaaagaaa cgtttctgaa accggttatt   7140
cgtactgcta tgcctgacaa aaggaagact actcagttgg agagtttgtt agcattgcag   7200
aaaaggaacc aagcggcacc cgatctacaa gaaaatgtgc acgcaacagt tctaatcgaa   7260
gagacgatga agaagttgaa atctgttgtc tacgatgtgg gaaaaattcg ggctgatcct   7320
attgtcaata gagctcaaat ggagagatgg tggagaaatc aaagcacagc ggtacaggct   7380
aaggtagtag cagatgtgag agagttacat gaaatagact attcgtctta catgtatatg   7440
atcaaatctg acgtgaaacc taagactgat ttaacaccgc aatttgaata ctcagctcta   7500
cagactgttg tgtatcacga gaagttgatc aactcgttgt tcggtccaat tttcaaagaa   7560
attaatgaac gcaagttgga tgctatgcaa ccacattttg tgttcaacac gagaatgaca   7620
tcgagtgatt taaacgatcg agtgaagttc ttaaatacgg aagcggctta cgactttgtt   7680
gagatagaca tgtctaaatt cgacaagtcg gcaaatcgct tccatttaca actgcagctg   7740
gagatttaca ggttatttgg gctagatgag tgggcggcct tcctttggga ggtgtcgcac   7800
```

-continued

```
actcaaacta ctgtgagaga tattcaaaat ggtatgatgg cgcatatttg gtaccaacaa   7860
aagagtggag atgctgatac ttataatgca aattcagata gaacactgtg tgcactcttg   7920
tctgaattac cattggagaa agcagtcatg gttacatatg gaggagatga ctcactgatt   7980
gcgtttccta gaggaacgca gtttgttgat ccgtgtccaa agttggctac taagtggaat   8040
ttcgagtgca agatttttaa gtacgatgtc ccaatgtttt gtgggaagtt cttgcttaag   8100
acgtcatcgt gttacgagtt cgtgccagat ccggtaaaag ttctgacgaa gttggggaaa   8160
aagagtataa aggatgtgca acatttagcc gagatctaca tctcgctgaa tgattccaat   8220
agagctcttg ggaactacat ggtggtatcc aaactgtccg agtctgtttc agaccggtat   8280
ttgtacaaag gtgattctgt tcatgcgctt tgtgcgctat ggaagcatat taagagtttt   8340
acagctctgt gtacattatt ccgagacgaa aacgataagg aattgaaccc ggctaaggtt   8400
gattggaaga aggcacagag agctgtgtca aacttttacg actggtaata tggaagacaa   8460
gtcattggtc accttgaaga agaagacttt cgaagtctca aaattctcaa atctaggggc   8520
cattgaattg tttgtggacg gtaggaggaa gagaccgaag tattttcaca gaagaagaga   8580
aactgtccta aatcatgttg gtgggaagaa gagtgaacac aagttagacg tttttgacca   8640
aagggattac aaaatgatta aatcttacgc gtttctaaag atagtaggtg tacaactagt   8700
tgtaacatca catctacctg cagatacgcc tgggttcatt caaatcgatc tgttggattc   8760
gagacttact gagaaaagaa agagaggaaa gactattcag agattcaaag ctcgagcttg   8820
cgataactgt tcagttgcgc agtacaaggt tgaatacagt atttccacac aggagaacgt   8880
acttgatgtc tggaaggtgg gttgtatttc tgagggcgtt ccggtctgtg acggtacata   8940
ccctttcagt atcgaagtgt cgctaatatg ggttgctact gattcgacta ggcgcctcaa   9000
tgtggaagaa ctgaacagtt cggattacat tgaaggcgat tttaccgatc aagaggtttt   9060
cggtgagttc atgtctttga aacaagtgga gatgaagacg attgaggcga agtacgatgg   9120
tccttacaga ccagctacta ctagacctaa gtcattattg tcaagtgaag atgttaagag   9180
agcgtctaat aagaaaaact cgtcttaatg cataaagaaa tttattgtca atatgacgtg   9240
tgtactcaag ggttgtgtga atgaagtcac tgttcttggt cacgagacgt gtagtatcgg   9300
tcatgctaac aaattgcgaa agcaagttgc tgacatggtt ggtgtcacac gtaggtgtgc   9360
ggaaaataat tgtggatggt ttgtctgtgt tgttatcaat gattttactt ttgatgtgta   9420
taattgttgt ggccgtagtc accttgaaaa gtgtcgtaaa cgtgttgaaa caagaaatcg   9480
agaaatttgg aaacaaattc gacgaaatca agctgaaaac atgtctgcga cagctaaaaa   9540
gtctcataat tcgaagacct ctaagaagaa attcaaagag gacagagaat ttgggacacc   9600
aaaaagattt ttaagagatg atgttccttt cgggattgat cgtttgtttg ctttttgatt   9660
ttattttata ttgttatctg tttctgtgta tagactgttt gagattggcg cttggccgac   9720
tcattgtctt accatagggg aacggacttt gtttgtgttg ttattttatt tgtattttat   9780
taaaattctc aatgatctga aaaggcctcg aggctaagag attattgggg ggtgagtaag   9840
tacttttaaa gtgatgatgg ttacaaaggc aaaaggggta aaacccctcg cctacgtaag   9900
cgttattacg cccgtctgta cttatatcag tacactgacg agtccctaaa ggacgaaacg   9960
ggcccgggcg ttcaaacatt tggcaataaa gtttcttaag attgaatcct gttgccggtc  10020
ttgcgatgat tatcatataa tttctgttga attacgttaa gcatgtaata attaacatgt  10080
aatgcatgac gttatttatg agatgggttt ttatgattag agtcccgcaa ttatacattt  10140
```

-continued aatacgcgat agaaaacaaa atatagcgcg caaactagga taaattatcg cgcgcggtgt 10200
catctatgtt actagatcgg ggtcgggatc cgatatctag atgcattcgc gaggtaccga 10260
gctcgaattc actggccgtc gttttacaac gtcgtgactg ggaaaaccct ggcgttaccc 10320
aacttaatcg ccttgcagca catccccctt tcgccagctg gcgtaatagc gaagaggccc 10380
gcaccgatcg cccttcccaa cagttgcgca gcctgaatgg cgaatggcgc ctgatgcggt 10440
attttctcct tacgcatctg tgcggtattt cacaccgcat atggtgcact ctcagtacaa 10500
tctgctctga tgccgcatag ttaagccagc cccgacaccc gccaacaccc gctgacgcgc 10560
cctgacgggc ttgtctgctc ccggcatccg cttacagaca agctgtgacc gtctccggga 10620
gctgcatgtg tcagaggttt tcaccgtcat caccgaaacg cgcga 10665

<210> SEQ ID NO 21
<211> LENGTH: 2484
<212> TYPE: DNA
<213> ORGANISM: Artificial Sequence
<220> FEATURE:
<223> OTHER INFORMATION: Synthetic T7-RNA2-MCS inducer sequence
<220> FEATURE:
<221> NAME/KEY: misc_feature
<222> LOCATION: (1972)..(1972)
<223> OTHER INFORMATION: n is a, c, g, or t

<400> SEQUENCE: 21
taatacgact cactatagga taaaacattg cacctatggt gttgccctgg ctggggtatg 60
tcagtgatcg cagtagaatg tactaattga caagttggag aatacggtag aacgtcctta 120
tccaacacag cctttatccc tctccctgac gaggtttttg tcagtgtaat atttcttttt 180
gaactatcca gcttagtacc gtacgggaaa gtgactggtg tgcttatctt tgaaatgtta 240
ctttgggttt cggttcttta ggttagtaag aaagcacttg tcttctcata caaaggaaaa 300
cctgagacgt atcgcttacg aaagtagcaa tgaaagaaag gtggtggttt taatcgctac 360
cgcaaaaacg atggggtcgt tttaattaac ttctcctacg caagcgtcta aacggacgtt 420
ggggttttgc tagtttcttt agagaaaact agctaagtct ttaatgttat cattagagat 480
ggcataaata taatacttgt gtctgctgat aagatcattt taatttggac gattagactt 540
gttgaactac aggttactga atcacttgcg ctaatcaaca tgggagatat gtacgatgaa 600
tcatttgaca agtcgggcgg tcctgctgac ttgatggacg attcttgggt ggaatcagtt 660
tcgtggaaag atctgttgaa gaagttacac agcataaaat ttgcactaca gtctggtaga 720
gatgagatca ctgggttact agcggcactg aatagacagt gtccttattc accatatgag 780
cagtttccag ataagaaggt gtatttcctt ttagactcac gggctaacag tgctcttggt 840
gtgattcaga acgcttcagc gttcaagaga cgagctgatg agaagaatgc agtggcgggt 900
gttacaaata ttcctgcgaa tccaaacaca acggttacga cgaaccaagg gagtactact 960
actaccaagg cgaacactgg ctcgactttg gaagaagact tgtacactta ttacaaattc 1020
gatgatgcct ctacagcttt ccacaaatct ctaacttcgt tagagaacat ggagttgaag 1080
agttattacc gaaggaactt tgagaaagta ttcgggatta agtttggtgg agcagctgct 1140
agttcatctg caccgcctcc agcgagtgga ggtccgatac gtcctaatcc ctagggattt 1200
aaggacgtga actctgttga gatctctgtg aaattcagag ggtgggtgat accatattca 1260
ctgatgccat tagcgacatc taaatagggc taattgtgac taatttgagg gaatttcctt 1320
taccattgac gtcagtgtcg ttggtagcat ttgagtttcg caatgcacga attacttagg 1380
aagtggcttg acgacactaa tgtgttattg ttagataatg gtttggtggt caaggtacgt 1440

```
agtagagtcc cacatattcg cacgtatgaa gtaattggaa agttgtcagt ttttgataat   1500

tcactgggag atgatacgct gtttgaggga aaagtagaga acgtatttgt ttttatgttc   1560

aggcggttct tgtgtgtcaa caaagatgga cattgttact caaggaagca cgatgagctt   1620

tattattacg gacgagtgga cttagattct gtgagtaagg ttaccgaatt ctctagaagg   1680

cctccatggg gatccggtac cgagctcacg cgtctcgagg cccgggcatg tcccgaagac   1740

attaaactac ggttctttaa gtagatccgt gtctgaagtt ttaggttcaa tttaaaccta   1800

cgagattgac attctcgact gatcttgatt gatcggtaag tcttttgtaa tttaattttc   1860

tmtgatttta ttttaaattg ttatctgttt ctgtgtatag actgtttgag atcggcgttt   1920

ggccgactca ttgtcttacc ataggggaac ggactttgtt tgtgttgtta tntatttgta   1980

ttttattaaa attctcaacg atctgaaaaa gcctcgcggc taagagattg ttggggggtg   2040

agtaagtact tttaaagtga tgatggttac aaaggcaaaa ggggtaaaac ccctcgccta   2100

cgtaagcgtt attacgcccg tctgtactta tatcagtaca ctgacgagtc cctaaaggac   2160

gaaacgggag aacgctagcc accaccacca ccaccacgtg tgaattacag gtgaccagct   2220

cgaatttccc cgatcgttca aacatttggc aataaagttt cttaagattg aatcctgttg   2280

ccggtcttgc gatgattatc atataatttc tgttgaatta cgttaagcat gtaataatta   2340

acatgtaatg catgacgtta tttatgagat gggtttttat gattagagtc ccgcaattat   2400

acatttaata cgcgatagaa aacaaaatat agcgcgcaaa ctaggataaa ttatcgcgcg   2460

cggtgtcatc tatgttacta gatc                                          2484
```

<210> SEQ ID NO 22
<211> LENGTH: 3160
<212> TYPE: DNA
<213> ORGANISM: Artificial Sequence
<220> FEATURE:
<223> OTHER INFORMATION: Synthetic T7 driven RNA2 with sample construct (C3) in MCS, ribozyme, NOS

<400> SEQUENCE: 22

```
taatacgact cactatagga taaaacattg cacctatggt gttgccctgg ctggggtatg     60

tcagtgatcg cagtagaatg tactaattga caagttggag aatacggtag aacgtcctta    120

tccaacacag cctttatccc tctccctgac gaggttttttg tcagtgtaat atttcttttt    180

gaactatcca gcttagtacc gtacgggaaa gtgactggtg tgcttatctt tgaaatgtta    240

ctttgggttt cggttcttta ggttagtaag aaagcacttg tcttctcata caaaggaaaa    300

cctgagacgt atcgcttacg aaagtagcaa tgaaagaaag gtggtggttt taatcgctac    360

cgcaaaaacg atggggtcgt tttaattaac ttctcctacg caagcgtcta aacggacgtt    420

ggggttttgc tagtttcttt agagaaaact agctaagtct ttaatgttat cattagagat    480

ggcataaata taatacttgt gtctgctgat aagatcattt taatttggac gattagactt    540

gttgaactac aggttactga atcacttgcg ctaatcaaca tgggagatat gtacgatgaa    600

tcatttgaca agtcgggcgg tcctgctgac ttgatggacg attcttgggt ggaatcagtt    660

tcgtggaaag atctgttgaa gaagttacac agcataaaat ttgcactaca gtctggtaga    720

gatgagatca ctgggttact agcggcactg aatagacagt gtccttattc accatatgag    780

cagtttccag ataagaaggt gtatttcctt ttagactcac gggctaacag tgctcttggt    840

gtgattcaga acgcttcagc gttcaagaga cgagctgatg agaagaatgc agtggcgggt    900

gttacaaata ttcctgcgaa tccaaacaca acggttacga cgaaccaagg gagtactact    960
```

-continued actaccaagg cgaacactgg ctcgactttg gaagaagact tgtacactta ttacaaattc 1020
gatgatgcct ctacagcttt ccacaaatct ctaacttcgt tagagaacat ggagttgaag 1080
agttattacc gaaggaactt tgagaaagta ttcgggatta agtttggtgg agcagctgct 1140
agttcatctg caccgcctcc agcgagtgga ggtccgatac gtcctaatcc ctagggattt 1200
aaggacgtga actctgttga gatctctgtg aaattcagag ggtgggtgat accatattca 1260
ctgatgccat tagcgacatc taaatagggc taattgtgac taatttgagg gaatttcctt 1320
taccattgac gtcagtgtcg ttggtagcat ttgagtttcg caatgcacga attacttagg 1380
aagtggcttg acgacactaa tgtgttattg ttagataatg gtttggtggt caaggtacgt 1440
agtagagtcc cacatattcg cacgtatgaa gtaattggaa agttgtcagt ttttgataat 1500
tcactgggag atgatacgct gtttgaggga aaagtagaga acgtatttgt ttttatgttc 1560
aggcggttct tgtgtgtcaa caaagatgga cattgttact caaggaagca cgatgagctt 1620
tattattacg gacgagtgga cttagattct gtgagtaatc tgaccaggtc tcatcgtgtc 1680
gacggaggaa gtgaagcaca gaaatggaac aaaaataaaa ccttggggta ctctttgatc 1740
ttctttgcaa gaatgtaatg aatatccctg attactttct tcatataccg tccgtcaagt 1800
gccttcaatt gctgaagcca aatcctaaat cccataccac aagattacag gcatagagtc 1860
tcgaagcatt attaataact cattggcgat caaattaaga tgaatgtcag tttattaaag 1920
gaaaaagtaa agaacaagaa caaaatcatt tggcactttt catactacaa ccatcgacaa 1980
aattagctgc tgccactgct tctttgacat gtaatacggg agactcactg ctatttcatt 2040
atttggctca aggcaaagga attaggagat gaagtggatg gatatgatga aagctcctcc 2100
gccaccacct aatcaataca atagcagcag tagtactaat aaccttagcc aaagcaaaga 2160
aatcagagaa gaagaagagc gaaaaagctt gccttcttct ccatacaatc cggccaaagt 2220
ttcaatatcc ggatcatgga caccaataac aatacttata ggatcactat acagcaaacg 2280
agatgcaatt ttagctaaga cagaagtttc acaagctcat ttagagctgt taaagaagac 2340
taatgaagca gcaatagaag aaacagagaa gcaatctcga gctcctgaga cctggtcctc 2400
atgtcccgaa gacattaaac tacggttctt taagtagatc cgtgtctgaa gttttaggtt 2460
caatttaaac ctacgagatt gacattctcg actgatcttg attgatcggt aagtcttttg 2520
taatttaatt ttctttttga ttttatttta aattgttatc tgtttctgtg tatagactgt 2580
ttgagatcgg cgtttggccg actcattgtc ttaccatagg ggaacggact ttgtttgtgt 2640
tgttatttta tttgtatttt attaaaattc tcaacgatct gaaaaagcct cgcggctaag 2700
agattgttgg ggggtgagta agtactttta aagtgatgat ggttacaaag gcaaaagggg 2760
taaaacccct cgcctacgta agcgttatta cgcccgtctg tacttatatc agtacactga 2820
cgagtcccta aaggacgaaa cgggagaacg ctagccacca ccaccaccac cacgtgtgaa 2880
ttacaggtga ccagctcgaa tttccccgat cgttcaaaca tttggcaata aagtttctta 2940
agattgaatc ctgttgccgg tcttgcgatg attatcatat aatttctgtt gaattacgtt 3000
aagcatgtaa taattaacat gtaatgcatg acgttattta tgagatgggt ttttatgatt 3060
agagtcccgc aattatacat ttaatacgcg atagaaaaca aaatatagcg cgcaaactag 3120
gataaattat cgcgcgcggt gtcatctatg ttactagatc 3160

<210> SEQ ID NO 23
<211> LENGTH: 3232
<212> TYPE: DNA

<213> ORGANISM: Artificial Sequence
<220> FEATURE:
<223> OTHER INFORMATION: Synthetic T7-RNA2-sgP-C3 sequence

<400> SEQUENCE: 23

```
taatacgact cactatagga taaaacattg cacctatggt gttgccctgg ctggggtatg     60
tcagtgatcg cagtagaatg tactaattga caagttggag aatacggtag aacgtcctta    120
tccaacacag cctttatccc tctccctgac gaggtttttg tcagtgtaat atttcttttt    180
gaactatcca gcttagtacc gtacgggaaa gtgactggtg tgcttatctt tgaaatgtta    240
ctttgggttt cggttcttta ggttagtaag aaagcacttg tcttctcata caaaggaaaa    300
cctgagacgt atcgcttacg aaagtagcaa tgaaagaaag gtggtggttt taatcgctac    360
cgcaaaaacg atggggtcgt tttaattaac ttctcctacg caagcgtcta aacggacgtt    420
ggggttttgc tagtttcttt agagaaaact agctaagtct ttaatgttat cattagagat    480
ggcataaata taatacttgt gtctgctgat aagatcattt taatttggac gattagactt    540
gttgaactac aggttactga atcacttgcg ctaatcaaca tgggagatat gtacgatgaa    600
tcatttgaca agtcgggcgg tcctgctgac ttgatggacg attcttgggt ggaatcagtt    660
tcgtggaaag atctgttgaa gaagttacac agcataaaat ttgcactaca gtctggtaga    720
gatgagatca ctgggttact agcggcactg aatagacagt gtccttattc accatatgag    780
cagtttccag ataagaaggt gtatttcctt ttagactcac gggctaacag tgctcttggt    840
gtgattcaga acgcttcagc gttcaagaga cgagctgatg agaagaatgc agtggcgggt    900
gttacaaata ttcctgcgaa tccaaacaca acggttacga cgaaccaagg gagtactact    960
actaccaagg cgaacactgg ctcgactttg gaagaagact tgtacactta ttacaaattc   1020
gatgatgcct ctacagcttt ccacaaatct ctaacttcgt tagagaacat ggagttgaag   1080
agttattacc gaaggaactt tgagaaagta ttcgggatta agtttggtgg agcagctgct   1140
agttcatctg caccgcctcc agcgagtgga ggtccgatac gtcctaatcc ctagggattt   1200
aaggacgtga actctgttga gatctctgtg aaattcagag ggtgggtgat accatattca   1260
ctgatgccat tagcgacatc taaatagggc taattgtgac taatttgagg gaatttcctt   1320
taccattgac gtcagtgtcg ttggtagcat ttgagtttcg gagcatcttg ttctggggtt   1380
tcacactatc tttagagaaa gtgttaagtt aattaagtta tcttaattaa gagcataatt   1440
atactgattt gtctctcgtt gatagagtct atcattctgt tactaaaaat ttgacaactc   1500
ggtttgctga cctactggtt actgtatcac ttacccgagt taacgaggga ggaagtgaag   1560
cacagaaatg gaacaaaaat aaaaccttgg ggtactcttt gatcttcttt gcaagaatgt   1620
aatgaatatc cctgattact ttcttcatat accgtccgtc aagtgccttc aattgctgaa   1680
gccaaatcct aaatcccata ccacaagatt acaggcatag agtctcgaag cattattaat   1740
aactcattgg cgatcaaatt aagatgaatg tcagtttatt aaaggaaaaa gtaaagaaca   1800
agaacaaaat catttggcac ttttcatact acaaccatcg acaaaattag ctgctgccac   1860
tgcttctttg acatgtaata cgggagactc actgctattt cattatttgg ctcaaggcaa   1920
aggaattagg agatgaagtg gatggatatg atgaaagctc ctccgccacc acctaatcaa   1980
tacaatagca gcagtagtac taataacctt agccaaagca aagaaatcag agaagaagaa   2040
gagcgaaaaa gcttgccttc ttctccatac aatccggcca aagtttcaat atccggatca   2100
tggacaccaa taacaatact tataggatca ctatacagca aacgagatgc aattttagct   2160
aagacagaag tttcacaagc tcatttagag ctgttaaaga agactaatga agcagcaata   2220
```

-continued gaagaaacag agaagcaatc tcgagctcct gagacctggt cctcctcgtt aactcgggta 2280
agtgatacag taaccagtag gtcagcaaac cgagttgtca aatttttagt aacagaatga 2340
tagactctat caacgagaga caaatcagta taattatgct cttaattaag ataacttaat 2400
taacttaaca ctttctctaa agatagtgtg aaaccccaga acaagatgct catgtcccga 2460
agacattaaa ctacggttct ttaagtagat ccgtgtctga agttttaggt tcaatttaaa 2520
cctacgagat tgacattctc gactgatctt gattgatcgg taagtctttt gtaatttaat 2580
tttctttttg attttatttt aaattgttat ctgtttctgt gtatagactg tttgagatcg 2640
gcgtttggcc gactcattgt cttaccatag gggaacggac tttgtttgtg ttgttatttt 2700
atttgtattt tattaaaatt ctcaacgatc tgaaaaagcc tcgcggctaa gagattgttg 2760
gggggtgagt aagtactttt aaagtgatga tggttacaaa ggcaaaaggg gtaaaacccc 2820
tcgcctacgt aagcgttatt acgcccgtct gtacttatat cagtacactg acgagtccct 2880
aaaggacgaa acgggagaac gctagccacc accaccacca ccacgtgtga attacaggtg 2940
accagctcga atttccccga tcgttcaaac atttggcaat aaagtttctt aagattgaat 3000
cctgttgccg gtcttgcgat gattatcata taatttctgt tgaattacgt taagcatgta 3060
ataattaaca tgtaatgcat gacgttattt atgagatggg tttttatgat tagagtcccg 3120
caattataca tttaatacgc gatagaaaac aaaatatagc gcgcaaacta ggataaatta 3180
tcgcgcgcgg tgtcatctat gttactagat cgggaattaa actatcagtg tt 3232

<210> SEQ ID NO 24
<211> LENGTH: 2823
<212> TYPE: DNA
<213> ORGANISM: Artificial Sequence
<220> FEATURE:
<223> OTHER INFORMATION: Synthetic sequence consisting of PUC57 MCS flanked by PEBV subgenomic promoters all of which are flanked by T7 promoters
<220> FEATURE:
<221> NAME/KEY: misc_feature
<222> LOCATION: (1720)..(1720)
<223> OTHER INFORMATION: n is a, c, g or t

<400> SEQUENCE: 24
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaataata cgactcacta tagggagata ccattgacgt 180
cagtgtcgtt ggtagcattt gagtttcgga gcatcttgtt ctggggtttc acactatctt 240
tagagaaagt gttaagttaa ttaagttatc ttaattaaga gcataattat actgatttgt 300
ctctcgttga tagagtctat cattctgtta ctaaaaattt gacaactcgg tttgctgacc 360
tactggttac tgtatcactt acccgagtta acgaggtgaa ttcgagctcg gtacctcgcg 420
aatgcatcta gatatcggat cccgggcccg tcgactgcag aggcctgcat gcaagcttgc 480
tcgttaactc gggtaagtga tacagtaacc agtaggtcag caaaccgagt tgtcaaattt 540
ttagtaacag aatgatagac tctatcaacg agagacaaat cagtataatt atgctcttaa 600
ttaagataac ttaattaact taacactttc tctaaagata gtgtgaaacc ccagaacaag 660
atgctccgaa actcaaatgc taccaacgac actgacgtca atggtatctc cctatagtga 720
gtcgtattat cactgcccgc tttccagtcg ggaaacctgt cgtgccagct gcattaatga 780
atcggccaac gcgcggggag aggcggtttg cgtattgggc gctcttccgc ttcctcgctc 840

```
actgactcgc tgcgctcggt cgttcggctg cggcgagcgg tatcagctca ctcaaaggcg    900
gtaatacggt tatccacaga atcaggggat aacgcaggaa agaacatgtg agcaaaaggc    960
cagcaaaagg ccaggaaccg taaaaaggcc gcgttgctgg cgtttttcca taggctccgc   1020
cccccctgacg agcatcacaa aaatcgacgc tcaagtcaga ggtggcgaaa cccgacagga   1080
ctataaagat accaggcgtt tccccctgga agctccctcg tgcgctctcc tgttccgacc   1140
ctgccgctta ccggatacct gtccgccttt ctcccttcgg gaagcgtggc gctttctcat   1200
agctcacgct gtaggtatct cagttcggtg taggtcgttc gctccaagct gggctgtgtg   1260
cacgaacccc ccgttcagcc cgaccgctgc gccttatccg gtaactatcg tcttgagtcc   1320
aacccggtaa gacacgactt atcgccactg gcagcagcca ctggtaacag gattagcaga   1380
gcgaggtatg taggcggtgc tacagagttc ttgaagtggt ggcctaacta cggctacact   1440
agaagaacag tatttggtat ctgcgctctg ctgaagccag ttaccttcgg aaaaagagtt   1500
ggtagctctt gatccggcaa acaaaccacc gctggtagcg gtggtttttt tgtttgcaag   1560
cagcagatta cgcgcagaaa aaaaggatct caagaagatc ctttgatctt ttctacgggg   1620
tctgacgctc agtggaacga aaactcacgt taagggattt tggtcatgag attatcaaaa   1680
aggatcttca cctagatcct tttaaattaa aaatgaagtn taaatcaatc taaagtatat   1740
atgagtaaac ttggtctgac agttaccaat gcttaatcag tgaggcacct atctcagcga   1800
tctgtctatt tcgttcatcc atagttgcct gactccccgt cgtgtagata actacgatac   1860
gggagggctt accatctggc cccagtgctg caatgatacc gcgagaccca cgctcaccgg   1920
ctccagattt atcagcaata aaccagccag ccggaagggc cgagcgcaga agtggtcctg   1980
caactttatc cgcctccatc cagtctatta attgttgccg ggaagctaga gtaagtagtt   2040
cgccagttaa tagtttgcgc aacgttgttg ccattgctac aggcatcgtg gtgtcacgct   2100
cgtcgtttgg tatggcttca ttcagctccg gttcccaacg atcaaggcga gttacatgat   2160
cccccatgtt gtgcaaaaaa gcggttagct ccttcggtcc tccgatcgtt gtcagaagta   2220
agttggccgc agtgttatca ctcatggtta tggcagcact gcataattct cttactgtca   2280
tgccatccgt aagatgcttt tctgtgactg gtgagtactc aaccaagtca ttctgagaat   2340
agtgtatgcg gcgaccgagt tgctcttgcc cggcgtcaat acgggataat accgcgccac   2400
atagcagaac tttaaaagtg ctcatcattg gaaaacgttc ttcggggcga aaactctcaa   2460
ggatcttacc gctgttgaga tccagttcga tgtaacccac tcgtgcaccc aactgatctt   2520
cagcatcttt tactttcacc agcgtttctg ggtgagcaaa aacaggaagg caaaatgccg   2580
caaaaaaggg aataagggcg acacggaaat gttgaatact catactcttc ctttttcaat   2640
attattgaag catttatcag ggttattgtc tcatgagcgg atacatattt gaatgtattt   2700
agaaaaataa acaaataggg gttccgcgca catttccccg aaaagtgcca cctgacgtct   2760
aagaaaccat tattatcatg acattaacct ataaaaatag gcgtatcacg aggccctttc   2820
gtc                                                                 2823
```

<210> SEQ ID NO 25
<211> LENGTH: 7560
<212> TYPE: RNA
<213> ORGANISM: Artificial Sequence
<220> FEATURE:
<223> OTHER INFORMATION: Synthetic RNA1 of TRV Ppk20 sequence

<400> SEQUENCE: 25

```
aagcuugcau gccugcaggu caacauggug gagcacgaca cucucgucua cuccaagaau     60
```

-continued

```
aucaaagaua cagucucaga agaccagagg gcuauugaga cuuuucaaca aagguaaua    120
ucgggaaacc uccucggauu ccauugccca gcuaucuguc acuucaucga aaggacagua    180
gaaaaggaag auggcuucua caaaugccau cauugcgaua aaggaaaggc uaucguucaa    240
gaugccucua ccgacagugg ucccaaagau ggaccccac ccacgaggaa caucguggaa    300
aaagaagacg uuccaaccac gucuucaaag caaguggauu gaugugaugg ucaacauggu    360
ggagcacgac acucucgucu acuccaagaa uaucaaagau acagucucag aagaccagag    420
ggcuauugag acuuuucaac aaaggguaau aucgggaaac cuccucggau uccauugccc    480
agcuaucugu cacuucaucg aaaggacagu agaaaaggaa gauggcuucu acaaaugcca    540
ucauugcgau aaaggaaagg cuaucguuca agaugccucu accgacagug gucccaaaga    600
uggaccccca cccacgagga acaucgugga aaaagaagac guuccaacca cgucuucaaa    660
gcaaguggau ugaugugaua ucuccacuga cguaagggau gacgcacaau cccacuaucc    720
uucgcaagac ccuuccucua uauaaggaag uucauuucau uuggagagga uaaaacauuu    780
caauccuuug aacgcgguag aacgugcuaa uuggauuuug gugagaacgc gguagaacgu    840
acuuaucacc uacaguuuua uuuuguuuuu cuuuuugguu uaaucuaucc agcuuaguac    900
cgaguggggg aaagugacug gugugccuaa aaccuuuucu uugauacuuu guaaaaauac    960
auacagauac aauggcgaac gguaacuuca aguugucuca auugcucaau guggacgaga   1020
ugucugcuga gcagaggagu cauuucuuug acuugaugcu gacuaaaccu gauugugaga   1080
ucgggcaaau gaugcaaaga guuguuguug auaaagucga ugacaugauu agagaaagaa   1140
agacuaaaga uccagugauu guucaugaag uucuuucuca gaaggaacag aacaaguuga   1200
uggaaauuua uccugaauuc aauaucgugu uuaaagacga caaaaacaug guucaugggu   1260
uugcggcugc ugagcgaaaa cuacaagcuu uauugcuuuu agauagaguu ccugcucugc   1320
aagaggugga ugacaucggu ggucaauggu cguuuugggu aacuagaggu gagaaaagga   1380
uucauuccug uuguccaaau cuagauauuc gggaugauca gagagaaauu ucucgacaga   1440
uauuucuuac ugcuauuggu gaucaagcua gaagugguaa gagacagaug ucggagaaug   1500
agcuguggau guaugaccaa uuucgugaaa auauugcugc gccuaacgcg guuaggugca   1560
auaaauacaua ucaggguugu acauguaggg guuuuucuga ugguaagaag aaaggcgcgc   1620
aguaugcgau agcucuucac agccuguaug acuucaaguu gaaagacuug auggcuacua   1680
ugguugagaa gaaaacuaaa gugguucaug cugcuaugcu uuuugcuccu gaaaguaugu   1740
uaguggacga agguccauua ccuucuguug acgguuacua caugaagaag aacgggaaga   1800
ucuauuucgg uuuugagaaa gauccuuccu uuucuuacau ucaugacugg gaagaguaca   1860
agaaguaucu acuggggaag ccagugaguu accaagggaa uguguucuac uucgaaccgu   1920
ggcaggugag aggagacaca augcuuuuuu cgaucuacag gauagcugga guuccgagga   1980
ggucucuauc aucgcaagag uacuaccgaa gaauauauau caguagaugg gaaaacaugg   2040
uuguuguccc aauuuucgau cugguucgaau caacgcgaga guuggucaag aaagaccugu   2100
uuguagagaa acaauucaug gacaaguguu uggauuacau agcuagguua ucugaccagc   2160
agcugaccau aagcaauguu aaaucauacu ugaguucaaa uaauugggguc uuauucauaa   2220
acggggcggc cgugaagaac aagcaaagug uagauucucg agauuuacag uuguuggcuc   2280
aaacuuugcu agugaaggaa caaguggcga gaccugucau gagggaguug cgugaagcaa   2340
uucugacuga gacgaaaccu aucacgucau ugacugaugu gcugggguuua auaucaagaa   2400
```

-continued

```
aacuguggaa gcaguuugcu aacaagaucg cagucggcgg auucguuggc augguuggua   2460
cucuaauugg auucuaucca aagaagguac uaaccugggc gaaggacaca ccaaaugguc   2520
cagaacuaug uuacgagaac ucgcacaaaa ccaaggugau aguauuucug aguguugugu   2580
augccauugg aggaaucacg cuuaugcguc gagacauccg agauggacug gugaaaaaac   2640
uaugugauau guuugauauc aaacgggggg cccaugucuu agacguugag aauccgugcc   2700
gcuauuauga aaucaacgau uucuuuagca gucuguauuc ggcaucugag uccggugaga   2760
ccguuuuacc agauuuaucc gagguaaaag ccaagucuga uaagcuauug cagcagaaga   2820
aagaaaucgc ugacgaguuu cuaagugcaa aauucucuaa cuauucuggc aguucgguga   2880
gaacuucucc accaucggug gucgguucau cucgaagcgg acugggucug uuguuggaag   2940
acaguaacgu gcugacccaa gcuagaguug gaguuucaag aaagguagac gaugaggaga   3000
ucauggagca guuucugagu ggucuuauug acacugaagc agaaauugac gagguuguuc   3060
cagccuuuuc agcugaaugu gaaagagggg aaacaagcgg uacaaaggug uuguguaaac   3120
cuuuaacgcc accaggauuu gagaacgugu ugccagcugu caaaccuuug gucagcaaag   3180
gaaaaacggu caaacguguc gauuacuucc aagugauggg aggugagaga uuaccaaaaa   3240
ggccgguugu caguggagac gauucugugg acgcuagaag agaguuucug uacuacuuag   3300
augcggagag agucgcucaa aaugaugaaa uuaugucucu guaucgugac uauucgagag   3360
gaguuauucg aacuggaggu cagaauuacc cgcacggacu gggagugugg gauguggaga   3420
ugaagaacug gugcauacgu ccagugguca cugaacaugc uuauguguuc caaccagaca   3480
aacguaugga ugauuggucg ggauacuuag aaguggcugu uugggaacga gguauguugg   3540
ucaacgacuu cgcggucgaa aggaugagug auuaugucau aguuugcgau cagacguauc   3600
uuugcaauaa cagguugauc uuggacaauu uaagugcccu ggaucuagga ccaguuaacu   3660
guucuuuuga auuaguugac gguguaccug guuguggauaa gucgacaaug auugucaacu   3720
cagcuaaucc uugugucgau gugguucucu cuacugggag agcagcaacc gacgacuuga   3780
ucgagagauu cgcgagcaaa gguuuuccau gcaaauugaa aaggagagug aagacgguug   3840
auucuuuuuu gaugcauugu guugaugguu cuuuaaccgg agacguguug cauuucgaug   3900
aagcucucau ggcccaugcu gguauggugu acuuuugcgc ucagauagcu ggugcuaaac   3960
gauguaucug ucaaggagau cagaaucaaa uuucuuucaa gccuagggua ucucaaguug   4020
auuugagguu uucuagucug gucggaaagu uugacauugu uacagaaaaa agagaaacuu   4080
acagaagucc agcagaugug gcugccguau ugaacaagua cuauacugga gaugucagaa   4140
cacauaacgc gacugcuaau ucgaugacgg ugaggaagau ugugucuaaa gaacagguuu   4200
cuuugaagcc uggugcucag uacauaacuu uccuucaguc ugagaagaag gaguugguaa   4260
auuuguuggc auugaggaaa guggcagcua aagugaguac aguacacgag ucgcaaggag   4320
agacauucaa agauguaguc cuagucagga cgaaaccuac ggaugacuca aucgcuagag   4380
gucgggagua cuuaaucgug gcguugucgc gucacacaca aucacuugug uaugaaacug   4440
ugaaagagga cgauguaagc aaagagauca gggaaagugc cgcgcuuacg aaggcggcuu   4500
uggcaagauu uuuuguuacu gagaccgucu uaugacgguu ucggucuagg uuugaugucu   4560
uuagacauca ugaagggccu ugcgccguuc cagauucagg uacgauuacg gacuuggaga   4620
ugugguacga cgcuuuguuu ccgggaaauu cguuaagaga cucaagccua gacggguauu   4680
ugguggcaac gacugauugc aauuugcgau uagacaaugu uacgaucaaa aguggaaacu   4740
ggaaagacaa guuugcugaa aaagaaacgu uucugaaacc gguuauucgu acugcuaugc   4800
```

-continued cugacaaaag gaagacuacu caguuggaga guuuguuagc auugcagaaa aggaaccaag 4860
cggcacccga ucuacaagaa aaugugcacg caacaguucu aaucgaagag acgaugaaga 4920
aguugaaauc uguugucuac gaugugggaa aaauucgggc ugauccuauu gucaauagag 4980
cucaaaugga gagauggugg agaaaucaaa gcacagcggu acaggcuaag guaguagcag 5040
augugagaga guuacaugaa auagacuauu cgucuuacau guauaugauc aaaucugacg 5100
ugaaaccuaa gacugauuua acaccgcaau uugaauacuc agcucuacag acuguugugu 5160
aucacgagaa guugaucaac ucguuguucg guccaauuuu caaagaaauu aaugaacgca 5220
aguuggaugc uaugcaacca cauuuugugu ucaacacgag aaugacaucg agugauuuaa 5280
acgaucgagu gaaguucuua aauacggaag cggcuuacga cuuuguugag auagacaugu 5340
cuaaauucga caagucggca aaucgcuucc auuuacaacu gcagcuggag auuuacaggu 5400
uauuugggcu agaugagugg gcggccuucc uuugggaggu gucgcacacu caaacuacug 5460
ugagagauau ucaaaauggu augauggcgc auauuuggua ccaacaaaag aguggagaug 5520
cugauacuua uaaugcaaau ucagauagaa cacugugugc acucuugucu gaauuaccau 5580
uggagaaagc agucaugguu acauauggag gagaugacuc acugauugcg uuuccuagag 5640
gaacgcaguu uguugauccg uguccaaagu uggcuacuaa guggaauuuc gagugcaaga 5700
uuuuuaagua cgaugucca auguuuugug ggaaguucuu gcuuaagacg ucaucguguu 5760
acgaguucgu gccagauccg guaaaaguuc ugacgaaguu ggggaaaaag aguauaaagg 5820
augugcaaca uuuagccgag aucuacaucu cgcugaauga uuccaauaga gcucuuggga 5880
acuacauggu gguauccaaa cuguccgagu cuguuucaga ccgguauuug uacaaaggug 5940
auucuguuca ugcgcuuugu gcgcuaugga agcauauuaa gaguuuuaca gcucugugua 6000
cauuauuccg agacgaaaac gauaaggaau ugaacccggc uaagguugau uggaagaagg 6060
cacagagagc ugugucaaac uuuuacgacu gguaauaugg aagacaaguc auuggucacc 6120
uugaagaaga agacuuucga agucucaaaa uucucaaauc uaggggccau ugaauuguuu 6180
guggacggua ggaggaagag accgaaguau uuucacagaa gaagagaaac uguccuaaau 6240
cauguuggug ggaagaagag ugaacacaag uuagacguuu uugaccaaag ggauuacaaa 6300
augauuaaau cuuacgcguu ucuaaagaua guagguguac aacuaguugu aacaucacau 6360
cuaccugcag auacgccugg guucauucaa aucgaucugu uggauucgag acuuacugag 6420
aaaagaaaga gaggaaagac uauucagaga uucaaagcuc gagcuugcga uaacuguuca 6480
guugcgcagu acaagguuga auacaguauu uccacacagg agaacguacu ugaugucugg 6540
aagguggguu guauuucuga gggcguuccg gucugugacg guacauaccc uuucaguauc 6600
gaagugucgc uaauaugggu ugcuacugau ucgacuaggc gccucaaugu ggaagaacug 6660
aacaguucgg auuacauuga aggcgauuuu accgaucaag agguuuucgg ugaguucaug 6720
ucuuugaaac aaguggagau gaagacgauu gaggcgaagu acgauggucc uuacagacca 6780
gcuacuacua gaccuaaguc auuauuguca agugaagaug uuaagagagc gucuaauaag 6840
aaaaacucgu cuuaaugcau aaagaaauuu auugucaaua ugacgugugu acucaagggu 6900
ugugugaaug aagucacugu ucuuggucac gagacgugua guaucgguca ugcuaacaaa 6960
uugcgaaagc aaguugcuga cauggguuggu gucacacgua ggugugcgga aaauaauugu 7020
ggaugguuug ucuguguugu uaucaaugau uuuacuuuug auguguauaa uuguuguggc 7080
cguagucacc uugaaaagug ucguaaacgu guugaaacaa gaaaucgaga aauuuggaaa 7140

-continued caaauucgac gaaaucaagc ugaaaacaug ucugcgacag cuaaaaaguc ucauaaaucg 7200
aagaccucua agaagaaauu caaagaggac agagaauuug ggacaccaaa aagauuuuua 7260
agagaugaug uuccuuucgg gauugaucgu uuguuugcuu uuugauuuua uuuuauauug 7320
uuaucuguuu cuguguauag acuguuugag auuggcgcuu ggccgacuca uugucuuacc 7380
auaggggaac ggacuuuguu uguguuguua uuuuauuugu auuuuauuaa aauucucaau 7440
gaucugaaaa ggccucgagg cuaagagauu auuggggggu gaguaaguac uuuuaaagug 7500
augaugguua caaaggcaaa aggguaaaa ccccucgccu acguaagcgu uauuacgccc 7560

<210> SEQ ID NO 26
<211> LENGTH: 2776
<212> TYPE: RNA
<213> ORGANISM: Artificial Sequence
<220> FEATURE:
<223> OTHER INFORMATION: Synthetic RNA2 of pTRV2 with C3 insert sequence

<400> SEQUENCE: 26
auaaaacauu gcaccuaugg uguugcccug gcuggggua gucagugauc gcaguagaau 60
guacuaauug acaaguugga gaauacggua gaacguccuu auccaacaca gccuuuaucc 120
cucucccuga cgagguuuuu gucaguguaa uauuucuuuu ugaacuaucc agcuuaguac 180
cguacgggaa agugacuggu gugcuuaucu uugaaauguu acuuuggguu ucgguucuuu 240
agguuaguaa gaaagcacuu gucuucucau acaaaggaaa accugagacg uaucgcuuac 300
gaaaguagca augaaagaaa gguggugguu uuaaucgcua ccgcaaaaac gaugggggucg 360 uuuuaauuaa cuucuccuac gcaagcgucu aaacggacgu uggguuuug cuaguuucuu 420 uagagaaaac uagcuaaguc uuuaauguua ucauuagaga uggcauaaau auaauacuug 480
ugucugcuga uaagaucauu uuaauuugga cgauuagacu uguugaacua cagguuacug 540
aaucacuugc gcuaaucaac augggagaua uguacgauga aucauuugac aagucgggcg 600
guccugcuga cuugauggac gauucuuggg uggaaucagu uucguggaaa gaucuguuga 660
agaaguuaca cagcauaaaa uuugcacuac agucugguag agaugagauc acuggguuac 720
uagcggcacu gaauagacag uguccuuauu caccauauga gcaguuucca gauaagaagg 780
uguauuuccu uuuagacuca cgggcuaaca gugcucuugg ugugauucag aacgcuucag 840
cguucaagag acgagcugau gagaagaaug caguggcggg uguuacaaau auuccugcga 900
auccaaacac aacgguuacg acgaaccaag ggaguacuac uacuaccaag gcgaacacug 960
gcucgacuuu ggaagaagac uuguacacuu auuacaaauu cgaugaugcc ucuacagcuu 1020
uccacaaauc ucuaacuucg uuagagaaca uggaguugaa gaguuauuac cgaaggaacu 1080
uugagaaagu auucgggauu aaguuuggug gagcagcugc uaguucaucu gcaccgccuc 1140
cagcgagugg agguccgaua cguccuaauc ccuagggauu uaaggacgug aacucuguug 1200
agaucucugu gaaauucaga ggguggguga uaccauauuc acugaugcca uuagcgacau 1260
cuaaauaggg cuaauuguga cuaauuugag ggaauuuccu uuaccauuga cgucagugc 1320 guugguagca uuugaguuuc gcaaugcacg aauuacuuag gaaguggcuu gacgacacua 1380
auguguuauu guuagauaau gguuuggugg ucaagguacg uaguagaguc ccacauauuc 1440
gcacguauga aguaauugga aaguugucag uuuuugauaa uucacuggga gaugauacgc 1500
uguuugaggg aaaaguagag aacguauuug uuuuuauguu caggcgguuc uuguguguca 1560
acaaagaugg acauuguuac ucaaggaagc acgaugagcu uuauuauuac ggacgagugg 1620
acuuagauuc ugugaguaau cugaccaggu cucaucgugu cgacggagga agugaagcac 1680

-continued agaaauggaa caaaaauaaa accuuggggu acucuuugau cuucuuugca agaauguaau 1740
gaauaucccu gauuacuuuc uucauauacc guccgucaag ugccuucaau ugcugaagcc 1800
aaauccuaaa ucccauacca caagauuaca ggcauagagu cucgaagcau uauuaauaac 1860
ucauuggcga ucaaauuaag augaauguca guuuauuaaa ggaaaaagua aagaacaaga 1920
acaaaaucau uuggcacuuu ucauacuaca accaucgaca aaauuagcug cugccacugc 1980
uucuuugaca uguaauacgg gagacucacu gcuauuucau uauuuggcuc aaggcaaagg 2040
aauuaggaga ugaaguggau ggauaugaug aaagcuccuc cgccaccacc uaaucaauac 2100
aauagcagca guaguacuaa uaaccuuagc caaagcaaag aaaucagaga agaagaagag 2160
cgaaaaagcu ugccuucuuc uccauacaau ccggccaaag uuucaauauc cggaucaugg 2220
acaccaauaa caauacuuau aggaucacua uacagcaaac gagaugcaau uuuagcuaag 2280
acagaaguuu cacaagcuca uuuagagcug uuaaagaaga cuaaugaagc agcaauagaa 2340
gaaacagaga agcaaucucg agcuccugag accugguccu caugucccga agacauuaaa 2400
cuacgguucu uuaaguagau ccgugucuga aguuuuaggu ucaauuuaaa ccuacgagau 2460
ugacauucuc gacugaucuu gauugaucgg uaagucuuuu guaauuuaau uuucuuuuug 2520
auuuuauuuu aaauuguuau cuguuucugu guauagacug uuugagaucg gcguuuggcc 2580
gacucauugu cuuaccauag gggaacggac uuuguuugug uuguuauuuu auuuguauuu 2640
uauuaaaauu cucaacgauc ugaaaaagcc ucgcggcuaa gagauuguug gggggugagu 2700
aaguacuuuu aaagugauga ugguuacaaa ggcaaaaggg guaaaacccc ucgccuacgu 2760
aagcguuauu acgccc 2776

<210> SEQ ID NO 27
<211> LENGTH: 1091
<212> TYPE: RNA
<213> ORGANISM: Artificial Sequence
<220> FEATURE:
<223> OTHER INFORMATION: Synthetic sequence consisting of SEQ_15 flanked by PEBV subgenomic promoters

<400> SEQUENCE: 27
gagcaucuug uucuggggguu ucacacuauc uuuagagaaa guguuaaguu aauuaaguua 60
ucuuaauuaa gagcauaauu auacugauuu gucucucguu gauagagucu aucauucugu 120
uacuaaaaau uugacaacuc gguuugcuga ccuacugguu acuguaucac uuacccgagu 180
uaacgaggga ggaagugaag cacagaaaug gaacaaaaau aaaaccuugg gguacucuuu 240
gaucuucuuu gcaagaaugu aaugaauauc ccugauuacu uucuucauau accguccguc 300
aagugccuuc aauugcugaa gccaaauccu aaaucccaua ccacaagauu acaggcauag 360
agucucgaag cauuauuaau aacucauugg cgaucaaauu aagaugaaug ucaguuuauu 420
aaaggaaaaa guaaagaaca agaacaaaau cauuuggcac uuuucauacu acaaccaucg 480
acaaaauuag cugcugccac ugcuucuuug acauguaaua cgggagacuc acugcuauuu 540
cauuauuugg cucaaggcaa aggaauuagg agaugaagug gauggauaug augaaagcuc 600
cuccgccacc accuaaucaa uacaauagca gcaguaguac uaauaaccuu agccaaagca 660
aagaaaucag agaagaagaa gagcgaaaaa gcuugccuuc uucuccauac aauccggcca 720
aaguuucaau auccggauca uggacaccaa uaacaauacu uauaggauca cuauacagca 780
aacgagaugc aauuuuagcu aagacagaag uuucacaagc ucauuuagag cuguuaaaga 840
agacuaauga agcagcaaua gaagaaacag agaagcaauc ucgagcuccu gagaccuggu 900

```
ccuccucguu aacucgggua agugauacag uaaccaguag gucagcaaac cgaguuguca    960

aauuuuuagu aacagaauga uagacucuau caacgagaga caaaucagua uaauuaugcu   1020

cuuaauuaag auaacuuaau uaacuuaaca cuuucucuaa agauagugug aaaccccaga   1080

acaagaugcu c                                                        1091


<210> SEQ ID NO 28
<211> LENGTH: 15791
<212> TYPE: DNA
<213> ORGANISM: Artificial Sequence
<220> FEATURE:
<223> OTHER INFORMATION: Synthetic pRNAi-GG sequence
<220> FEATURE:
<221> NAME/KEY: misc_feature
<222> LOCATION: (11788)..(11788)
<223> OTHER INFORMATION: n is a, c, g or t

<400> SEQUENCE: 28

aagctttcaa catgtggagc acgacacact tgtctactcc aaaaatatca aagatacagt     60

ctcagaagac caaagggcaa ttgagacttt tcaacaaagg gtaatatccg gaaacctcct    120

cggattccat tgcccagcta tctgtcactt tattgtgaag atagtggaaa aggaaggtgg    180

ctcctacaaa tgccatcatt gcgataaagg aaaggccatc gttgaagatg cctctgccga    240

cagtggtccc aaagatggac ccccacccac gaggagcatc gtggaaaaag aagacgttcc    300

aaccacgtct tcaaagcaag tggattgatg tgataacatg gtggagcacg acacacttgt    360

ctactccaaa aatatcaaag atacagtctc agaagaccaa agggcaattg agacttttca    420

acaaagggta atatccggaa acctcctcgg attccattgc ccagctatct gtcactttat    480

tgtgaagata gtggaaaagg aaggtggctc ctacaaatgc catcattgcg ataaaggaaa    540

ggccatcgtt gaagatgcct ctgccgacag tggtcccaaa gatggacccc cacccacgag    600

gagcatcgtg gaaaaagaag acgttccaac cacgtcttca aagcaagtgg attgatgtga    660

tatctccact gacgtaaggg atgacgcaca atcccactat ccttcgcaag acccttcctc    720

tatataagga agttcatttc atttggagag gacgtcgaga gttctcaaca caacatatac    780

aaaacaaacg aatctcaagc aatcaagcat tctacttcta ttgcagcaat ttaaatcatt    840

tcttttaaag caaaagcaat ttctgaaaa ttttcaccat ttacgaacga tagccagggc    900

ccggagtgag accaattctc gactaagttg gcagcatcac ccgacgcact ttgcgccgaa    960

taaatacctg tgacggaaga tcacttcgca gaataaataa atcctggtgt ccctgttgat   1020

accgggaagc cctgggccaa cttttggcga aaatgagacg ttgatcggca cgtaagaggt   1080

tccaactttc accataatga aataagatca ctaccgggcg tatttttga gttatcgaga   1140

ttttcaggag ctaaggaagc taaactttg ctgacgagaa cagggactgg tgaaatgcag   1200

tttaaggttt acacctataa aagagagagc cgttatcgtc tgtttgtgga tgtacagagt   1260

gatattattg acacgcctgg gcgacggatg gtgatccccc tggccagtgc acgtctgctg   1320

tcagataaag tctcccgtga actttacccg gtggtgcata tcggggatga aagctggcgc   1380

atgatgacca ccgatatggc cagtgtgccg gtatccgtta tcggggaaga agtggctgat   1440

ctcagccacc gcgaaaatga catcaaaaac gccattaacc tgatgttctg gggaatataa   1500

atgtcaggct cccttataca caggtcgacg gtctcaacga gcccttggta aggaaataat   1560

tattttcttt tttcctttta gtataaaata gttaagtgat gttaattagt atgattataa   1620

taatatagtt gttataattg tgaaaaaata atttataaat atattgttta cataaacaac   1680
```

-continued atagtaatgt aaaaaaatat gacaagtgat gtgtaagacg aagaagataa aagttgagag 1740
taagtatatt atttttaatg aatttgatcg aacatgtaag atgatatacg gccggtaaga 1800
ggttccaact ttcaccataa tgaaataaga tcactaccgg gcgtattttt tgagttatcg 1860
agattttcag gagctaagga agctaaaatg gagaaaaaaa tcactggata taccaccgtt 1920
gatatatccc aatggcatcg taaagaacat tttgaggcat ttcagtcagt tgctcaatgt 1980
acctataacc agaccgttca gctggatatt acggcctttt taaagaccgt aaagaaaaat 2040
aagcacaagt tttatccggc ctttattcac attcttgccc gcctgatgaa tgctcatccg 2100
gaattccgta tggcaatgaa agacggtgag ctggtgatat gggatagtgt tcacccttgt 2160
tacaccgttt tccatgagca aactgaaacg ttttcatcgc tctggagtga ataccacgac 2220
gatttccggc agtttctaca catatattcg caagatgtgg cgtgttacgg tgaaaacctg 2280
gcctatttcc ctaaagggtt tattgagaat atgtttttcg tctcagccaa tccctgggtg 2340
agtttcacca gttttgattt aaacgtggcc aatatggaca acttcttcgc ccccgttttc 2400
accatgggca aatattatac gcaaggcgac aaggtgctga tgccgctggc gattcaggtt 2460
catcatgccg tctgtgatgg cttccatgtc ggcagaatgc ttaatgaatt acaacagtac 2520
tgcgatgagt ggcagggcgg ggcgtaatcg cgtggatccg gcttactaaa agccagataa 2580
cagtatgcgt atttgcgcgc tgatttttgc ggtataagaa tatatactga tatgtcggtc 2640
ccataatagt aattctagct ggtttgatga attaaatatc aatgataaaa tactatagta 2700
aaaataagaa taaataaatt aaaataatat ttttttatga ttaatagttt attatataat 2760
taaatatcta taccattact aaatatttta gtttaaaagt taataaatat tttgttagaa 2820
attccaatct gcttgtaatt tatcaataaa caaaatatta aataacaagc taaagtaaca 2880
aataatatca aactaataga aacagtaatc taatgtaaca aaacataatc taatgctaat 2940
ataacaaagc gcaagatcta tcattttata tagtattatt ttcaatcaac attcttatta 3000
atttctaaat aatacttgta gttttattaa cttctaaatg gattgactat taattaaatg 3060
aattagtcga acatgaataa acaaggtaac atgatagatc atgtcattgt gttatcattg 3120
atcttacatt tggattgatt acagttggtc tagagatttc gtctagatcg ttgagaccaa 3180
ttctcgacta agttggcagc atcacccgac gcactttgcg ccgaataaat acctgtgacg 3240
gaagatcact tcgcagaata aataaatcct ggtgtccctg ttgataccgg gaagccctgg 3300
gccaactttt ggcgaaaatg agacgttgat cggcacgtaa gaggttccaa ctttcaccat 3360
aatgaaataa gatcactacc gggcgtattt tttgagttat cgagattttc aggagctaag 3420
gaagctaaac ttttgctgac gagaacaggg actggtgaaa tgcagtttaa ggtttacacc 3480
tataaaagag agagccgtta tcgtctgttt gtggatgtac agagtgatat tattgacacg 3540
cctgggcgac ggatggtgat ccccctggcc agtgcacgtc tgctgtcaga taaagtctcc 3600
cgtgaacttt acccggtggt gcatatcggg gatgaaagct ggcgcatgat gaccaccgat 3660
atggccagtg tgccggtatc cgttatcggg gaagaagtgg ctgatctcag ccaccgcgaa 3720
aatgacatca aaaacgccat taacctgatg ttctggggaa tataaatgtc aggctccctt 3780
atacacaggg tctcactccg agctcgaatt tccccgatcg ttcaaacatt tggcaataaa 3840
gtttcttaag attgaatcct gttgccggtc ttgcgatgat tatcatataa tttctgttga 3900
attacgttaa gcatgtaata attaacatgt aatgcatgac gttatttatg agatgggttt 3960
ttatgattag agtcccgcaa ttatacattt aatacgcgat agaaaacaaa atatagcgcg 4020
caaactagga taaattatcg cgcgcggtgt catctatgtt actagatcgg gaattcactg 4080

-continued

```
gccgtcgttt tacaacgtcg tgactgggaa aaccctggcg ttacccaact taatcgcctt   4140
gcagcacatc ccccttttcgc cagctggcgt aatagcgaag aggcccgcac cgatcgccct   4200
tcccaacagt tgcgcagcct gaatggcgcc cgctcctttc gctttcttcc cttcctttct   4260
cgccacgttc gccggctttc cccgtcaagc tctaaatcgg gggctccctt tagggttccg   4320
atttagtgct ttacggcacc tcgaccccaa aaaacttgat ttgggtgatg gttcacgtag   4380
tgggccatcg ccctgataga cggtmtcgcc ctttgacgtt ggagtccacg ttctttaata   4440
gtggactctt gttccaaact ggaacaacac tcaaccctat ctcgggctat tcttttgatt   4500
tataagggat tttgccgatt tcggaaccac catcaaacag gattttcgcc tgctggggca   4560
aaccagcgtg gaccgcttgc tgcaactctc tcagggccag gcggtgaagg gcaatcagct   4620
gttgcccgtc tcactggtga aaagaaaaac caccccagta cattaaaaac gtccgcaatg   4680
tgttattaag ttgtctaagc gtcaatttgt ttacaccaca atatatcctg ccaccagcca   4740
gccaacagct ccccgaccgg cagctcggca caaaatcacc actcgataca ggcagcccat   4800
cagtccggga cggcgtcagc gggagagccg ttgtaaggcg gcagactttg ctcatgttac   4860
cgatgctatt cggaagaacg gcaactaagc tgccgggttt gaaacacgga tgatctcgcg   4920
gagggtagca tgttgattgt aacgatgaca gagcgttgct gcctgtgatc aaatatcatc   4980
tccctcgcag agatccgaat tatcagcctt cttattcatt tctcgcttaa ccgtgacagg   5040
ctgtcgatct tgagaactat gccgacataa taggaaatcg ctggataaag ccgctgagga   5100
agctgagtgg cgctatttct ttagaagtga acgttgacga tatcaactcc cctatccatt   5160
gctcaccgaa tggtacaggt cggggacccg aagttccgac tgtcggcctg atgcatcccc   5220
ggctgatcga ccccagatct ggggctgaga aagcccagta aggaaacaac tgtaggttcg   5280
agtcgcgaga tcccccggaa ccaaaggaag taggttaaac ccgctccgat caggccgagc   5340
cacgccaggc cgagaacatt ggttcctgta ggcatcggga ttggcggatc aaacactaaa   5400
gctactggaa cgagcagaag tcctccggcc gccagttgcc aggcggtaaa ggtgagcaga   5460
ggcacgggag gttgccactt gcgggtcagc acggttccga acgccatgga aaccgccccc   5520
gccaggcccg ctgcgacgcc gacaggatct agcgctgcgt ttggtgtcaa caccaacagc   5580
gccacgcccg cagttccgca aatagccccc aggaccgcca tcaatcgtat cgggctacct   5640
agcagagcgg cagagatgaa cacgaccatc agcggctgca cagcgcctac cgtcgccgcg   5700
accccgcccg gcaggcggta gaccgaaata aacaacaagc tccagaatag cgaaatatta   5760
agtgcgccga ggatgaagat gcgcatccac cagattcccg ttggaatctg tcggacgatc   5820
atcacgagca ataaacccgc cggcaacgcc cgcagcagca taccggcgac ccctcggcct   5880
cgctgttcgg gctccacgaa aacgccggac agatgcgcct tgtgagcgtc cttggggccg   5940
tcctcctgtt tgaagaccga cagcccaatg atctcgccgt cgatgtaggc gccgaatgcc   6000
acggcatctc gcaaccgttc agcgaacgcc tccatgggct ttttctcctc gtgctcgtaa   6060
acggacccga acatctctgg agctttcttc agggccgaca atcggatctc gcggaaatcc   6120
tgcacgtcgg ccgctccaag ccgtcgaatc tgagccttaa tcacaattgt caattttaat   6180
cctctgttta tcggcagttc gtagagcgcg ccgtgcgtcc cgagcgatac tgagcgaagc   6240
aagtgcgtcg agcagtgccc gcttgttcct gaaatgccag taaagcgctg gctgctgaac   6300
ccccagccgg aactgacccc acaaggccct agcgtttgca atgcaccagg tcatcattga   6360
cccaggcgtg ttccaccagg ccgctgcctc gcaactcttc gcaggcttcg ccgacctgct   6420
```

-continued cgcgccactt cttcacgcgg gtggaatccg atccgcacat gaggcggaag gtttccagct 6480
tgagcgggta cggctcccgg tgcgagctga aatagtcgaa catccgtcgg gccgtcggcg 6540
acagcttgcg gtacttctcc catatgaatt tcgtgtagtg gtcgccagca aacagcacga 6600
cgatttcctc gtcgatcagg acctggcaac gggacgtttt cttgccacgg tccaggacgc 6660
ggaagcggtg cagcagcgac accgattcca ggtgcccaac gcggtcggac gtgaagccca 6720
tcgccgtcgc ctgtaggcgc gacaggcatt cctcggcctt cgtgtaatac cggccattga 6780
tcgaccagcc caggtcctgg caaagctcgt agaacgtgaa ggtgatcggc tcgccgatag 6840
gggtgcgctt cgcgtactcc aacacctgct gccacaccag ttcgtcatcg tcggcccgca 6900
gctcgacgcc ggtgtaggtg atcttcacgt ccttgttgac gtggaaaatg accttgtttt 6960
gcagcgcctc gcgcgggatt ttcttgttgc gcgtggtgaa cagggcagag cgggccgtgt 7020
cgtttggcat cgctcgcatc gtgtccggcc acggcgcaat atcgaacaag gaaagctgca 7080
tttccttgat ctgctgcttc gtgtgtttca gcaacgcggc ctgcttggcc tcgctgacct 7140
gttttgccag gtcctcgccg gcggtttttc gcttcttggt cgtcatagtt cctcgcgtgt 7200
cgatggtcat cgacttcgcc aaacctgccg cctcctgttc gagacgacgc gaacgctcca 7260
cggcggccga tggcgcgggc agggcagggg gagccagttg cacgctgtcg cgctcgatct 7320
tggccgtagc ttgctggacc atcgagccga cggactggaa ggtttcgcgg ggcgcacgca 7380
tgacggtgcg gcttgcgatg gtttcggcat cctcggcgga aaaccccgcg tcgatcagtt 7440
cttgcctgta tgccttccgg tcaaacgtcc gattcattca ccctccttgc gggattgccc 7500
cgactcacgc cggggcaatg tgcccttatt cctgatttga cccgcctggt gccttggtgt 7560
ccagataatc caccttatcg gcaatgaagt cggtcccgta gaccgtctgg ccgtccttct 7620
cgtacttggt attccgaatc ttgccctgca cgaataccag cgaccccttg cccaaatact 7680
tgccgtgggc ctcggcctga gagccaaaac acttgatgcg gaagaagtcg gtgcgctcct 7740
gcttgtcgcc ggcatcgttg cgccacatct aggtactaaa acaattcatc cagtaaaata 7800
taatatttta ttttctccca atcaggcttg atccccagta agtcaaaaaa tagctcgaca 7860
tactgttctt ccccgatatc ctccctgatc gaccggacgc agaaggcaat gtcataccac 7920
ttgtccgccc tgccgcttct cccaagatca ataaagccac ttactttgcc atctttcaca 7980
aagatgttgc tgtctcccag gtcgccgtgg gaaaagacaa gttcctcttc gggcttttcc 8040
gtctttaaaa aatcatacag ctcgcgcgga tctttaaatg gagtgtcttc ttcccagttt 8100
tcgcaatcca catcggccag atcgttattc agtaagtaat ccaattcggc taagcggctg 8160
tctaagctat tcgtataggg acaatccgat atgtcgatgg agtgaaagag cctgatgcac 8220
tccgcataca gctcgataat cttttcaggg ctttgttcat cttcatactc ttccgagcaa 8280
aggacgccat cggcctcact catgagcaga ttgctccagc catcatgccg ttcaaagtgc 8340
aggacctttg gaacaggcag ctttccttcc agccatagca tcatgtcctt ttcccgttcc 8400
acatcatagg tggtcccttt ataccggctg tccgtcattt ttaaatatag gttttcattt 8460
tctcccacca gcttatatac cttagcagga gacattcctt ccgtatcttt tacgcagcgg 8520
tatttttcga tcagtttttt caattccggt gatattctca ttttagccat ttattatttc 8580
cttcctcttt tctacagtat ttaaagatac cccaagaagc taattataac aagacgaact 8640
ccaattcact gttccttgca ttctaaaacc ttaaatacca gaaaacagct ttttcaaagt 8700
tgttttcaaa gttggcgtat aacatagtat cgacggagcc gattttgaaa ccacaattat 8760
gggtgatgct gccaacttac tgatttagtg tatgatggtg tttttgaggt gctccagtgg 8820
cttctgtgtc tatcagctgt ccctcctgtt cagctactga cggggtggtg cgtaacggca 8880
aaagcaccgc cggacatcag cgctatctct gctctcactg ccgtaaaaca tggcaactgc 8940
agttcactta caccgcttct caacccggta cgcaccagaa aatcattgat atggccatga 9000
atggcgttgg atgccgggca acagcccgca ttatgggcgt tggcctcaac acgattttac 9060
gtcacttaaa aaactcaggc cgcagtcggt aacctcgcgc atacagccgg gcagtgacgt 9120
catcgtctgc gcggaaatgg acgaacagtg gggctatgtc ggggctaaat cgcgccagcg 9180
ctggctgttt tacgcgtatg acagtctccg gaagacggtt gttgcgcacg tattcggtga 9240
acgcactatg gcgacgctgg ggcgtcttat gagcctgctg tcaccctttg acgtggtgat 9300
atggatgacg gatggctggc cgctgtatga atcccgcctg aagggaaagc tgcacgtaat 9360
cagcaagcga tatacgcagc gaattgagcg gcataacctg aatctgaggc agcacctggc 9420
acggctggga cggaagtcgc tgtcgttctc aaaatcggtg gagctgcatg acaaagtcat 9480
cgggcattat ctgaacataa aacactatca ataagttgga gtcattaccc aattatgata 9540
gaatttacaa gctataaggt tattgtcctg ggtttcaagc attagtccat gcaagttttt 9600
atgctttgcc cattctatag atatattgat aagcgcgctg cctatgcctt gccccctgaa 9660
atccttacat acggcgatat cttctatata aaagatatat tatcttatca gtattgtcaa 9720
tatattcaag gcaatctgcc tcctcatcct cttcatcctc ttcgtcttgg tagcttttta 9780
aatatggcgc ttcatagagt aattctgtaa aggtccaatt ctcgttttca tacctcggta 9840
taatcttacc tatcacctca aatggttcgc tgggtttatc gcacccccga acacgagcac 9900
ggcacccgcg accactatgc caagaatgcc caaggtaaaa attgccggcc ccgccatgaa 9960
gtccgtgaat gccccgacgg ccgaagtgaa gggcaggccg ccacccaggc cgccgccctc 10020
actgcccggc acctggtcgc tgaatgtcga tgccagcacc tgcggcacgt caatgcttcc 10080
gggcgtcgcg ctcgggctga tcgcccatcc cgttactgcc ccgatcccgg caatggcaag 10140
gactgccagc gctgccattt ttggggtgag gccgttcgcg gccgaggggc gcagcccctg 10200
gggggatggg aggcccgcgt tagcgggccg ggagggttcg agaagggggg gcaccccccct 10260 tcggcgtgcg cggtcacgcg cacagggcgc agccctggtt aaaaacaagg tttataaata 10320
ttggtttaaa agcaggttaa aagacaggtt agcggtggcc gaaaaacggg cggaaaccct 10380
tgcaaatgct ggattttctg cctgtggaca gcccctcaaa tgtcaatagg tgcgcccctc 10440
atctgtcagc actctgcccc tcaagtgtca aggatcgcgc ccctcatctg tcagtagtcg 10500
cgcccctcaa gtgtcaatac cgcagggcac ttatccccag gcttgtccac atcatctgtg 10560
ggaaactcgc gtaaaatcag gcgttttcgc cgatttgcga ggctggccag ctccacgtcg 10620
ccggccgaaa tcgagcctgc ccctcatctg tcaacgccgc gccgggtgag tcggcccctc 10680
aagtgtcaac gtccgcccct catctgtcag tgagggccaa gttttccgcg aggtatccac 10740
aacgccggcg gccgcggtgt ctcgcacacg gcttcgacgg cgtttctggc gcgtttgcag 10800
ggccatagac ggccgccagc ccagcggcga gggcaaccag cccggtgagc gtcgcaaagg 10860
cgctcggtct tgccttgctc gtcggtgatg tacttcacca gctccgcgaa gtcgctcttc 10920
ttgatggagc gcatggggac gtgcttggca atcacgcgca ccccccggcc gttttagcgg 10980
ctaaaaaagt catggctctg ccctcgggcg gaccacgccc atcatgacct tgccaagctc 11040
gtcctgcttc tcttcgatct tcgccagcag ggcgaggatc gtggcatcac cgaaccgcgc 11100
cgtgcgcggg tcgtcggtga gccagagttt cagcaggccg cccaggcggc ccaggtcgcc 11160
attgatgcgg gccagctcgc ggacgtgctc atagtccacg acgcccgtga ttttgtagcc 11220
ctggccgacg gccagcaggt aggccgacag gctcatgccg gccgccgccg ccttttcctc 11280
aatcgctctt cgttcgtctg gaaggcagta caccttgata ggtgggctgc ccttcctggt 11340
tggcttggtt tcatcagcca tccgcttgcc ctcatctgtt acgccggcgg tagccggcca 11400
gcctcgcaga gcaggattcc cgttgagcac cgccaggtgc gaataaggga cagtgaagaa 11460
ggaacacccg ctcgcgggtg ggcctacttc acctatcctg cccggctgac gccgttggat 11520
acaccaagga aagtctacac gaaccctttg gcaaaatcct gtatatcgtg cgaaaaagga 11580
tggatatacc gaaaaaatcg ctataatgac cccgaagcag ggttatgcag cggaaaagcg 11640
ccacgcttcc cgaagggaga aaggcggaca ggtatccggt aagcggcagg gtcggaacag 11700
gagagcgcac gagggagctt ccagggggaa acgcctggta tctttatagt cctgtcgggt 11760
ttcgccacct ctgacttgag cgtcgatntt gtgatgctcg tcaggggggc ggagcctatg 11820
gaaaaacgcc agcaacgcgg cctmtacggt tcctggcctt ttgctggcct tttgctcaca 11880
tgttctttcc tgcgttatcc cctgattctg tggataaccg tattaccgcc tttgagtgag 11940
ctgataccgc tcgccgcagc cgaacgaccg agcgcagcga gtcagtgagc gaggaagcgg 12000
aagagcgcca gaaggccgcc agagaggccg agcgcggccg tgaggcttgg acgctagggc 12060
agggcatgaa aaagcccgta gcgggctgct acgggcgtct gacgcggtgg aaagggggag 12120
gggatgttgt ctacatggct ctgctgtagt gagtgggttg cgctccggca gcggtcctga 12180
tcaatcgtca ccctttctcg gtccttcaac gttcctgaca acgagcctcc ttttcgccaa 12240
tccatcgaca atcaccgcga gtccctgctc gaacgctgcg tccggaccgg cttcgtcgaa 12300
ggcgtctatc gcggcccgca acagcggcga gagcggagcc tgttcaacgg tgccgccgcg 12360
ctcgccggca tcgctgtcgc cggcctgctc ctcaagcacg gccccaacag tgaagtagct 12420
gattgtcatc agcgcattga cggcgtcccc ggccgaaaaa cccgcctcgc agaggaagcg 12480
aagctgcgcg tcggccgttt ccatctgcgg tgcgcccggt cgcgtgccgg catggatgcg 12540
cgcgccatcg cggtaggcga gcagcgcctg cctgaagctg cgggcattcc cgatcagaaa 12600
tgagcgccag tcgtcgtcgg ctctcggcac cgaatgcgta tgattctccg ccagcatggc 12660
ttcggccagt gcgtcgagca gcgcccgctt gttcctgaag tgccagtaaa gcgccggctg 12720
ctgaaccccc aaccgttccg ccagtttgcg tgtcgtcaga ccgtctacgc cgacctcgtt 12780
caacaggtcc agggcggcac ggatcactgt attcggctgc aactttgtca tgcttgacac 12840
tttatcactg ataaacataa tatgtccacc aacttatcag tgataaagaa tccgcgcgtt 12900
caatcggacc agcggaggct ggtccggagg ccagacgtga aacccaacat accctgatc 12960
gtaattctga gcactgtcgc gctcgacgct gtcggcatcg gcctgattat gccggtgctg 13020
ccgggcctcc tgcgcgatct ggttcactcg aacgacgtca ccgcccacta tggcattctg 13080
ctggcgctgt atgcgttggt gcaatttgcc tgcgcacctg tgctgggcgc gctgtcggat 13140
cgtttcgggc ggcggccaat cttgctcgtc tcgctggccg gcgccagatc tggggaaccc 13200
tgtggttggc atgcacatac aaatggacga acggataaac cttttcacgc ccttttaaat 13260
atccgattat tctaataaac gctcttttct cttaggttta cccgccaata tatcctgtca 13320
aacactgata gtttaaactg aaggcgggaa acgacaatct gatcatgagc ggagaattaa 13380
gggagtcacg ttatgacccc cgccgatgac gcgggacaag ccgttttacg tttggaactg 13440
acagaaccgc aacgttgaag gagccactca gccgcgggtt tctggagttt aatgagctaa 13500
gcacatacgt cagaaaccat tattgcgcgt tcaaaagtcg cctaaggtca ctatcagcta 13560

-continued

```
gcaaatattt cttgtcaaaa atgctccact gacgttccat aaattcccct cggtatccaa  13620
ttagagtctc atattcactc tcaatccaaa taatctgcac cggatctgga tcgtttcgca  13680
tgattgaaca agatggattg cacgcaggtt ctccggccgc ttgggtggag aggctattcg  13740
gctatgactg ggcacaacag acaatcggct gctctgatgc cgccgtgttc cggctgtcag  13800
cgcaggggcg cccggttctt tttgtcaaga ccgacctgtc cggtgccctg aatgaactgc  13860
aggacgaggc agcgcggcta tcgtggctgg ccacgacggg cgttccttgc gcagctgtgc  13920
tcgacgttgt cactgaagcg ggaagggact ggctgctatt gggcgaagtg ccggggcagg  13980
atctcctgtc atctcacctt gctcctgccg agaaagtatc catcatggct gatgcaatgc  14040
ggcggctgca tacgcttgat ccggctacct gcccattcga ccaccaagcg aaacatcgca  14100
tcgagcgagc acgtactcgg atggaagccg gtcttgtcga tcaggatgat ctggacgaag  14160
agcatcaggg gctcgcgcca gccgaactgt tcgccaggct caaggcgcgc atgcccgacg  14220
gcgatgatct cgtcgtgacc catggcgatg cctgcttgcc gaatatcatg gtggaaaatg  14280
gccgcttttc tggattcatc gactgtggcc ggctgggtgt ggcggaccgc tatcaggaca  14340
tagcgttggc tacccgtgat attgctgaag agcttggcgg cgaatgggct gaccgcttcc  14400
tcgtgcttta cggtatcgcc gctcccgatt cgcagcgcat cgccttctat cgccttcttg  14460
acgagttctt ctgagcggga ctctggggtt cgaaatgacc gaccaagcga cgcccaacct  14520
gccatcacga gatttcgatt ccaccgccgc cttctatgaa aggttgggct tcggaatcgt  14580
tttccgggac gccggctgga tgatcctcca gcgcggggat ctcatgctgg agttcttcgc  14640
ccacgggatc tctgcggaac aggcggtcga aggtgccgat atcattacga cagcaacggc  14700
cgacaagcac aacgccacga tcctgagcga caatatgatc gggcccggcg tccacatcaa  14760
cggcgtcggc ggcgactgcc caggcaagac cgagatgcac cgcgatatct tgctgcgttc  14820
ggatattttc gtggagttcc cgccacagac ccggatgatc cccgatcgtt caaacatttg  14880
gcaataaagt ttcttaagat tgaatcctgt tgccggtctt gcgatgatta tcatataatt  14940
tctgttgaat tacgttaagc atgtaataat taacatgtaa tgcatgacgt tatttatgag  15000
atgggttttt atgattagag tcccgcaatt atacatttaa tacgcgatag aaaacaaaat  15060
atagcgcgca aactaggata aattatcgcg cgcggtgtca tctatgttac tagatcgggc  15120
ctcctgtcaa tgctggcggc ggctctggtg gtggttctgg tggcggctct gagggtggtg  15180
gctctgaggg tggcggttct gagggtggcg gctctgaggg aggcggttcc ggtggtggct  15240
ctggttccgg tgattttgat tatgaaaaga tggcaaacgc taataagggg gctatgaccg  15300
aaaatgccga tgaaaacgcg ctacagtctg acgctaaagg caaacttgat tctgtcgcta  15360
ctgattacgg tgctgctatc gatggtttca ttggtgacgt ttccggcctt gctaatggta  15420
atggtgctac tggtgatttt gctggctcta attcccaaat ggctcaagtc ggtgacggtg  15480
ataattcacc tttaatgaat aatttccgtc aatatttacc ttccctccct caatcggttg  15540
aatgtcgccc ttttgtcttt ggcccaatac gcaaaccgcc tctccccgcg cgttggccga  15600
ttcattaatg cagctggcac gacaggtttc ccgactggaa agcgggcagt gagcgcaacg  15660
caattaatgt gagttagctc actcattagg caccccaggc tttacacttt atgcttccgg  15720
ctcgtatgtt gtgtggaatt gtgagcggat aacaatttca cacaggaaac agctatgacc  15780
atgattacgc c                                                        15791
```

<210> SEQ ID NO 29

<211> LENGTH: 16178
<212> TYPE: DNA
<213> ORGANISM: Artificial Sequence
<220> FEATURE:
<223> OTHER INFORMATION: Synthetic pRNAi-GG with SEQ_14 inserts

<400> SEQUENCE: 29
aagctttcaa catgtggagc acgacacact tgtctactcc aaaaatatca aagatacagt 60
ctcagaagac caaagggcaa ttgagacttt tcaacaaagg gtaatatccg gaaacctcct 120
cggattccat tgcccagcta tctgtcactt tattgtgaag atagtggaaa aggaaggtgg 180
ctcctacaaa tgccatcatt gcgataaagg aaaggccatc gttgaagatg cctctgccga 240
cagtggtccc aaagatggac ccccacccac gaggagcatc gtggaaaaag aagacgttcc 300
aaccacgtct tcaaagcaag tggattgatg tgataacatg gtggagcacg acacacttgt 360
ctactccaaa aatatcaaag atacagtctc agaagaccaa agggcaattg agacttttca 420
acaaagggta atatccggaa acctcctcgg attccattgc ccagctatct gtcactttat 480
tgtgaagata gtggaaaagg aaggtggctc ctacaaatgc catcattgcg ataaaggaaa 540
ggccatcgtt gaagatgcct ctgccgacag tggtcccaaa gatggacccc cacccacgag 600
gagcatcgtg gaaaaagaag acgttccaac cacgtcttca aagcaagtgg attgatgtga 660
tatctccact gacgtaaggg atgacgcaca atcccactat ccttcgcaag acccttcctc 720
tatataagga agttcatttc atttggagag gacgtcgaga gttctcaaca caacatatac 780
aaaacaaacg aatctcaagc aatcaagcat tctacttcta ttgcagcaat ttaaatcatt 840
tcttttaaag caaaagcaat ttctgaaaa ttttcaccat ttacgaacga tagccagggc 900
ccggaggtgc aactcgctga tcattatcaa caaaatactc caattggcga tggccccgca 960
gagaggccgc ttcgtaaaat ctcaactgct ttcaaagaac tagcagccac cgtgagctcg 1020
ccgagtcctg aagtctccgt ggctcagttc tctcacgctt gctctctcgt ctcgcctctc 1080
tttggttgcc tcgggatcgc cttcaagata ttgaggcaaa ctgtgtaagg aaagctggta 1140
gtcatactag aaacctttg agggtagagc taatggttga tctcatgtcg acgctggagg 1200
atcgcctcca ctctcaaaga gagtggtggg agaagaagag aaactggagc tggaaagaag 1260
agataaaagc ttcagaagga agagcatcac caccaactct ggtgctcctg tatggaacaa 1320
caactcctcc atgaccgttg gacccagagg tccccacgcg cttaaaccaa accctaaatc 1380
tcacattcaa gaaaactgaa cctcacttgt gctgacttcc tcagagctcc aggtgttcaa 1440
actccggtca ttcctgtccg ctgcgccgag aaagttccta tccctaccaa atcctacact 1500
ggaataagaa caaatgtatc ctagaggagc aaccaatgtg cgttgtgcgt tatgtcacat 1560
tgtcaacatg gttcctcttc atcctaccct tacggtgcat catctgttaa atgcgctgtt 1620
tgccagtttg ttactaacgt taacaaaact taccottaaa tttatttgca ctactggaaa 1680
actacctgtt ccatggccaa cacttgtcac tactttctct tatgacgagc ccttggtaag 1740
gaaataatta ttttcttttt tccttttagt ataaaatagt taagtgatgt taattagtat 1800
gattataata atatagttgt tataattgtg aaaaaataat ttataaatat attgtttaca 1860
taaacaacat agtaatgtaa aaaaatatga caagtgatgt gtaagacgaa gaagataaaa 1920
gttgagagta agtatattat ttttaatgaa tttgatcgaa catgtaagat gatatacggc 1980
cggtaagagg ttccaacttt caccataatg aaataagatc actaccgggc gtattttttg 2040
agttatcgag attttcagga gctaaggaag ctaaaatgga gaaaaaaatc actggatata 2100
ccaccgttga tatatcccaa tggcatcgta aagaacattt tgaggcattt cagtcagttg 2160
ctcaatgtac ctataaccag accgttcagc tggatattac ggccttttta aagaccgtaa 2220
agaaaaataa gcacaagttt tatccggcct ttattcacat tcttgcccgc ctgatgaatg 2280
ctcatccgga attccgtatg gcaatgaaag acggtgagct ggtgatatgg gatagtgttc 2340
acccttgtta caccgttttc catgagcaaa ctgaaacgtt ttcatcgctc tggagtgaat 2400
accacgacga tttccggcag tttctacaca tatattcgca agatgtggcg tgttacggtg 2460
aaaacctggc ctatttccct aaagggttta ttgagaatat gtttttcgtc tcagccaatc 2520
cctgggtgag tttcaccagt tttgatttaa acgtggccaa tatggacaac ttcttcgccc 2580
ccgttttcac catgggcaaa tattatacgc aaggcgacaa ggtgctgatg ccgctggcga 2640
ttcaggttca tcatgccgtc tgtgatggct tccatgtcgg cagaatgctt aatgaattac 2700
aacagtactg cgatgagtgg cagggcgggg cgtaatcgcg tggatccggc ttactaaaag 2760
ccagataaca gtatgcgtat ttgcgcgctg atttttgcgg tataagaata tatactgata 2820
tgtcggtccc ataatagtaa ttctagctgg tttgatgaat taaatatcaa tgataaaata 2880
ctatagtaaa aataagaata aataaattaa aataatattt ttttatgatt aatagtttat 2940
tatataatta aatatctata ccattactaa atattttagt ttaaaagtta ataaatattt 3000
tgttagaaat tccaatctgc ttgtaattta tcaataaaca aaatattaaa taacaagcta 3060
aagtaacaaa taatatcaaa ctaatagaaa cagtaatcta atgtaacaaa acataatcta 3120
atgctaatat aacaaagcgc aagatctatc attttatata gtattatttt caatcaacat 3180
tcttattaat ttctaaataa tacttgtagt tttattaact tctaaatgga ttgactatta 3240
attaaatgaa ttagtcgaac atgaataaac aaggtaacat gatagatcat gtcattgtgt 3300
tatcattgat cttacatttg gattgattac agttggtcta gagatttcgt ctagatcgtc 3360
ataagagaaa gtagtgacaa gtgttggcca tggaacaggt agttttccag tagtgcaaat 3420
aaatttaagg gtaagttttg ttaacgttag taacaaactg gcaaacagcg catttaacag 3480
atgatgcacc gtaagggtag gatgaagagg aaccatgttg acaatgtgac ataacgcaca 3540
acgcacattg gttgctcctc taggatacat ttgttcttat tccagtgtag gatttggtag 3600
ggataggaac tttctcggcg cagcggacag gaatgaccgg agtttgaaca cctggagctc 3660
tgaggaagtc agcacaagtg aggttcagtt ttcttgaatg tgagatttag ggtttggttt 3720
aagcgcgtgg ggacctctgg gtccaacggt catggaggag ttgttgttcc atacaggagc 3780
accagagttg gtggtgatgc tcttccttct gaagctttta tctcttcttt ccagctccag 3840
tttctcttct tctcccacca ctctctttga gagtggaggc gatcctccag cgtcgacatg 3900
agatcaacca ttagctctac cctcaaaagg tttctagtat gactaccagc tttccttaca 3960
cagtttgcct caatatcttg aaggcgatcc cgaggcaacc aaagagaggc gagacgagag 4020
agcaagcgtg agagaactga gccacggaga cttcaggact cggcgagctc acggtggctg 4080
ctagttcttt gaaagcagtt gagattttac gaagcggcct ctctgcgggg ccatcgccaa 4140
ttggagtatt ttgttgataa tgatcagcga gttgcacctc cgagctcgaa tttccccgat 4200
cgttcaaaca tttggcaata aagtttctta agattgaatc ctgttgccgg tcttgcgatg 4260
attatcatat aatttctgtt gaattacgtt aagcatgtaa taattaacat gtaatgcatg 4320
acgttattta tgagatgggt ttttatgatt agagtcccgc aattatacat ttaatacgcg 4380
atagaaaaca aaatatagcg cgcaaactag gataaattat cgcgcgcggt gtcatctatg 4440
ttactagatc gggaattcac tggccgtcgt tttacaacgt cgtgactggg aaaaccctgg 4500

-continued

```
cgttacccaa cttaatcgcc ttgcagcaca tccccctttc gccagctggc gtaatagcga   4560
agaggcccgc accgatcgcc cttcccaaca gttgcgcagc ctgaatggcg cccgctcctt   4620
tcgctttctt cccttccttt ctcgccacgt tcgccggctt tccccgtcaa gctctaaatc   4680
gggggctccc tttagggttc cgatttagtg ctttacggca cctcgacccc aaaaaacttg   4740
atttgggtga tggttcacgt agtgggccat cgccctgata gacggttttt cgccctttga   4800
cgttggagtc cacgttcttt aatagtggac tcttgttcca aactggaaca acactcaacc   4860
ctatctcggg ctattctttt gatttataag ggattttgcc gatttcggaa ccaccatcaa   4920
acaggatttt cgcctgctgg ggcaaaccag cgtggaccgc ttgctgcaac tctctcaggg   4980
ccaggcggtg aagggcaatc agctgttgcc cgtctcactg gtgaaaagaa aaaccacccc   5040
agtacattaa aaacgtccgc aatgtgttat taagttgtct aagcgtcaat ttgtttacac   5100
cacaatatat cctgccacca gccagccaac agctccccga ccggcagctc ggcacaaaat   5160
caccactcga tacaggcagc ccatcagtcc gggacggcgt cagcgggaga gccgttgtaa   5220
ggcggcagac tttgctcatg ttaccgatgc tattcggaag aacggcaact aagctgccgg   5280
gtttgaaaca cggatgatct cgcggagggt agcatgttga ttgtaacgat gacagagcgt   5340
tgctgcctgt gatcaaatat catctccctc gcagagatcc gaattatcag ccttcttatt   5400
catttctcgc ttaaccgtga caggctgtcg atcttgagaa ctatgccgac ataataggaa   5460
atcgctggat aaagccgctg aggaagctga gtggcgctat ttctttagaa gtgaacgttg   5520
acgatatcaa ctcccctatc cattgctcac cgaatggtac aggtcgggga cccgaagttc   5580
cgactgtcgg cctgatgcat ccccggctga tcgaccccag atctggggct gagaaagccc   5640
agtaaggaaa caactgtagg ttcgagtcgc gagatccccc ggaaccaaag gaagtaggtt   5700
aaacccgctc cgatcaggcc gagccacgcc aggccgagaa cattggttcc tgtaggcatc   5760
gggattggcg gatcaaacac taaagctact ggaacgagca gaagtcctcc ggccgccagt   5820
tgccaggcgg taaaggtgag cagaggcacg ggaggttgcc acttgcgggt cagcacggtt   5880
ccgaacgcca tggaaaccgc cccgccaggc cccgctgcga cgccgacagg atctagcgct   5940
gcgtttggtg tcaacaccaa cagcgccacg cccgcagttc cgcaaatagc ccccaggacc   6000
gccatcaatc gtatcgggct acctagcaga gcggcagaga tgaacacgac catcagcggc   6060
tgcacagcgc ctaccgtcgc cgcgaccccg cccggcaggc ggtagaccga aataaacaac   6120
aagctccaga atagcgaaat attaagtgcg ccgaggatga agatgcgcat ccaccagatt   6180
cccgttggaa tctgtcggac gatcatcacg agcaataaac ccgccggcaa cgcccgcagc   6240
agcataccgg cgacccctcg gcctcgctgt tcgggctcca cgaaaacgcc ggacagatgc   6300
gccttgtgag cgtccttggg gccgtcctcc tgtttgaaga ccgacagccc aatgatctcg   6360
ccgtcgatgt aggcgccgaa tgccacggca tctcgcaacc gttcagcgaa cgcctccatg   6420
ggctttttct cctcgtgctc gtaaacggac ccgaacatct ctggagcttt cttcagggcc   6480
gacaatcgga tctcgcggaa atcctgcacg tcggccgctc caagccgtcg aatctgagcc   6540
ttaatcacaa ttgtcaattt taatcctctg tttatcggca gttcgtagag cgcgccgtgc   6600
gtcccgagcg atactgagcg aagcaagtgc gtcgagcagt gcccgcttgt tcctgaaatg   6660
ccagtaaagc gctggctgct gaacccccag ccggaactga ccccacaagg ccctagcgtt   6720
tgcaatgcac caggtcatca ttgacccagg cgtgttccac caggccgctg cctcgcaact   6780
cttcgcaggc ttcgccgacc tgctcgcgcc acttcttcac gcgggtggaa tccgatccgc   6840
acatgaggcg gaaggtttcc agcttgagcg ggtacggctc ccggtgcgag ctgaaatagt   6900
```

-continued

```
cgaacatccg tcgggccgtc ggcgacagct tgcggtactt ctcccatatg aatttcgtgt   6960
agtggtcgcc agcaaacagc acgacgattt cctcgtcgat caggacctgg caacgggacg   7020
ttttcttgcc acggtccagg acgcggaagc ggtgcagcag cgacaccgat tccaggtgcc   7080
caacgcggtc ggacgtgaag cccatcgccg tcgcctgtag gcgcgacagg cattcctcgg   7140
ccttcgtgta ataccggcca ttgatcgacc agcccaggtc ctggcaaagc tcgtagaacg   7200
tgaaggtgat cggctcgccg ataggggtgc gcttcgcgta ctccaacacc tgctgccaca   7260
ccagttcgtc atcgtcggcc cgcagctcga cgccggtgta ggtgatcttc acgtccttgt   7320
tgacgtggaa aatgaccttg ttttgcagcg cctcgcgcgg gattttcttg ttgcgcgtgg   7380
tgaacagggc agagcgggcc gtgtcgtttg gcatcgctcg catcgtgtcc ggccacggcg   7440
caatatcgaa caaggaaagc tgcatttcct tgatctgctg cttcgtgtgt ttcagcaacg   7500
cggcctgctt ggcctcgctg acctgttttg ccaggtcctc gccggcggtt tttcgcttct   7560
tggtcgtcat agttcctcgc gtgtcgatgg tcatcgactt cgccaaacct gccgcctcct   7620
gttcgagacg acgcgaacgc tccacggcgg ccgatggcgc gggcagggca gggggagcca   7680
gttgcacgct gtcgcgctcg atcttggccg tagcttgctg gaccatcgag ccgacggact   7740
ggaaggtttc gcggggcgca cgcatgacgg tgcggcttgc gatggtttcg gcatcctcgg   7800
cggaaaaccc cgcgtcgatc agttcttgcc tgtatgcctt ccggtcaaac gtccgattca   7860
ttcaccctcc ttgcgggatt gccccgactc acgccggggc aatgtgccct tattcctgat   7920
ttgacccgcc tggtgccttg gtgtccagat aatccacctt atcggcaatg aagtcggtcc   7980
cgtagaccgt ctggccgtcc ttctcgtact tggtattccg aatcttgccc tgcacgaata   8040
ccagcgaccc cttgcccaaa tacttgccgt gggcctcggc ctgagagcca aaacacttga   8100
tgcggaagaa gtcggtgcgc tcctgcttgt cgccggcatc gttgcgccac atctaggtac   8160
taaaacaatt catccagtaa aatataatat tttattttct cccaatcagg cttgatcccc   8220
agtaagtcaa aaaatagctc gacatactgt tcttccccga tatcctccct gatcgaccgg   8280
acgcagaagg caatgtcata ccacttgtcc gccctgccgc ttctcccaag atcaataaag   8340
ccacttactt tgccatcttt cacaaagatg ttgctgtctc ccaggtcgcc gtgggaaaag   8400
acaagttcct cttcgggctt ttccgtcttt aaaaaatcat acagctcgcg cggatcttta   8460
aatggagtgt cttcttccca gttttcgcaa tccacatcgg ccagatcgtt attcagtaag   8520
taatccaatt cggctaagcg gctgtctaag ctattcgtat agggacaatc cgatatgtcg   8580
atggagtgaa agagcctgat gcactccgca tacagctcga taatcttttc agggctttgt   8640
tcatcttcat actcttccga gcaaaggacg ccatcggcct cactcatgag cagattgctc   8700
cagccatcat gccgttcaaa gtgcaggacc tttggaacag gcagctttcc ttccagccat   8760
agcatcatgt ccttttcccg ttccacatca taggtggtcc ctttataccg gctgtccgtc   8820
atttttaaat ataggttttc attttctccc accagcttat ataccttagc aggagacatt   8880
ccttccgtat cttttacgca gcggtatttt tcgatcagtt ttttcaattc cggtgatatt   8940
ctcattttag ccatttatta tttccttcct cttttctaca gtatttaaag ataccccaag   9000
aagctaatta taacaagacg aactccaatt cactgttcct tgcattctaa aaccttaaat   9060
accagaaaac agctttttca aagttgtttt caaagttggc gtataacata gtatcgacgg   9120
agccgatttt gaaaccacaa ttatgggtga tgctgccaac ttactgattt agtgtatgat   9180
ggtgtttttg aggtgctcca gtggcttctg tgtctatcag ctgtccctcc tgttcagcta   9240
```

-continued

```
ctgacggggt ggtgcgtaac ggcaaaagca ccgccggaca tcagcgctat ctctgctctc   9300
actgccgtaa aacatggcaa ctgcagttca cttacaccgc ttctcaaccc ggtacgcacc   9360
agaaaatcat tgatatggcc atgaatggcg ttggatgccg ggcaacagcc cgcattatgg   9420
gcgttggcct caacacgatt ttacgtcact taaaaaactc aggccgcagt cggtaacctc   9480
gcgcatacag ccgggcagtg acgtcatcgt ctgcgcggaa atggacgaac agtggggcta   9540
tgtcggggct aaatcgcgcc agcgctggct gttttacgcg tatgacagtc tccggaagac   9600
ggttgttgcg cacgtattcg gtgaacgcac tatggcgacg ctggggcgtc ttatgagcct   9660
gctgtcaccc tttgacgtgg tgatatggat gacggatggc tggccgctgt atgaatcccg   9720
cctgaaggga aagctgcacg taatcagcaa gcgatatacg cagcgaattg agcggcataa   9780
cctgaatctg aggcagcacc tggcacggct gggacggaag tcgctgtcgt tctcaaaatc   9840
ggtggagctg catgacaaag tcatcgggca ttatctgaac ataaaacact atcaataagt   9900
tggagtcatt acccaattat gatagaattt acaagctata aggttattgt cctgggtttc   9960
aagcattagt ccatgcaagt ttttatgctt tgcccattct atagatatat tgataagcgc  10020
gctgcctatg ccttgccccc tgaaatcctt acatacggcg atatcttcta tataaaagat  10080
atattatctt atcagtattg tcaatatatt caaggcaatc tgcctcctca tcctcttcat  10140
cctcttcgtc ttggtagctt tttaaatatg gcgcttcata gagtaattct gtaaaggtcc  10200
aattctcgtt ttcatacctc ggtataatct tacctatcac ctcaaatggt tcgctgggtt  10260
tatcgcaccc ccgaacacga gcacggcacc cgcgaccact atgccaagaa tgcccaaggt  10320
aaaaattgcc ggccccgcca tgaagtccgt gaatgccccg acggccgaag tgaagggcag  10380
gccgccaccc aggccgccgc cctcactgcc cggcacctgg tcgctgaatg tcgatgccag  10440
cacctgcggc acgtcaatgc ttccgggcgt cgcgctcggg ctgatcgccc atcccgttac  10500
tgccccgatc ccggcaatgg caaggactgc cagcgctgcc atttttgggg tgaggccgtt  10560
cgcggccgag ggcgcagccc cctgggggga tgggaggccc gcgttagcgg gccgggaggg  10620
ttcgagaagg gggggcaccc cccttcggcg tgcgcggtca cgcgcacagg gcgcagccct  10680
ggttaaaaac aaggtttata aatattggtt taaaagcagg ttaaaagaca ggttagcggt  10740
ggccgaaaaa cgggcggaaa cccttgcaaa tgctggattt tctgcctgtg gacagcccct  10800
caaatgtcaa taggtgcgcc cctcatctgt cagcactctg cccctcaagt gtcaaggatc  10860
gcgcccctca tctgtcagta gtcgcgcccc tcaagtgtca ataccgcagg gcacttatcc  10920
ccaggcttgt ccacatcatc tgtgggaaac tcgcgtaaaa tcaggcgttt tcgccgattt  10980
gcgaggctgg ccagctccac gtcgccggcc gaaatcgagc ctgcccctca tctgtcaacg  11040
ccgcgccggg tgagtcggcc cctcaagtgt caacgtccgc ccctcatctg tcagtgaggg  11100
ccaagttttc cgcgaggtat ccacaacgcc ggcggccgcg gtgtctcgca cacggcttcg  11160
acggcgtttc tggcgcgttt gcagggccat agacggccgc cagcccagcg gcgagggcaa  11220
ccagcccggt gagcgtcgca aaggcgctcg gtcttgcctt gctcgtcggt gatgtacttc  11280
accagctccg cgaagtcgct cttcttgatg gagcgcatgg ggacgtgctt ggcaatcacg  11340
cgcacccccc ggccgtttta gcggctaaaa aagtcatggc tctgccctcg ggcggaccac  11400
gcccatcatg accttgccaa gctcgtcctg cttctcttcg atcttcgcca gcagggcgag  11460
gatcgtggca tcaccgaacc gcgccgtgcg cgggtcgtcg gtgagccaga gtttcagcag  11520
gccgcccagg cggcccaggt cgccattgat gcgggccagc tcgcggacgt gctcatagtc  11580
cacgacgccc gtgattttgt agccctggcc gacggccagc aggtaggccg acaggctcat  11640
```

gccggccgcc gccgcctttt cctcaatcgc tcttcgttcg tctggaaggc agtacacctt 11700
gataggtggg ctgcccttcc tggttggctt ggtttcatca gccatccgct tgccctcatc 11760
tgttacgccg gcggtagccg gccagcctcg cagagcagga ttcccgttga gcaccgccag 11820
gtgcgaataa gggacagtga agaaggaaca cccgctcgcg ggtgggccta cttcacctat 11880
cctgcccggc tgacgccgtt ggatacacca aggaaagtct acacgaaccc tttggcaaaa 11940
tcctgtatat cgtgcgaaaa aggatggata taccgaaaaa atcgctataa tgaccccgaa 12000
gcagggttat gcagcggaaa agcgccacgc ttcccgaagg gagaaaggcg gacaggtatc 12060
cggtaagcgg cagggtcgga acaggagagc gcacgaggga gcttccaggg ggaaacgcct 12120
ggtatcttta tagtcctgtc gggtttcgcc acctctgact tgagcgtcga tttttgtgat 12180
gctcgtcagg ggggcggagc ctatggaaaa acgccagcaa cgcggccttt ttacggttcc 12240
tggccttttg ctggcctttt gctcacatgt tctttcctgc gttatcccct gattctgtgg 12300
ataaccgtat taccgccttt gagtgagctg ataccgctcg ccgcagccga acgaccgagc 12360
gcagcgagtc agtgagcgag gaagcggaag agcgccagaa ggccgccaga gaggccgagc 12420
gcggccgtga ggcttggacg ctagggcagg gcatgaaaaa gcccgtagcg ggctgctacg 12480
ggcgtctgac gcggtggaaa gggggagggg atgttgtcta catggctctg ctgtagtgag 12540
tgggttgcgc tccggcagcg gtcctgatca atcgtcaccc tttctcggtc cttcaacgtt 12600
cctgacaacg agcctccttt tcgccaatcc atcgacaatc accgcgagtc cctgctcgaa 12660
cgctgcgtcc ggaccggctt cgtcgaaggc gtctatcgcg gcccgcaaca gcggcgagag 12720
cggagcctgt tcaacggtgc cgccgcgctc gccggcatcg ctgtcgccgg cctgctcctc 12780
aagcacggcc ccaacagtga agtagctgat tgtcatcagc gcattgacgg cgtccccggc 12840
cgaaaaaccc gcctcgcaga ggaagcgaag ctgcgcgtcg gccgtttcca tctgcggtgc 12900
gcccggtcgc gtgccggcat ggatgcgcgc gccatcgcgg taggcgagca gcgcctgcct 12960
gaagctgcgg gcattcccga tcagaaatga gcgccagtcg tcgtcggctc tcggcaccga 13020
atgcgtatga ttctccgcca gcatggcttc ggccagtgcg tcgagcagcg cccgcttgtt 13080
cctgaagtgc cagtaaagcg ccggctgctg aacccccaac cgttccgcca gtttgcgtgt 13140
cgtcagaccg tctacgccga cctcgttcaa caggtccagg gcggcacgga tcactgtatt 13200
cggctgcaac tttgtcatgc ttgacacttt atcactgata aacataatat gtccaccaac 13260
ttatcagtga taaagaatcc gcgcgttcaa tcggaccagc ggaggctggt ccggaggcca 13320
gacgtgaaac ccaacatacc cctgatcgta attctgagca ctgtcgcgct cgacgctgtc 13380
ggcatcggcc tgattatgcc ggtgctgccg ggcctcctgc gcgatctggt tcactcgaac 13440
gacgtcaccg cccactatgg cattctgctg gcgctgtatg cgttggtgca atttgcctgc 13500
gcacctgtgc tgggcgcgct gtcggatcgt ttcgggcggc ggccaatctt gctcgtctcg 13560
ctggccggcg ccagatctgg ggaaccctgt ggttggcatg cacatacaaa tggacgaacg 13620
gataaacctt ttcacgccct tttaaatatc cgattattct aataaacgct cttttctctt 13680
aggtttaccc gccaatatat cctgtcaaac actgatagtt taaactgaag gcgggaaacg 13740
acaatctgat catgagcgga gaattaaggg agtcacgtta tgacccccgc cgatgacgcg 13800
ggacaagccg ttttacgttt ggaactgaca gaaccgcaac gttgaaggag ccactcagcc 13860
gcgggtttct ggagtttaat gagctaagca catacgtcag aaaccattat tgcgcgttca 13920
aaagtcgcct aaggtcacta tcagctagca aatatttctt gtcaaaaatg ctccactgac 13980

-continued

```
gttccataaa ttcccctcgg tatccaatta gagtctcata ttcactctca atccaaataa  14040
tctgcaccgg atctggatcg tttcgcatga ttgaacaaga tggattgcac gcaggttctc  14100
cggccgcttg ggtggagagg ctattcggct atgactgggc acaacagaca atcggctgct  14160
ctgatgccgc cgtgttccgg ctgtcagcgc aggggcgccc ggttcttttt gtcaagaccg  14220
acctgtccgg tgccctgaat gaactgcagg acgaggcagc gcggctatcg tggctggcca  14280
cgacgggcgt tccttgcgca gctgtgctcg acgttgtcac tgaagcggga agggactggc  14340
tgctattggg cgaagtgccg gggcaggatc tcctgtcatc tcaccttgct cctgccgaga  14400
aagtatccat catggctgat gcaatgcggc ggctgcatac gcttgatccg gctacctgcc  14460
cattcgacca ccaagcgaaa catcgcatcg agcgagcacg tactcggatg gaagccggtc  14520
ttgtcgatca ggatgatctg gacgaagagc atcaggggct cgcgccagcc gaactgttcg  14580
ccaggctcaa ggcgcgcatg cccgacggcg atgatctcgt cgtgacccat ggcgatgcct  14640
gcttgccgaa tatcatggtg gaaaatggcc gcttttctgg attcatcgac tgtggccggc  14700
tgggtgtggc ggaccgctat caggacatag cgttggctac ccgtgatatt gctgaagagc  14760
ttggcggcga atgggctgac cgcttcctcg tgctttacgg tatcgccgct cccgattcgc  14820
agcgcatcgc cttctatcgc cttcttgacg agttcttctg agcgggactc tggggttcga  14880
aatgaccgac caagcgacgc ccaacctgcc atcacgagat ttcgattcca ccgccgcctt  14940
ctatgaaagg ttgggcttcg gaatcgtttt ccgggacgcc ggctggatga tcctccagcg  15000
cggggatctc atgctggagt tcttcgccca cgggatctct gcggaacagg cggtcgaagg  15060
tgccgatatc attacgacag caacggccga caagcacaac gccacgatcc tgagcgacaa  15120
tatgatcggg cccggcgtcc acatcaacgg cgtcggcggc gactgcccag gcaagaccga  15180
gatgcaccgc gatatcttgc tgcgttcgga tattttcgtg gagttcccgc cacagacccg  15240
gatgatcccc gatcgttcaa acatttggca ataaagtttc ttaagattga atcctgttgc  15300
cggtcttgcg atgattatca tataatttct gttgaattac gttaagcatg taataattaa  15360
catgtaatgc atgacgttat ttatgagatg ggtttttatg attagagtcc cgcaattata  15420
catttaatac gcgatagaaa acaaaatata gcgcgcaaac taggataaat tatcgcgcgc  15480
ggtgtcatct atgttactag atcgggcctc ctgtcaatgc tggcggcggc tctggtggtg  15540
gttctggtgg cggctctgag ggtggtggct ctgagggtgg cggttctgag ggtggcggct  15600
ctgagggagg cggttccggt ggtggctctg gttccggtga ttttgattat gaaaagatgg  15660
caaacgctaa taagggggct atgaccgaaa atgccgatga aaacgcgcta cagtctgacg  15720
ctaaaggcaa acttgattct gtcgctactg attacggtgc tgctatcgat ggtttcattg  15780
gtgacgtttc cggccttgct aatggtaatg gtgctactgg tgattttgct ggctctaatt  15840
cccaaatggc tcaagtcggt gacggtgata attcaccttt aatgaataat ttccgtcaat  15900
atttaccttc cctccctcaa tcggttgaat gtcgcccttt tgtctttggc ccaatacgca  15960
aaccgcctct ccccgcgcgt tggccgattc attaatgcag ctggcacgac aggtttcccg  16020
actggaaagc gggcagtgag cgcaacgcaa ttaatgtgag ttagctcact cattaggcac  16080
cccaggcttt acactttatg cttccggctc gtatgttgtg tggaattgtg agcggataac  16140
aatttcacac aggaaacagc tatgaccatg attacgcc                          16178
```

<210> SEQ ID NO 30
<211> LENGTH: 508
<212> TYPE: DNA
<213> ORGANISM: Artificial Sequence
<220> FEATURE:
<223> OTHER INFORMATION: Human cytomegalovirus immediate early enhancer and promoter sequence. This is used to drive transcription of RNAi herbicide components in eukaryotic platforms

<400> SEQUENCE: 30
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagct 508

<210> SEQ ID NO 31
<211> LENGTH: 615
<212> TYPE: RNA
<213> ORGANISM: Artificial Sequence
<220> FEATURE:
<223> OTHER INFORMATION: Synthetic TRV coat protein CDS DNA from pTRV2 sequence

<400> SEQUENCE: 31
augggagaua uguacgauga aucauuugac aagucgggcg guccugcuga cuugauggac 60
gauucuuggg uggaaucagu uucguggaaa gaucuguuga agaaguuaca cagcauaaaa 120
uuugcacuac agucugguag agaugagauc acuggguuac uagcggcacu gaauagacag 180
uguccuuauu caccauauga gcaguuucca gauaagaagg uguauuuccu uuuagacuca 240
cgggcuaaca gugcucuugg ugugauucag aacgcuucag cguucaagag acgagcugau 300
gagaagaaug caguggcggg uguuacaaau auuccugcga auccaaacac aacgguuacg 360
acgaaccaag ggaguacuac uacuaccaag gcgaacacug gcucgacuuu ggaagaagac 420
uuguacacuu auuacaaauu cgaugaugcc ucuacagcuu uccacaaauc ucuaacuucg 480
uuagagaaca uggaguugaa gaguuauuac cgaaggaacu uugagaaagu auucgggauu 540
aaguuuggug gagcagcugc uaguucaucu gcaccgccuc cagcgagugg agguccgaua 600
cguccuaauc ccuag 615

<210> SEQ ID NO 32
<211> LENGTH: 615
<212> TYPE: RNA
<213> ORGANISM: Artificial Sequence
<220> FEATURE:
<223> OTHER INFORMATION: Sythetic Tobacco Rattle Virus codon-optimized coat protein mRNA sequence

<400> SEQUENCE: 32
augggugaca uguacgacga gucguucgau aaguccggug gcccggccga cuugauggac 60
gacagcuggg uggaauccgu cagcuggaaa gauuugcuga aaaagcucca uucuaucaag 120
uuugcguuac aauccggucg ugaugagauu accggccugc uggcggcccu gaaccgccag 180
ugcccguaca gcccguauga gcaauuccca gacaaaaaag ucuauuuccu gcuggauagc 240
cgugcuaaua gcgcccuggg cguuauucag aaugcgucug cguuuaagcg ccgcgcggac 300

-continued gagaagaacg cgguggcggg cguuaccaau aucccggcua acccgaacac cacgguuacg 360
accaaucaag guagcacuac caccaccaag gcuaacaccg gcucgacccu ggaagaggac 420
uuguacacuu acuauaaauu ugacgacgcg ucgaccgcau uccacaaauc gcugaccucc 480
uuggaaaaua uggaacugaa gucuuauuac cgccguaacu ucgagaaagu guuugguauu 540
aaauuuggug gcgcagccgc auccagcucg gcgccgccac cggcgagcgg uggcccgauu 600
cguccgaauc cuuaa 615

<210> SEQ ID NO 33
<211> LENGTH: 519
<212> TYPE: RNA
<213> ORGANISM: Artificial Sequence
<220> FEATURE:
<223> OTHER INFORMATION: Tomato bushy stunt virus P19 supperssor protein CDS DNA

<400> SEQUENCE: 33
auggaacgag cuauacaagg aaacgacgcu agggaacaag cuaacaguga acguugggau 60
ggaggaucag gagguaccac uucucccuuc aaacuuccug acgaaagucc gaguuggacu 120
gaguggcggc uacauaacga ugagacgaau ucgaaucaag auaaucccu ugguuucaag 180 gaaagcuggg guuucgggaa aguuguauuu aagagauauc ucagauacga caggacggaa 240
gcuucacugc acagaguccu uggaucuugg acgggagauu cgguuaacua ugcagcaucu 300
cgauuuuucg guuucgacca gaucggaugu accuauagua uucgguuucg aggaguuagu 360
aucaccguuu cuggagggguc gcgaacucuu cagcaucucu gugagauggc aauucggucu 420
aagcaagaac ugcuacagcu ugccccaauc gaaguggaaa guaauguauc aagaggaugc 480
ccugaaggua cugagaccuu cgaaaaagaa agcgaguaa 519

<210> SEQ ID NO 34
<211> LENGTH: 1371
<212> TYPE: RNA
<213> ORGANISM: Artificial Sequence
<220> FEATURE:
<223> OTHER INFORMATION: Papaya ringspot virus strain P isolate pFT3-NP Hcpro peptide CDS sequence

<400> SEQUENCE: 34
aaugauguug cugaaaaauu cuggcucggu uucaacaggg cuuucuuacg acacagaaaa 60
ccaacggauc augugugauc aucugauaua gauguuacga ugugugguga aguagcggcu 120
uuggcaacca uaaucuuguu uccgugucau aagaucacuu gcaacacuug caugaacaaa 180
guaaagggga gaguaauuga cgaaguuggu gaggacuuga auugugagcu ugaacguuua 240
cgugaaacuc ucucgucaua uggaggcuca uucggucaug uaucaacauu acucgaccaa 300
cugaacagaa uuuugaaugc acguaacaug aacgacggag cuuuuaaaga aguugcaaag 360
aagauugaug caaagaaaga aaguccuugg acccaccuaa cagccaucaa uaacacgcuu 420
auuaaagguu cguuagcaac uggcaaugaa uuugaaaaag caucugauag ccugcgggaa 480
guugugaggu ggcaucucaa aagaacagag ucaauaaaag cuggcagugu ugagagcuuu 540
agaaacaagc guucugggaa agcucacuuu aacccagcuc uuacguguga caaucaauug 600
gacagaaaug gcaauuucuu augggggugaa agacaauauc acgccaaaag auucuuugcu 660
aacuacuuug aaaagauuga ucacaguaag gguuaugagu acuauaguca acgccagaac 720
ccaaauggca cucgaaaggu ugccauuggu aauuuaauau ucuccacaaa uuuggagagg 780
uuucggcagc agauggucga acaucacauu gaccagggac caaucacucg ugaguguauc 840
gcacugcgca acaacaauua ugcucaugua uguagcugcg ugaccuugga ugauggaacu 900
ccagcaacga gugaauugaa aacucccacc aagaaucaca ucguucuugg uaauucuggu 960
gauccuaagu auguugacuu gccgacucuu gagucugauu caauguacau agccaagaaa 1020
gguuauugcu acaugaacau cuuuuuggcg augcucauaa acauaccuga gaaugaggcg 1080
aaggacuuua cgaagagagu ucgcgaucuu guugguucaa agcuugggga guggccaacg 1140
augcuagaug uugcaacaug cgcuaaucaa uugauuaucu uccaucccga ugcagccaau 1200
gcagaauugc cgcgaauuuu gguggaucac cgacagaaga caaugcacgu aauugauucg 1260
uuuggaucug uugauucugg auaucauaua cugaaggcua acacagucaa ucaguugauc 1320
caauucgcca gagagccacu cgauagugaa augaaacacu acauugucgg u 1371

<210> SEQ ID NO 35
<211> LENGTH: 807
<212> TYPE: RNA
<213> ORGANISM: Artificial Sequence
<220> FEATURE:
<223> OTHER INFORMATION: Tobacco mosaic virus TMV 30kDa movement protein CDS sequence

<400> SEQUENCE: 35
auggcucuag uuguuaaagg aaaagugaau aucaaugagu uuaucgaccu gacaaaaaug 60
gagaagaucu uaccgucgau guuuaccccu guaaagagug uuauguguuc caaaguugau 120
aaaauaaugg uucaugagaa ugagucauug ucagagguga accuucuuaa aggaguuaag 180
cuuauugaua guggauacgu cuguuuagcc gguuuggucg ucacgggcga guggaacuug 240
ccugacaauu gcagaggagg ugugagcgug ugucuggugg acaaaaggau ggaaagagcc 300
gacgaggcca cucucggauc uuacuacaca gcagcugcaa agaaaagauu ucaguucaag 360
gucguuccca auuaugcuau aaccacccag gacgcgauga aaaacgucug gcaaguuuua 420
guuaauauua gaaaugugaa gaugucagcg gguuucuguc cgcuuucucu ggaguuugug 480
ucggugugua uuguuuauag aaauaauaua aaauuagguu ugagagagaa gauuacaaac 540
gugagagacg gagggcccau ggaacuuaca gaagaagucg uugaugaguu cauggaagau 600
gucccuaugu cgaucaggcu ugcaaaguuu cgaucucgaa ccggaaaaaa gagugauguc 660
cgcaaaggga aaaauaguag uaaugaucgg ucagugccga acaagaacua uagaaauguu 720
aaggauuuug gaggaaugag uuuuaaaaag aauaauuuaa ucgaugauga uucggaggcu 780
acugucgccg aaucggauuc guuuuaa 807

<210> SEQ ID NO 36
<211> LENGTH: 7445
<212> TYPE: RNA
<213> ORGANISM: Arabidopsis thaliana

<400> SEQUENCE: 36
augucuaccu cgucgcaauc uuuuguggcu ggacggccug cauccauggc uuccccuucg 60
caaucgcacc gcuuuugugg ucccucagcc accgcuucug guggcggaag cuuugacacu 120
uugaaucgug ucaucgcuga ccuuugcagc cgugguaauc cuaaggaggg agcuccuuua 180
gcguuuagga aacacguaga ggaagcaguu cgugaucuua gugggugaagc uuccucuagg 240 uucauggagc aauuauauga caggauugcu aauuuaauug agagcacuga uguggcggaa 300
aacaugggug cacucagagc cauugaugag uugacggaga uuggauuugg ugagaaugcu 360
acuaagguuu cuagauuugc ggguuacaug aggacugugu ucgaguugaa gcgugauccu 420

-continued

```
gaaaucuugg ugcuugcuag uagaguuuug gggcaccuug cucgggcagg uggagcaaug    480
acuucugaug aaguggaguu ucagaugaaa acagcuuuug auuggcuucg cguagacagg    540
guggaauauc gucguuucgc cgccguuuua auauuaaagg agauggccga aaaugcuucu    600
acugucuuua acguucaugu cccugaauuu guggaugcua ucuggguugc acuuagggac    660
ccccaguugc aagugcgaga acgagcuguu gaagcuuugc gugcaugccu ucguguuauu    720
gagaaaaggg agacucgaug gcgagugcag ugguacuauc gaauguuuga agcuacacag    780
gaugguuggg gcagaaaugc uccgguucac aguauucaug guucuuuacu ugccguggggg    840
gagcuguuga ggaauacagg ugaguucaug augucuaggu auagagaagu ugccgaaauu    900
guccucagau accuugaaca ucgugaucgc cuuguucgcc uuagcaucac cucguuacug    960
ccucgcauug cucacuuucu ccgugaccgg uuugugacaa acuauuuaac gauaugcaug   1020
aaucauauuc uuacuguguu aagaauaccg gcugaaagag ccagugggguu caucgcccuu   1080
ggggaaaugg cuggugcuuu ggauggugag cuuauccauu auuugccgac aauuaugucu   1140
caucugcggg augcgauugc uccacguaaa ggcagaccuu ugcuugaagc uguggcuugu   1200
guugguaaca ucgcaaaggc aaugggaucc acaguggaaa cucauguucg agaucuuuua   1260
gauguuaugu uuucaucuag ucucucuucc acacuuguug acgcucuuga ccagauaacc   1320
aucagcauuc cuucuuugcu gccaacagua caagaucggc uucuagauug cauuucguug   1380
guucuuucaa aaucccauua uucucaagca aagccuccug uuaccauugu ccgagguagu   1440
acagugggca uggcaccaca gucuucugac ccuaguuguu cagcucaagu ucaacuagcc   1500
cugcagacuc uugcucguuu caauuucaag ggacaugauc uucuugaauu ugcucgggag   1560
ucaguuguug uuuauuugga ugaugaggau gcagccacaa gaaaagaugc ugcuuugugu   1620
uguugcagac uaauugcaaa uucucuuucu ggcaucacac aauuuggcuc gagcagguca   1680
acacgagcag gggggagacg caggcgccuu guggaagaga uuguggaaaa gcuucucagg   1740
acagccguug cagaugcuga uguaacuguu cgcaaaucua uauucguugc uuuauuuggc   1800
aaccaauguu ucgaugauua ucuagcacag gcugauaguu ugacugccau uuuugcuucc   1860
uuaaaugaug aggaccuuga uguucgagaa uaugccaucu caguugcugg aagguuaucg   1920
gaaaaaaauc cagcauacgu acuuccagca cuucgucgcc aucuuauaca guuguugacc   1980
uaucuugagc ugagugcaga uaacaagugc agggaagaga gugcaaagcu ccuugguugu   2040
uuaguucgaa auugugaacg gcucauucuu ccauacguag ccccugucca aaaggcacuu   2100
guugcgagac uuagugaagg aacuggagug aaugcuaaca auaauauugu cacuggaguu   2160
cucguaacug uuggggaucu ugcaagagug gguggcuugg caaugagaca auauauuccg   2220
gagcugaugc cuuuaauugu ugaagcuuua auggauggag cugcuguagc aaaacgugag   2280
guggcuguuu cuacucuugg ucaaguuguu caaaguacag gguauguugu gacuccauac   2340
aaggaauacc cauuguugcu uggguuacuc uugaaauugc ugaaggguga cuuagugugg   2400
ucuaccagac gagaagugcu caagguucuu ggaauuaugg gcgcuuugga uccucaugug   2460
cauaaacgua accaacaaag uuuaucagga ucacauggug aaguuccucg cggcacuggu   2520
gauucugguc aaccuauucc aucaauugau gaguuaccug ucgaacuccg gccgucauuu   2580
gcuacaucug aggauuauua cucaacgguu gcuaucaacu cgcuuaugcg aauucuuaga   2640
gaugcaucac uucuuaguua ccacaaaagg guuguuagau cucugaugau cauuuucaag   2700
ucaaugggau ugggaugcgu gccuuacuug ccgaagguuu uaccugagcu uuucacacu   2760
```

-continued guucgaacau cugaugagaa ccugaaggac uucauuacgu ggggucuugg gacucuuguu 2820
uccauuguuc gccagcacau acgcaaguau cugccagagc ugcuuucauu agucucugaa 2880 cuaugguau ccuucaccuu gcccgguccc auacgcccau cacguggucu uccgguucug 2940
caucuacugg aacaucuuug cuuggcacuu aaugaugaau ucagaacuua ucuuccaguc 3000
auccuuccau guuucaucca aguauuaggu gacgccgagc gguuuaauga uuacaccuau 3060
guuccugaua uucuccacac acucgaagug uuuggcggaa cucuugauga gcacaugcau 3120
uuacuccuuc cggcacuuau ucgauuguuu aaaguagaug cuccuguagc uauaagacgc 3180
gaugccauca aaacuuugac aagaguaauc ccgugugguc agguuacugg ucauaucucc 3240
gcucucgugc aucacuugaa gcuaguauua gaugggaaga augaugaguu gcggaaagau 3300
gcugucgaug cacuaugcug uuuggcucau gcacuuggag aggacuucac cauauucauu 3360
gaaucaauuc acaagcuuuu auugaagcau cgauugcggc auaaagaauu ugaggaaauu 3420
caugcucgcu ggcggagacg ugaaccauug auuguagcua caacugcaac ccaacaauua 3480
aguaggcgac ugccaguuga gguuaucagg gauccuguaa uugagaauga gaucgauccu 3540
uucgaagaag gaacugacag aaaccaucag guuaaugaug guagacuacg gacagcugga 3600
gaagcuucuc aacgcagcac caaagaagau ugggaggaau ggaugagaca uuuuaguauu 3660
gaauuacuua aggagucucc cucuccagca uuaagaacuu gugcaaaacu ugcucaguug 3720
cagccauuug ucgggagaga guuguuugcu gcuggcuuug ucaguugcug ggcacagcua 3780
aacgagucua gccaaaagca guuaguuagg agcuuggaaa uggccuuuuc aucuccaaau 3840
aucccuccag aaauuuuagc uacacuacuc aauuuggcag aguuuaugga acaugaugag 3900
aagccucuuc ccauugauau ucgucuucug ggggcucuug cugaaaagug ccguguuuuu 3960
gccaaagcuc ugcauuauaa agagauggaa uuugaagguc cacgauccaa gaggauggau 4020
gccaacccag uugcuguugu cgaggcucuu auacacauaa auaaucaguu acaccagcau 4080
gaggcugcug ucgguauacu aaccuaugcu caacaacauc uugaugugca auuaaaagaa 4140
ucaugguaug agaagcugca gcgcugggac gaugcacuca aggcguacac uuugaaagca 4200
ucucaaacaa caaauccuca ucuuguauua gaagccacau uaggacaaau gagaugucuu 4260
gcugcacuug cacgauggga agagcucaac aaucucugca aagaguacug gaguccugcu 4320
gagccaucug cgcgucugga aauggcacca auggcugcac aagcugcaug gaacauggga 4380
gagugggauc aaauggccga auaugugucu cggcuagaug auggugauga aacaaagcuu 4440
cggggguuag caagcccggu uucuaguggc gaugggagca guaauggcac auucuucagg 4500
gcuguucugu uaguucgaag ggcaaaguac gacgaggcac gcgaauaugu ggaaagagcu 4560
agaaaauguc uugccacaga acuugcagcg cugguuuugg agagcuauga gcgugcguac 4620
agcaauaugg uucguguuca gcagcuguca gaacuagagg agguaauuga auauuauacg 4680
cugccugugg gaaauacuau ugccgaagaa cggagagcuc uaauucguaa uauguggacu 4740
cagcggauuc agggaucuaa gcguaaugug gaggugugge aagcacuuuu ggcuguccgg 4800
gcacuugugc uaccuccuac agaagaugug gaaacuuggc ucaaguuugc cucgcuuugu 4860
cgaaagagug ggaggaucag ucaggcgaaa ucuacucuac ucaagcucuu accguuugau 4920
ccagaaguau caccagaaaa caugcaauau cacggaccuc cacaagugau gcuuggauac 4980
uuaaaauacc aauggucacu uggagaggaa cguaagcgca aagaggcauu uaccaagcug 5040
cagauucuaa cgagagagcu cucaagugug ccacauucuc aaucugacau acuggcuagc 5100
augguaucua gcaagggcgc aaauguucca cuucuugcac guguaaaucu caaacuggga 5160

-continued

```
acguggcagu gggcacuuuc uuccgguuug aaugaugggu cuauucaaga aauucgugau   5220
gcguuugaca aaucuacuug cuaugcuccu aaaugggcua aagcauggca cacaugggca   5280
uuauucaaua cagcagugau gucgcauuac auuucaagag gucaaauugc uucccaguac   5340
guuguuucug cagucacugg auauuuuuau ucuauagcau gugcagcaaa ugccaaagga   5400
guugaugaua guuuacagga cauacugcgu cuucugacau uguggguucaa ccauggagcu   5460
acagcugaug uccaaaccgc auugaagaca ggauucaguc augucaacau uaacacaugg   5520
cuuguugugc uaccucaaau cauugcuagg auacauucua auaaaucgugc ugucagggaa   5580
cugauucagu cucuucucau ccgcauaggc gaaaaccacc cacaggcucu gauguauccc   5640
cuucucguug cauguaaauc aauaagcaau cuucggagag cugcggcuca agaggugguu   5700
gauaaaguuc gccagcacag uggugcacuc guggaucagg cgcaacuugu aucacaugaa   5760
cuuaucaggg uugccauacu uuggcaugaa auguggcaug aagcacuaga agaagcuagu   5820
cgcuuguauu uuggugaaca uaacauugaa ggcaugcuga aaguacuuga acccuuacau   5880
gacaugcucg acgaaggugu aaaaaaggac aguacgacca uacaggaaag agcauuuaua   5940
gaggcauacc gucacgaacu aaaagaggca caugaaugcu guugcaauua caagauaacu   6000
gggaaagaug cugaacuuac acaggcuugg gaucuuuacu aucacguuuu caaacggauu   6060
gacaaacagc uagccagucu cacgacauug gauuuggaau cuguuucucc ugaguugcug   6120
cugugccgug acuuggagcu agcaguuccu ggaacauauc gugcagaugc cccgucgug   6180
acuauaucau cuuuuucacg ccaacuuguu guuauaaccu cuaaacaaag accaaggaaa   6240
uugacuauuc acggaaauga cggugaggac uacgccuucu uguugaaggg acaugaagau   6300
uuaaggcaag augagcgugu uaugcagcuu uuugguuugg ugaacacuuu gcuugagaau   6360
uccagaaaaa cagccgaaaa agaucuuucc auucaacgcu auucuguaau accacuaucu   6420
cccaauagug gacucaucgg augguuccg aacugcgaua cccuucacca ucuuauucga   6480
gagcacagag augcaagaaa gaucauucuu aaucaagaaa auaagcauau guugaguuuu   6540
gcuccagacu augacaaucu accgcuuaua gcaaagguug aaguauuuga guaugcucua   6600
gaaaacacag agggaaauga ucuauccagg guucucuggu uaaaaagucg cucgucagaa   6660
guuuggcuag aaagaagaac aaacuauacu agaaguuuag caguuaugag uaugguuggu   6720
uauauucuug gguuagguga ucgacaccca aguaaccuua ugcuucauag auacagugga   6780
aagaucuugc auauugauuu uggagauugu uuugaggcuu cuaugaauag agagaaguuu   6840
ccugaaaagg uuccauuccg ccugacaaga augcuuguca aagcaaugga agucagugc   6900
auugaaggaa acuuccgcuc aaccugcgaa aacguuaugc aaguucucag aaccaauaaa   6960
gauaguguaa uggcaaugau ggaagcguuu guacaugauc cuuuaaucaa uuggcgucuu   7020
uucaauuuca augaaguccc ccaauuagca cugcucggua acaacaaccc caaugcuccu   7080
gcugauguug agccugacga agaagaugaa gaucccgcug auauagaucu ucccucagccu   7140
caaaggagua cucgagagaa ggagauuuuc aggcuguaaa uaugcuugga gaugcuaaug   7200
aaguuuuaaa ugagcgugcc guaguuguua uggcacguau gagucauaag cuuacagggc   7260
gugauuuuuc uucgucugca auuccgagca aucccauugc ugaucauaau aacuugcucg   7320
gaggagauuc ucaugaaguc gaacaugguu ugucugugaa aguucagguu caaaaacuaa   7380
ucaaucaagc cacuucccau gagaaucucu gucaaaacua uguugggugg ugcccuuucu   7440
gguga                                                               7445
```

<210> SEQ ID NO 37
<211> LENGTH: 1014
<212> TYPE: RNA
<213> ORGANISM: Arabidopsis thaliana

<400> SEQUENCE: 37
auggcgaagg aagcggucaa guauguaugg gaaggagcaa uuccucugca gauucaucuc 60
cacaaauccg acgucgcuuc ucacccugcu ccuccuccug cucuuguguu agcaccaaga 120
auaggauauu ugccucuguu gauuccucuu auaaagccuu auuucaagga uucacuuccu 180
ccuggugaag auucaauuug guuugauuac aaaggauuuc cucuaaaaug guauauacca 240
acagguguuc uuuucgaucu ccuuugugca gaacccgaaa gaccauggaa ucucacgaua 300
cacuuuagag gauauccuug caacauacug auaccaugug aaggagaaga uucuguaaaa 360
uggaacuuug uuaauucuuu gaaagaggca caauauauca ucaauggaaa uugcaagaau 420
guuaugaaca ugucucagag ugaucaagag gaucuaugga ccucugucau gaacggugau 480
cuugaugccu auacaagauu aucacccaag cuuaaaaugg gaacagucga agaugaguuu 540
ucaaggaaaa caaguuuguc aucuccacaa ucucaacaag uugugccuga gacggaggug 600
gcuggacaag uuaagacagc aagaauuccu guucgguugu auguucgaag ucuaaauaaa 660
gauuucgaga aucuugaaga uguaccggag aucgauaccu gggaugacau cucguaccuu 720
aaucgcccug uugaguuccu caaagaagaa gggaaaugcu uuacguuacg ugacgccauu 780
aaaagucucc ucccugaguu uaugggagac agagcgcaaa cgagugguga agaaagaagc 840
auagaugaua cagaagaagc agaugggucg agggagaugg gugaaaucaa auugguaagg 900
auacaaggga uagaaaugaa gcuagagaua ccguuuucgu ggguggиaaa uaacuugaug 960 aacccagaau ucuaucucca uaucucuguc cuugugaaag cuccucaaag guga 1014

<210> SEQ ID NO 38
<211> LENGTH: 1554
<212> TYPE: RNA
<213> ORGANISM: Arabidopsis thaliana

<400> SEQUENCE: 38
augaggaaag aggagauucc agauaaaagu cggacuaucc cgaucgaucc gaaucugccg 60
aaaugggucu gccaaaacug ucaccacucc cuuaccaucg ucggcgucga uuccuacgcc 120
ggcaaguucu ucaacgaucc cccuccgucc gcuacgcagg gcucaucuau ccauggagcu 180
aacaguguuc uugguucaac acgcauggac aacucuuuug uuguuuuacc ucgacauaag 240
ccuccucaau cucagggcau ucccuccacgu ccucgcgggg cguccucacc ucagccugau 300
gcuacucaau cuggaaaggc gauggaggaa ucguuuguag uugucuauaa gucugagccu 360
guuucugauu cugguguuc ucacaaucug ucucuugaag ugggccaaaa cggucccuua 420
cauucaaaua cuucuggcuu uaaugcgacu aucaaugucu uaacucgugc uuuugauauu 480
gcuagaacuc agacacaggu ugaacagcca uugugcuuag aaugcaugag gguauuugucu 540 gauaaacuug aaaaagaagu cgaggaugug acgagggacg uggaagcaua cgaagcaugc 600
guucagaggu uagaaggaga gacgcaagau guucuuagug aagcugauuu ucucaaggaa 660
aagaagaaga uugaggaaga agaaagaaaa cuuguugcag cuauagaaga aacagagaaa 720
caaaaugcug aaguaaacca ucaacugaag gagcuagaau ucaagggaaa ucguuuuaac 780
gaacuugaag aucgguauug gcaagaguuc aauaauuuuc aguuucaauu aauugcccau 840
caggaagaga gagaugcaau cuuggcaaag auugaaguuu cacaagcaca uuuagaguua 900
uuaaauaaga caaauguacu uauugaugcc uuccccauac ggaaugaugg ggaauuuggu 960
acaauuaaca auuuucgacu uggaagacuc ccugccauaa aaguugagug ggaugagauc 1020
aaugcugcuu ggggccaagc cugucuucuc cuccauacga uguguaacua uuuccggcca 1080
aaguuucaau gucaaguuaa aauacagccg auggggaguu auccuagaau uguagacagc 1140
aacaacgaaa cuuaugagcu guuugguccu guuaacuugu uuuggagcac ucgguacgau 1200
aaagccauga cacuguauuu gaugugucuu aaagacuuug cugauuuugc aaauucaaag 1260
gaccaagaga acaauauucc accagauaau ugccucaacc uuccauacaa gaucgaaaag 1320
gacaaaguau uggguauuc aauaacacag agcuucaaca agcaagagag uuggaccaaa 1380
gcacuaaagu auacucucug caaccucaaa ugggcucucu acugguucgu uggaaacacu 1440
aauuuccaac cucucucugc gacggucucu cugccuucua auauaucagc ggcugguucc 1500
uuguacgcca agcgaggucc ugacucuagu aagccuucau guaaaaaaac uuag 1554

<210> SEQ ID NO 39
<211> LENGTH: 1024
<212> TYPE: RNA
<213> ORGANISM: Artificial Sequence
<220> FEATURE:
<223> OTHER INFORMATION: Nicotiana attentuata ZIM domain protein hmRNA
sequence used for building targeting constructs

<400> SEQUENCE: 39 auuucuugu gauuuuuaaa acaugucaaa uucgcaaaau ucuuuugacg gcggcagaag 60
ggccggaaaa gcgccggaga gaucgaauuu cgugcagacu uguaauuuau ugagucaguu 120
uauuaaagga aaagcuacua uuagagaucu gaaucucgga auugcuggaa aaucugaaau 180
cucagguaaa agugauguua cagaagcugc aacuauggau uuauugacaa uuauggaaaa 240
ccccucaauu gaaacuaaag aacaagaaca aaaauccaua gaucccguuc gucagagugc 300
uguaacagaa ucuucuagag auauggaggu ggccguaaau gagcccagca cgagcaaaga 360
ggcaccaaaa gagccuaagg cagcacaauu gacuauguuc uaugauggua aagugauagu 420
auuugaugau uuuccagcug acaaagcuag agcaguaaug uuauuggcua guaaaggaug 480
cccucagagu ucauuuggca cuuuucauac uacaaccauc gacaaaauua acacaucugc 540
uacugcugcu gccacagcuu cuuugacaug uaauaaaacu aaucagcuua aaccaaguac 600
aguuucuauu gcaccaccac aacaaaagca gcagcaaauu cauguuucuu auaguaaaag 660
ugaccaacuc aagccagggu auaauucugc uacgccgcaa guacugcagc agcagcuagu 720
ccauguuucu aguacuagua aaacugauca gcuuaagcca guaucaacuu cuucugcguc 780
gcaaaaacag caggagcaac aucagcaaac gcagucacag acaccuggaa cuagcagcuc 840
ugagcuaccu auugcaagaa gaucaucacu acauagguuu cuugagaaga ggaaagauag 900
ggcaacggcu agagcgccau accaaguugu acauaauaau ccguuaccau caucuucaaa 960
uaauaauggg gaaucaucuu ccaaggauug cgaagaucaa cucgaucuca auuucaaguu 1020
auag 1024

<210> SEQ ID NO 40
<211> LENGTH: 750
<212> TYPE: RNA
<213> ORGANISM: Nicotiana benthamiana

<400> SEQUENCE: 40
auggagucuu gcacaucguu cuucaauucg cagucggcgu cgucucgcaa ucgcuggagu 60

-continued

```
uacgauucuc uuaagaacuu ccgccagauc ucucccuuug uucaaacuca ucucaaaaag    120

gucuaccuuu cauuaugcug ugcuuuaauu gcuucggcug cuggagcuua ccuucacauu    180

cuuuggaaca ucggugguuu acuuacgacg cugggaugcg ugggaagcau aguauggcug    240

auggcgacuc cucuguauga agagcaaaag aggauagcac uucugauggc agcugcacug    300

uuuaaaggag caucuguugg uccacugauu gaacuggcua uugacuuuga cccaagcauc    360

guguuaggug cuuuuguugg uugugcugug gcuuuugguu gcuucucagc ugcugccaug    420

guggcaaagc gcagagagua cuuguaucuu ggaggucuuc uuucaucugg ucucucuauc    480

cuuuucuggu ugcacuuugc guccuccauu uuuggugguu cuauggcccu auucaaguuu    540

gagguuuacu uugggcucuu ggguguuuguu ggcuauauca uuuuugacac ccaagauaua    600

auugagaagg cacaccuugg ggauuuggac uacgugaagc augcucugac ccucuuuaca    660

gauuuuauug cuguuuuugu gcgaauuuua aucauaaugu ugaagaaugc auccgacaag    720

gaagagaaga agaagaagag gagaaacuaa                                      750
```

```
<210> SEQ ID NO 41
<211> LENGTH: 959
<212> TYPE: RNA
<213> ORGANISM: Artificial Sequence
<220> FEATURE:
<223> OTHER INFORMATION: Nicotiana sylvestris Acd2 partial transcript
      sequence dervied from N. sylvestris transcriptome

<400> SEQUENCE: 41

guucauccuc aaaauacaug gaacagcaga augaaaacaa gucgaaauug aaggaauuuc     60

cuuacguguc ggucccacau agggaguuga ugguugaacu uauaucgacu guggagaauc    120

ggcuuggaac agcucuucug ccuuguacuc ugccuucuaa cgugcaguac uuugagaauu    180

cgacugcuac ugcucaugcu ucucucuaug ucagaucugg ccacuccucu ucccagguug    240

auuucauacu ggguaguugg guucacugcg acuugcccac agguggagcc uugaacauua    300

caagccucuc cgccuauuug agaccuucaa cugaugcacc aaacuucuua aucgaaguca    360

uccgcagcag uccaacaucu cucauccuca uucuugaucu accuccacga aaggaccucg    420

uccaacaucc ugauuaccuu aaaaccuuuu acgaggaaac acaauuagac gaacagagac    480

aacuucucga gaagcuaccu gaggugaagc cuuacuucuc uucaucucua uauauccgag    540

cuguugucuc uccgucagcu aucuugguuu ccauagaaac cgaagcuucu caggccguuc    600

gcauugauga gauuauucag gaccacauaa guccuguugc uaagguaaug uuggagacau    660

gguuggaucu gugugcuugu gcugagagaa aauugacaga ggaugaaagu acagcuuugg    720

caaagaggga uaaaauaauu aagaauaaga caauugagau agaucuugaa ucaagcuucc    780

cuaggcuuuu uggucaagaa guagcaaaca agguuuuagu aguacuaagg gaaaucuaca    840

augcuugaau cucuuacuua ugcagcuguu gauuaauaca gaaaggugau uauuguaugu    900

aaucuuguua auucuucaaa uaucagaaaa ggcaaauuga aaguaauuau aaaaguugc     959
```

```
<210> SEQ ID NO 42
<211> LENGTH: 1717
<212> TYPE: RNA
<213> ORGANISM: Lycopersicon esculentum

<400> SEQUENCE: 42

cuucuuuacu ugaacauaug uguauuagua acacaaaaca uugauuaacu caauaauggu     60

uucuucucug uuacuaccaa cuccucaaau ucuuucaauu ucaucuuccu uacagucuuc    120
```

acuaccuuuc aaaccucaua auuuucuuca aauuacaagg aaaaaaaaua cgcuaauuuc 180
aucuccucuu agaguagcug caccuccaac aacaacaaca gcuacugaag aagaagagaa 240
gcuagauuca aaaucuagug auauugaaga uacagaaaau gaugaacaag auucgucguc 300
gaaauucucu uggagagauc auugguaccc aguuucauua guggaagauc ucgacccgag 360
uuuacccaca ccguuucagc uacugaaucg ugauauaguu aucugguuug auaaaucugg 420
aucucagugg guugcuuugg augacaaaug cccucaucgu cuugcuccuu uaucugaagg 480
gagauuagau gaaaauggug auuugcagug uucauaucau ggauggucau uuaauggaug 540
ugguucuugu acaaggauac cucaagcugc aucucaagga ccugaagcua aagcuuuuca 600
gucuccaaga gcuugugcua cuagauuucc uacuaugguu ucucaaggau uacucuuugu 660
uuggccugau gaaaauggau gggagagagc ucaggcaaca aagccgccca uguugccuga 720
agauuuugau aagccugagu uugcaacugu gacaauucag cgugauuugu uuuauggcua 780
ugacacucuc auggagaacg ucucugaucc uucucacauu gauuuugcac accacaaggu 840
uacuggaagg cgagacagag caaagcccuu gccauucaag auggaggcau cuggaccuug 900
ggguuuugcu ggugcgaaca augauaaacc aaaaauuacu gcaaaauuug ucgcaccuug 960
uuacucaaug aauaaaauag agaucgacac aaagcuucca aucgugggug aucagaagug 1020
ggugauaugg auuuguuccu uuaauguacc uauggcacca ggaaagacca ggucaauugu 1080
uuguagugcu cgaaacuucu cccaguuuac agugccuggc ccugcuuggu ggcagguuuu 1140
uccaagaugg caagaacacu ggacuucaaa uaaggugauu gacggggaua ugauuguucu 1200
ucaaggucaa gaaaaagucu uucuuucaaa gucgaaagaa aaugguacug augucaacaa 1260
agaguauaca aaacucacau uuacaccuac ucaagcugau cguuucgucu uggcauuccg 1320
aaauuggcuu agacggcaug gcaauaguca accugaaugg uuugguagca cagacaacca 1380
accacugcca ucuacugucu uauccaaacg ccagaugaug gacagauucg aacaacauac 1440
acucaaaugu ucaucuugca aaaaggcuua cuacacauuc gagaaguuac aaaaguuacu 1500
gauuggcuca guagugguau gcugugcauc ugcaggcauc ccugcagaug uuaaccuacg 1560
aauuauauug gguucauuag caauuauaag ugcuggauua gcauacauuc uacacgaauu 1620
acagaaaaau uucaucuuug uugauuaugu acaugcugaa auugacuaaa cauaucaucu 1680
aagaacuuuc ucuauaaaua gcagauauuu gauuugu 1717

<210> SEQ ID NO 43
<211> LENGTH: 1532
<212> TYPE: RNA
<213> ORGANISM: Nicotiana tabacum

<400> SEQUENCE: 43
agaaaggcaa cuaauggauc cauacaagua ccguccguca agugccuuca auucuccauu 60
cugcaccacu aauucuggug cuccuguuuu uaacaacaau ucaucucuua cuguuggugc 120
aagagguccu guauugcuug aggauuacca uuuggugggag aaacuugcca auuuugacag 180
ggaacguguc ccugaacgug uuguucaugc ccgaggugcu agugccaaag gguuuuucga 240
aguuacccau gacaucacuc accuuaccug ugcugauuuc cuucgagcuc ccggugucca 300
gacuccuguc auugugagau ucuccacugu uauacaugag agggguaguc cugaaacucu 360
gagggacccu cgugguuuug cugucaaguu cuacaccaga gagggaaacu uugaucuggu 420
agggaacaac uuccccgucu ucuucauccg ugauggaaug aaguucccug acauggucca 480

```
cgcgcugaag ccaaauccua aaucccauau ccaggagaau uggagggucc uugauuuuuu    540

cucucauguu ccugaaagcc ugcacauguu cacuuuccuc uucgacgaua uugguauucc    600

acaagauuac aggcauaugg acgguucugg uguccacaca uucacauuga ucaacaaggc    660

ugggaaauca accuauguga aguuccacug gaagcccaca ugugguguca aguccuuguu    720

ggaagaagaa gcagcccgua ucggaggagc aaaucacagc cacgcuacuc aagaccucua    780

ugacucuauu gccgcuggaa auuauccuga auggaagcuc uucauucaga cuauggaucc    840

agaucaugaa gacagauuug auuuugaucc acuugauguu acaaaaacuu ggccagagga    900

uaucuugccg uugcagccgg ugggaagauu aguucugaac aagaacauug auaacuucuu    960

uaaugagaau gagcaacucg cuuucugccc uucuauugug guuccaggug uuuauuacuc   1020

agaugacaag augcuucaaa cucguauuuu cuccuacucu gauacccaga gguaucgacu   1080

uggaccaaac uauuugcaac uuccugcuaa ugcuccaaag ugugcucauc acaacaauca   1140

cuaugauggc ucuaugaauu uuaugcacag ggacgaggag aucgacuacu ucccuucaag   1200

guaugauccu guucgccaug cugagaagua uccaauuccu ucuacaaugu gcacuggcaa   1260

acgagagaag ugugucauuc agaaagagaa caauuuuaag caaccaggag auagguaccg   1320

cucauucaca ccagacaggc aagaacgcuu uauucgucgg uggguggagg ccuugucuga   1380

uccucguauc acuuaugaga uccgcagcau uuggaucuca uacuggucuc aggcugacaa   1440

aucucugggu caaaagcuug cuucuaggcu uaaugugaga ccaagcauau gaagaugaag   1500

cuuuuaaugg uuucggagga ggugauguca au                                 1532
```

<210> SEQ ID NO 44
<211> LENGTH: 1257
<212> TYPE: RNA
<213> ORGANISM: Arabidopsis thaliana

<400> SEQUENCE: 44

```
auguuguugc ugguggacug cuccagcugu cguacgccgc uucaccuucc ucccggagcc     60

acccgaaucc gcugcgccau uugucacgcc uucacucuca ucgcccccga gccccgucuc    120

caaucucacg cgucggcgag cccuuuuccu uuccccaacu caucuccggc uccauccacu    180

uucaucuacc cgccgccaac accuucuccg uacacucacg cgccgcaugc accgucucca    240

uucaaccacg cgccuccaga uucuuacccg uucacucacg cgccuccagc aucgucucca    300

uucaaccacg cgccgccggg uccuccaccg ccgguacaug gacagaagcg agcggugaua    360

gucgggguuu cuuacaagaa cacaaaggac gaacucaaag gauguaucaa ugacgcaaac    420

ugcaugaagu ucauguugau gaagcguuuc caauucccug aaucuugcau ucuuaugcuc    480

accgaagaag aagcggaccc aaugagaugg ccaacgaaga acaacauaac aauggcgaug    540

cauuggcuug uucuuagcug caaaccggga gauucccucg ucuuucacuu cuccggucac    600

ggcaacaacc agauggacga caacggcgac gagguugacg gcuucgauga gacucuucuc    660

ccgguggacc acaggacuuc aggugucauc guggacgaug agaucaaugc uacaaucgua    720

cggccgcucc cuuauggagu uaagcuccau gccaucgucg acgcuuguca uagugguacc    780

gucauggacu uaccuuaucu uuguagaaug gacaggcucg gaaacuauga augggaagac    840

caucggccua aaacaggaau guggaaaggu acgaguggcg gugaagucuu cuccuucaca    900

ggcugcgaug augaccagac cucggcugac acuccgcaau ugucagggag cgcauggacg    960

ggggcaauga cuuaugcauu cauucaggcc auagaacgug gccacgggau gacuuauggg   1020

agcuugcuga augcaaugag aucaacgguu caugagaucu ucgacaaaaa caaagguaga   1080
```

gagcuugugg aagugggagg ugcugauuuu cucucuacuc uucuugguuu gcucaucuua 1140
ggcgcuucuc cuccugauga ggaagaggaa guaaaccaag ccccucaaaa aacucaggaa 1200
ccacaguuga gcgcuaacga ggcauuugcu guauaugaga agcccuucuc uuuauaa 1257

<210> SEQ ID NO 45
<211> LENGTH: 507
<212> TYPE: RNA
<213> ORGANISM: Nicotiana benthamiana

<400> SEQUENCE: 45
auguugguuu accaggaucu uaucuccggu gaugagcucc ucucagauuc auuucccuac 60
aaagaacuug agaauggaug ucuuugggag guucaaggga agugggguugu ucaaggugcu 120 cuugauguag acauuggggc gaauccuucu gcugagggug cagaugaaga ugaaggugug 180
gaugaucaag cugucaaggu ugucgauauu guugacacuu ucagacuuca ggagcaacca 240
ucuuuugaca agaaacaauu uguuacauac augaagagau acaucaagaa ccugacuccc 300
aagcuagaag gagaagccca agaagcauuu aaaaagaaca uugaaucagc aacuaaguuc 360
cucaugucaa agcucaagga ccuucaguuc uuuguuggcg agagcaugca ugacgauggu 420
gcccuggugu uugcauacua caaggauggu gcaacugauc cuaccuuuuu guaccuugca 480
cauggacuca aggaggucaa guguuaa 507

<210> SEQ ID NO 46
<211> LENGTH: 633
<212> TYPE: RNA
<213> ORGANISM: Arabidopsis thaliana

<400> SEQUENCE: 46
augcaggacc agcuggugug ucaugguugu aggaauuuau ugauguaucc uagaggagca 60
ucuaaugugc guugugcguu auguaacacu aucaacaugg uuccuccucc uccuccaccu 120
cacgacaugg cacacauuau augugguggu uguagaacaa ugcuuaugua uacgcguggg 180
gcuaguagcg uaagaugcuc uugcugucaa acuacgaacc uugugccaga aucuucuuuc 240
acacuuuugu uugauaacau ucugaaagua cuuaaaacaa agcuuuuaga ugguccCggu 300
ggacuagcgc acuccaauca gguugcccau gcuccuucca gucagguugc gcagaucaau 360
uguggGcauu gucggacgac ccucauguau ccuuacggug caucauccgu caaaugcgcu 420
guuugucaau ucguaacuaa cguuaauaug agcaauggaa ggguaccucu cccaacuaac 480
cggccaaaug gaacagcuug uccccccucu acaucaacuu caacaccacc cucucagacc 540
caaaccguug uuguagaaaa ccccaugucc guugaugaaa gcggaaaguu ggugagcaau 600
guuguuguug gagugacaac ugacaaaaag uaa 633

<210> SEQ ID NO 47
<211> LENGTH: 621
<212> TYPE: RNA
<213> ORGANISM: Arabidopsis thaliana

<400> SEQUENCE: 47
auggcggauu cggaagcaga uaagccacug agaaaaaucu cagccgcuuu caaaaaacua 60
gcaaucaucg ugaauucacc gaauccggaa guuccuguaa cgcaauucuc ucacgcuugc 120
ucucuggucu cgccucucuu ugguugccuu ggaauagcuu uuaaguuugc ggaaauggac 180
uauguugcca agguugauga ucuugugagg gcgucgaguu cgauaucgac auuaguggua 240

```
augauggaca aagauauuga ggcagauugu guaaggaaag cugguaguca uacgagaaac    300

cuuuugaggg uuaagcgugg ucuugacaug gucaaaguuc ucuuugaaca gaucauagcu    360

uccgaaggag auaacuccuu gaaggaucca gcaacuaagu cuuaugcuca aguguuugcu    420

ccccaccaug gaugggcuau acggaaagcu guuucucuug ggauguaugc ucuucccaca    480

agggcucacc uacuuaauau gcucaaagag gaugaggcgg cggcuaagau acauaugcaa    540

agcuauguca auucaucggc accauuaauc acguaucuug auaaucuauu ccucuccaag    600

caacucggua uugauuggug a                                              621


<210> SEQ ID NO 48
<211> LENGTH: 530
<212> TYPE: DNA
<213> ORGANISM: Artificial Sequence
<220> FEATURE:
<223> OTHER INFORMATION: Nicotiana sylvestris PDS gene targetng
      construct

<400> SEQUENCE: 48

ccccaaattg gacttgtttc tgccgttaat ttgagagtcc aagctttgga gctcgaggtc     60

ttctttggga actgaaagtc aagatggtca cttgcaaagg aagactccat ggggcataag    120

ttaaggattc gtactcccag tgccatgacc agaagattga caaaggactt taattagaca    180

atacagttaa ctatttggag gcggcgttat tatcatcatc atttcgtact tcctcacgcc    240

caagggcaat cttatgttga agctcaagac ggtttaagtg ttaaggactg gatgagaaag    300

caagctgaga gactttgcat gccgattgtt gaacatattg agtcaaaagg tggccaagtc    360

agactaaact cacgaataaa aaagattttg acagaaaact gaagaacaca tctgataatc    420

tgctcctagc aaagcttttc cctgacgaaa tttcggcaga tcagagcaaa gcaaaaatat    480

tgaagtatca cgttgtctgt tgcttctgta cactaaattt aagatgaagg               530


<210> SEQ ID NO 49
<211> LENGTH: 3020
<212> TYPE: DNA
<213> ORGANISM: Artificial Sequence
<220> FEATURE:
<223> OTHER INFORMATION: T7 driven RNA2 with NSYL PDS targeting
      construct in MCS

<400> SEQUENCE: 49

taatacgact cactatagga taaaacattg cacctatggt gttgccctgg ctggggtatg     60

tcagtgatcg cagtagaatg tactaattga caagttggag aatacggtag aacgtcctta    120

tccaacacag cctttatccc tctccctgac gaggtttttg tcagtgtaat atttcttttt    180

gaactatcca gcttagtacc gtacgggaaa gtgactggtg tgcttatctt tgaaatgtta    240

ctttgggttt cggttcttta ggttagtaag aaagcacttg tcttctcata caaaggaaaa    300

cctgagacgt atcgcttacg aaagtagcaa tgaaagaaag gtggtggttt taatcgctac    360

cgcaaaaacg atggggtcgt tttaattaac ttctcctacg caagcgtcta aacggacgtt    420

ggggttttgc tagtttcttt agagaaaact agctaagtct ttaatgttat cattagagat    480

ggcataaata taatacttgt gtctgctgat aagatcattt taatttggac gattagactt    540

gttgaactac aggttactga atcacttgcg ctaatcaaca tgggagatat gtacgatgaa    600

tcatttgaca agtcgggcgg tcctgctgac ttgatggacg attcttgggt ggaatcagtt    660

tcgtggaaag atctgttgaa gaagttacac agcataaaat ttgcactaca gtctggtaga    720

gatgagatca ctgggttact agcggcactg aatagacagt gtccttattc accatatgag    780
```

```
cagtttccag ataagaaggt gtatttcctt ttagactcac gggctaacag tgctcttggt    840
gtgattcaga acgcttcagc gttcaagaga cgagctgatg agaagaatgc agtggcgggt    900
gttacaaata ttcctgcgaa tccaaacaca acggttacga cgaaccaagg gagtactact    960
actaccaagg cgaacactgg ctcgactttg gaagaagact tgtacactta ttacaaattc   1020
gatgatgcct ctacagcttt ccacaaatct ctaacttcgt tagagaacat ggagttgaag   1080
agttattacc gaaggaactt tgagaaagta ttcgggatta agtttggtgg agcagctgct   1140
agttcatctg caccgcctcc agcgagtgga ggtccgatac gtcctaatcc ctagggattt   1200
aaggacgtga actctgttga gatctctgtg aaattcagag ggtgggtgat accatattca   1260
ctgatgccat tagcgacatc taaatagggc taattgtgac taatttgagg gaatttcctt   1320
taccattgac gtcagtgtcg ttggtagcat ttgagtttcg caatgcacga attacttagg   1380
aagtggcttg acgacactaa tgtgttattg ttagataatg gtttggtggt caaggtacgt   1440
agtagagtcc cacatattcg cacgtatgaa gtaattggaa agttgtcagt ttttgataat   1500
tcactgggag atgatacgct gtttgaggga aaagtagaga acgtatttgt ttttatgttc   1560
aggcggttct tgtgtgtcaa caaagatgga cattgttact caaggaagca cgatgagctt   1620
tattattacg gacgagtgga cttagattct gtgagtaagg ttaccgaatt ctccccaaat   1680
tggacttgtt tctgccgtta atttgagagt ccaagctttg gagctcgagg tcttctttgg   1740
gaactgaaag tcaagatggt cacttgcaaa ggaagactcc atggggcata agttaaggat   1800
tcgtactccc agtgccatga ccagaagatt gacaaaggac tttaattaga caatacagtt   1860
aactatttgg aggcggcgtt attatcatca tcatttcgta cttcctcacg cccaagggca   1920
atcttatgtt gaagctcaag acggtttaag tgttaaggac tggatgagaa agcaagctga   1980
gagactttgc atgccgattg ttgaacatat tgagtcaaaa ggtggccaag tcagactaaa   2040
ctcacgaata aaaaagattt tgacagaaaa ctgaagaaca catctgataa tctgctccta   2100
gcaaagcttt tccctgacga aatttcggca gatcagagca aagcaaaaat attgaagtat   2160
cacgttgtct gttgcttctg tacactaaat ttaagatgaa ggctagaagg cctccatggg   2220
gatccggtac cgagctcacg cgtctcgagg cccgggcatg tcccgaagac attaaactac   2280
ggttctttaa gtagatccgt gtctgaagtt ttaggttcaa tttaaaccta cgagattgac   2340
attctcgact gatcttgatt gatcggtaag tcttttgtaa tttaattttc tttttgattt   2400
tattttaaat tgttatctgt ttctgtgtat agactgtttg agatcggcgt ttggccgact   2460
cattgtctta ccatagggga acggactttg tttgtgttgt tattttattt gtattttatt   2520
aaaattctca acgatctgaa aaagcctcgc ggctaagaga ttgttggggg gtgagtaagt   2580
acttttaaag tgatgatggt tacaaaggca aaaggggtaa aacccctcgc ctacgtaagc   2640
gttattacgc ccgtctgtac ttatatcagt acactgacga gtccctaaag gacgaaacgg   2700
gagaacgcta gccaccacca ccaccaccac gtgtgaatta caggtgacca gctcgaattt   2760
ccccgatcgt tcaaacattt ggcaataaag tttcttaaga ttgaatcctg ttgccggtct   2820
tgcgatgatt atcatataat ttctgttgaa ttacgttaag catgtaataa ttaacatgta   2880
atgcatgacg ttatttatga gatgggtttt tatgattaga gtcccgcaat tatacattta   2940
atacgcgata gaaaacaaaa tatagcgcgc aaactaggat aaattatcgc gcgcggtgtc   3000
atctatgtta ctagatcggg                                               3020
```

<210> SEQ ID NO 50

<211> LENGTH: 6585
<212> TYPE: DNA
<213> ORGANISM: Artificial Sequence
<220> FEATURE:
<223> OTHER INFORMATION: T7 driven truncated PPK20 RNAI consisting of 5' sequence replicase CDS, PUC57 MCS, 3' sequence, ribozyme and NOS terminator
<220> FEATURE:
<221> NAME/KEY: misc_feature
<222> LOCATION: (6125)..(6125)
<223> OTHER INFORMATION: n is a, c, g or t

<400> SEQUENCE: 50
taatacgact cactatagga tggcgaacgg taacttcaag ttgtctcaat tgctcaatgt 60
ggacgagatg tctgctgagc agaggagtca tttctttgac ttgatgctga ctaaacctga 120
ttgtgagatc gggcaaatga tgcaaagagt tgttgttgat aaagtcgatg acatgattag 180
agaaagaaag actaaagatc cagtgattgt tcatgaagtt ctttctcaga aggaacagaa 240
caagttgatg gaaatttatc ctgaattcaa tatcgtgttt aaagacgaca aaaacatggt 300
tcatgggttt gcggctgctg agcgaaaact acaagcttta ttgcttttag atagagttcc 360
tgctctgcaa gaggtggatg acatcggtgg tcaatggtcg ttttgggtaa ctagaggtga 420
gaaaaggatt cattcctgtt gtccaaatct agatattcgg gatgatcaga gagaaatttc 480
tcgacagata tttcttactg ctattggtga tcaagctaga agtggtaaga gacagatgtc 540
ggagaatgag ctgtggatgt atgaccaatt tcgtgaaaat attgctgcgc ctaacgcggt 600
taggtgcaat aatacatatc agggttgtac atgtaggggt ttttctgatg gtaagaagaa 660
aggcgcgcag tatgcgatag ctcttcacag cctgtatgac ttcaagttga aagacttgat 720
ggctactatg gttgagaaga aaactaaagt ggttcatgct gctatgcttt ttgctcctga 780
aagtatgtta gtggacgaag gtccattacc ttctgttgac ggttactaca tgaagaagaa 840
cgggaagatc tatttcggtt ttgagaaaga tccttccttt tcttacattc atgactggga 900
agagtacaag aagtatctac tggggaagcc agtgagttac caagggaatg tgttctactt 960
cgaaccgtgg caggtgagag gagacacaat gctttttttcg atctacagga tagctggagt 1020
tccgaggagg tctctatcat cgcaagagta ctaccgaaga atatatatca gtagatggga 1080
aaacatggtt gttgtcccaa ttttcgatct ggtcgaatca acgcgagagt tggtcaagaa 1140
agacctgttt gtagagaaac aattcatgga caagtgtttg gattacatag ctaggttatc 1200
tgaccagcag ctgaccataa gcaatgttaa atcatacttg agttcaaata attgggtctt 1260
attcataaac ggggcggccg tgaagaacaa gcaaagtgta gattctcgag atttacagtt 1320
gttggctcaa actttgctag tgaaggaaca agtggcgaga cctgtcatga gggagttgcg 1380
tgaagcaatt ctgactgaga cgaaacctat cacgtcattg actgatgtgc tgggtttaat 1440
atcaagaaaa ctgtggaagc agtttgctaa caagatcgca gtcggcggat tcgttggcat 1500
ggttggtact ctaattggat tctatccaaa gaaggtacta acctgggcga aggacacacc 1560
aaatggtcca gaactatgtt acgagaactc gcacaaaacc aaggtgatag tatttctgag 1620
tgttgtgtat gccattggag gaatcacgct tatgcgtcga gacatccgag atggactggt 1680
gaaaaaacta tgtgatatgt ttgatatcaa acgggggggcc catgtcttag acgttgagaa 1740
tccgtgccgc tattatgaaa tcaacgattt ctttagcagt ctgtattcgg catctgagtc 1800
cggtgagacc gttttaccag atttatccga ggtaaaagcc aagtctgata agctattgca 1860
gcagaagaaa gaaatcgctg acgagtttct aagtgcaaaa ttctctaact attctggcag 1920
ttcggtgaga acttctccac catcggtggt cggttcatct cgaagcggac tgggtctgtt 1980
gttggaagac agtaacgtgc tgacccaagc tagagttgga gtttcaagaa aggtagacga 2040
tgaggagatc atggagcagt ttctgagtgg tcttattgac actgaagcag aaattgacga 2100
ggttgttcca gccttttcag ctgaatgtga aagaggggaa acaagcggta caaaggtgtt 2160
gtgtaaacct ttaacgccac caggatttga gaacgtgttg ccagctgtca aacctttggt 2220
cagcaaagga aaaacggtca aacgtgtcga ttacttccaa gtgatgggag gtgagagatt 2280
accaaaaagg ccggttgtca gtggagacga ttctgtggac gctagaagag agtttctgta 2340
ctacttagat gcggagagag tcgctcaaaa tgatgaaatt atgtctctgt atcgtgacta 2400
ttcgagagga gttattcgaa ctggaggtca gaattacccg cacggactgg gagtgtggga 2460
tgtggagatg aagaactggt gcatacgtcc agtggtcact gaacatgctt atgtgttcca 2520
accagacaaa cgtatggatg attggtcggg atacttagaa gtggctgttt gggaacgagg 2580
tatgttggtc aacgacttcg cggtcgaaag gatgagtgat tatgtcatag tttgcgatca 2640
gacgtatctt tgcaataaca ggttgatctt ggacaattta agtgccctgg atctaggacc 2700
agttaactgt tcttttgaat tagttgacgg tgtacctggt tgtggtaagt cgacaatgat 2760
tgtcaactca gctaatcctt gtgtcgatgt ggttctctct actgggagag cagcaaccga 2820
cgacttgatc gagagattcg cgagcaaagg ttttccatgc aaattgaaaa ggagagtgaa 2880
gacggttgat tctttttga tgcattgtgt tgatggttct ttaaccggag acgtgttgca 2940
tttcgatgaa gctctcatgg cccatgctgg tatggtgtac ttttgcgctc agatagctgg 3000
tgctaaacga tgtatctgtc aaggagatca gaatcaaatt tctttcaagc ctagggtatc 3060
tcaagttgat ttgaggtttt ctagtctggt cggaaagttt gacattgtta cagaaaaaag 3120
agaaacttac agaagtccag cagatgtggc tgccgtattg aacaagtact atactggaga 3180
tgtcagaaca cataacgcga ctgctaattc gatgacggtg aggaagattg tgtctaaaga 3240
acaggtttct ttgaagcctg gtgctcagta cataactttc cttcagtctg agaagaagga 3300
gttggtaaat ttgttggcat tgaggaaagt ggcagctaaa gtgagtacag tacacgagtc 3360
gcaaggagag acattcaaag atgtagtcct agtcaggacg aaacctacgg atgactcaat 3420
cgctagaggt cgggagtact taatcgtggc gttgtcgcgt cacacacaat cacttgtgta 3480
tgaaactgtg aaagaggacg atgtaagcaa agagatcagg gaaagtgccg cgcttacgaa 3540
ggcggctttg gcaagatttt ttgttactga gaccgtctta tgacggtttc ggtctaggtt 3600
tgatgtcttt agacatcatg aagggccttg cgccgttcca gattcaggta cgattacgga 3660
cttggagatg tggtacgacg ctttgtttcc gggaaattcg ttaagagact caagcctaga 3720
cgggtatttg gtggcaacga ctgattgcaa tttgcgatta gacaatgtta cgatcaaaag 3780
tggaaactgg aaagacaagt ttgctgaaaa agaaacgttt ctgaaaccgg ttattcgtac 3840
tgctatgcct gacaaaagga agactactca gttggagagt ttgttagcat tgcagaaaag 3900
gaaccaagcg gcacccgatc tacaagaaaa tgtgcacgca acagttctaa tcgaagagac 3960
gatgaagaag ttgaaatctg ttgtctacga tgtgggaaaa attcgggctg atcctattgt 4020
caatagagct caaatggaga gatggtggag aaatcaaagc acagcggtac aggctaaggt 4080
agtagcagat gtgagagagt tacatgaaat agactattcg tcttacatgt atatgatcaa 4140
atctgacgtg aaacctaaga ctgatttaac accgcaattt gaatactcag ctctacagac 4200
tgttgtgtat cacgagaagt tgatcaactc gttgttcggt ccaattttca aagaaattaa 4260
tgaacgcaag ttggatgcta tgcaaccaca ttttgtgttc aacacgagaa tgacatcgag 4320

```
tgatttaaac gatcgagtga agttcttaaa tacggaagcg gcttacgact ttgttgagat   4380
agacatgtct aaattcgaca agtcggcaaa tcgcttccat ttacaactgc agctggagat   4440
ttacaggtta tttgggctag atgagtgggc ggccttcctt tgggaggtgt cgcacactca   4500
aactactgtg agagatattc aaaatggtat gatggcgcat atttggtacc aacaaaagag   4560
tggagatgct gatacttata atgcaaattc agatagaaca ctgtgtgcac tcttgtctga   4620
attaccattg gagaaagcag tcatggttac atatggagga gatgactcac tgattgcgtt   4680
tcctagagga acgcagtttg ttgatccgtg tccaaagttg gctactaagt ggaatttcga   4740
gtgcaagatt tttaagtacg atgtcccaat gttttgtggg aagttcttgc ttaagacgtc   4800
atcgtgttac gagttcgtgc cagatccggt aaaagttctg acgaagttgg ggaaaaagag   4860
tataaaggat gtgcaacatt tagccgagat ctacatctcg ctgaatgatt ccaatagagc   4920
tcttgggaac tacatggtgg tatccaaact gtccgagtct gtttcagacc ggtatttgta   4980
caaaggtgat tctgttcatg cgctttgtgc gctatggaag catattaaga gttttacagc   5040
tctgtgtaca ttattccgag acgaaaacga taaggaattg aacccggcta aggttgattg   5100
gaagaaggca cagagagctg tgtcaaactt ttacgactgg taatatggaa gaaagtcatt   5160
ggtcaccttg aagaagaaga ctttcgaagt ctcaaaattc tcaaatctag gggccattga   5220
attgtttgtg gacggtagga ggaagagacc gaagtatttt cacagaagaa gagaaactgt   5280
cctaaatcat gttggtggga agaagagtga acacaagtta gacgtttttg accaaaggga   5340
ttacaaaatg attaaatctt acgcgtttct aaagatagta ggtgtacaac tagttgtaac   5400
atcacatcta cctgcagata cgcctgggtt cattcaaatc gatctgttgg attcgagact   5460
tactgagaaa agaaagagag gaaagactat tcagagattc aaagctcgag cttgcgataa   5520
ctgttcagtt gcgcagtaca aggttgaata cagtatttcc acacaggaga acgtacttga   5580
tgtctggaag gtgggttgta tttctgaggg cgttccggtc tgtgacggta catacccttt   5640
cagtatcgaa gtgtcgctaa tatgggttgc tactgattcg actaggcgcc tcaatgtgga   5700
agaactgaac agttcggatt acattgaagg cgattttacc gatcaagagg ttttcggtga   5760
gttcatgtct ttgaaacaag tggagatgaa gacgattgag gcgaagtacg atggtcctta   5820
cagaccagct actactagac ctaagtcatt attgtcaagt gaagatgtta agagagcgtc   5880
taataagaaa aactcgtctt aatgcataaa gaaatttatt gtcaatgaat tcgagctcgg   5940
tacctcgcga atgcatctag atatcggatc ccgggcccgt cgactgcaga ggcctgcatg   6000
caagcttttt tattttatat tgttatctgt ttctgtgtat agactgtttg agattggcgc   6060
ttggccgact cattgtctta ccatagggga acggactttg tttgtgttgt tattttattt   6120
gtatntatta aaattctcaa tgatctgaaa aggcctcgag gctaagagat tattgggggg   6180
tgagtaagta cttttaaagt gatgatggtt acaaaggcaa aaggggtaaa accccctcgcc   6240
tacgtaagcg ttattacgcc cgtctgtact tatatcagta cactgacgag tccctaaagg   6300
acgaaacggg cccctcgaat ttccccgatg ggcgttcaaa catttggcaa taaagtttct   6360
taagattgaa tcctgttgcc ggtcttgcga tgattatcat ataatttctg ttgaattacg   6420
ttaagcatgt aataattaac atgtaatgca tgacgttatt tatgagatgg gtttttatga   6480
ttagagtccc gcaattatac atttaatacg cgatagaaaa caaaatatag cgcgcaaact   6540
aggataaatt atcgcgcgcg gtgtcatcta tgttactaga tcggg                   6585
```

<210> SEQ ID NO 51
<211> LENGTH: 5124

<212> TYPE: DNA
<213> ORGANISM: Artificial Sequence
<220> FEATURE:
<223> OTHER INFORMATION: TRV PPK20 RNAI replicase CDS

<400> SEQUENCE: 51
atggcgaacg gtaacttcaa gttgtctcaa ttgctcaatg tggacgagat gtctgctgag 60
cagaggagtc atttctttga cttgatgctg actaaacctg attgtgagat cgggcaaatg 120
atgcaaagag ttgttgttga taaagtcgat gacatgatta gagaaagaaa gactaaagat 180
ccagtgattg ttcatgaagt tctttctcag aaggaacaga acaagttgat ggaaatttat 240
cctgaattca atatcgtgtt taaagacgac aaaaacatgg ttcatgggtt tgcggctgct 300
gagcgaaaac tacaagcttt attgctttta gatagagttc ctgctctgca agaggtggat 360
gacatcggtg gtcaatggtc gttttgggta actagaggtg agaaaaggat tcattcctgt 420
tgtccaaatc tagatattcg ggatgatcag agagaaattt ctcgacagat atttcttact 480
gctattggtg atcaagctag aagtggtaag agacagatgt cggagaatga gctgtggatg 540
tatgaccaat ttcgtgaaaa tattgctgcg cctaacgcgg ttaggtgcaa taatacatat 600
cagggttgta catgtagggg tttttctgat ggtaagaaga aaggcgcgca gtatgcgata 660
gctcttcaca gcctgtatga cttcaagttg aaagacttga tggctactat ggttgagaag 720
aaaactaaag tggttcatgc tgctatgctt tttgctcctg aaagtatgtt agtggacgaa 780
ggtccattac cttctgttga cggttactac atgaagaaga acgggaagat ctatttcggt 840
tttgagaaag atccttcctt ttcttacatt catgactggg aagagtacaa gaagtatcta 900
ctggggaagc cagtgagtta ccaagggaat gtgttctact tcgaaccgtg gcaggtgaga 960
ggagacacaa tgcttttttc gatctacagg atagctggag ttccgaggag gtctctatca 1020
tcgcaagagt actaccgaag aatatatatc agtagatggg aaaacatggt tgttgtccca 1080
attttcgatc tggtcgaatc aacgcgagag ttggtcaaga aagacctgtt tgtagagaaa 1140
caattcatgg acaagtgttt ggattacata gctaggttat ctgaccagca gctgaccata 1200
agcaatgtta aatcatactt gagttcaaat aattgggtct tattcataaa cggggcggcc 1260
gtgaagaaca agcaaagtgt agattctcga gatttacagt tgttggctca aactttgcta 1320
gtgaaggaac aagtggcgag acctgtcatg agggagttgc gtgaagcaat tctgactgag 1380
acgaaaccta tcacgtcatt gactgatgtg ctgggtttaa tatcaagaaa actgtggaag 1440
cagtttgcta acaagatcgc agtcggcgga ttcgttggca tggttggtac tctaattgga 1500
ttctatccaa agaaggtact aacctgggcg aaggacacac caaatggtcc agaactatgt 1560
tacgagaact cgcacaaaac caaggtgata gtatttctga gtgttgtgta tgccattgga 1620
ggaatcacgc ttatgcgtcg agacatccga gatggactgg tgaaaaaact atgtgatatg 1680
tttgatatca aacggggggc ccatgtctta gacgttgaga atccgtgccg ctattatgaa 1740
atcaacgatt tctttagcag tctgtattcg gcatctgagt ccggtgagac cgttttacca 1800
gatttatccg aggtaaaagc caagtctgat aagctattgc agcagaagaa agaaatcgct 1860
gacgagtttc taagtgcaaa attctctaac tattctggca gttcggtgag aacttctcca 1920
ccatcggtgg tcggttcatc tcgaagcgga ctgggtctgt tgttggaaga cagtaacgtg 1980
ctgacccaag ctagagttgg agtttcaaga aaggtagacg atgaggagat catggagcag 2040
tttctgagtg gtcttattga cactgaagca gaaattgacg aggttgttcc agccttttca 2100
gctgaatgtg aaagagggga aacaagcggt acaaaggtgt tgtgtaaacc tttaacgcca 2160

-continued

```
ccaggatttg agaacgtgtt gccagctgtc aaacctttgg tcagcaaagg aaaaacggtc   2220
aaacgtgtcg attacttcca agtgatggga ggtgagagat taccaaaaag gccggttgtc   2280
agtggagacg attctgtgga cgctagaaga gagtttctgt actacttaga tgcggagaga   2340
gtcgctcaaa atgatgaaat tatgtctctg tatcgtgact attcgagagg agttattcga   2400
actggaggtc agaattaccc gcacggactg ggagtgtggg atgtggagat gaagaactgg   2460
tgcatacgtc cagtggtcac tgaacatgct tatgtgttcc aaccagacaa acgtatggat   2520
gattggtcgg gatacttaga agtggctgtt tgggaacgag gtatgttggt caacgacttc   2580
gcggtcgaaa ggatgagtga ttatgtcata gtttgcgatc agacgtatct ttgcaataac   2640
aggttgatct tggacaattt aagtgccctg gatctaggac cagttaactg ttcttttgaa   2700
ttagttgacg gtgtacctgg ttgtggtaag tcgacaatga ttgtcaactc agctaatcct   2760
tgtgtcgatg tggttctctc tactgggaga gcagcaaccg acgacttgat cgagagattc   2820
gcgagcaaag gttttccatg caaattgaaa aggagagtga agacggttga ttcttttttg   2880
atgcattgtg ttgatggttc tttaaccgga gacgtgttgc atttcgatga agctctcatg   2940
gcccatgctg gtatggtgta cttttgcgct cagatagctg gtgctaaacg atgtatctgt   3000
caaggagatc agaatcaaat ttctttcaag cctagggtat ctcaagttga tttgaggttt   3060
tctagtctgg tcggaaagtt tgacattgtt acagaaaaaa gagaaactta cagaagtcca   3120
gcagatgtgg ctgccgtatt gaacaagtac tatactggag atgtcagaac acataacgcg   3180
actgctaatt cgatgacggt gaggaagatt gtgtctaaag aacaggtttc tttgaagcct   3240
ggtgctcagt acataacttt ccttcagtct gagaagaagg agttggtaaa tttgttggca   3300
ttgaggaaag tggcagctaa agtgagtaca gtacacgagt cgcaaggaga gacattcaaa   3360
gatgtagtcc tagtcaggac gaaacctacg gatgactcaa tcgctagagg tcgggagtac   3420
ttaatcgtgg cgttgtcgcg tcacacacaa tcacttgtgt atgaaactgt gaaagaggac   3480
gatgtaagca aagagatcag ggaaagtgcc gcgcttacga aggcggcttt ggcaagattt   3540
tttgttactg agaccgtctt atgacggttt cggtctaggt ttgatgtctt tagacatcat   3600
gaagggcctt gcgccgttcc agattcaggt acgattacgg acttggagat gtggtacgac   3660
gctttgtttc cgggaaattc gttaagagac tcaagcctag acgggtattt ggtggcaacg   3720
actgattgca atttgcgatt agacaatgtt acgatcaaaa gtggaaactg gaaagacaag   3780
tttgctgaaa aagaaacgtt tctgaaaccg gttattcgta ctgctatgcc tgacaaaagg   3840
aagactactc agttggagag tttgttagca ttgcagaaaa ggaaccaagc ggcacccgat   3900
ctacaagaaa atgtgcacgc aacagttcta atcgaagaga cgatgaagaa gttgaaatct   3960
gttgtctacg atgtgggaaa aattcgggct gatcctattg tcaatagagc tcaaatggag   4020
agatggtgga gaaatcaaag cacagcggta caggctaagg tagtagcaga tgtgagagag   4080
ttacatgaaa tagactattc gtcttacatg tatatgatca aatctgacgt gaaacctaag   4140
actgatttaa caccgcaatt tgaatactca gctctacaga ctgttgtgta tcacgagaag   4200
ttgatcaact cgttgttcgg tccaattttc aaagaaatta atgaacgcaa gttggatgct   4260
atgcaaccac attttgtgtt caacacgaga atgacatcga gtgatttaaa cgatcgagtg   4320
aagttcttaa atacggaagc ggcttacgac tttgttgaga tagacatgtc taaattcgac   4380
aagtcggcaa atcgcttcca tttacaactg cagctggaga tttacaggtt atttgggcta   4440
gatgagtggg cggccttcct ttgggaggtg tcgcacactc aaactactgt gagagatatt   4500
caaaatggta tgatggcgca tatttggtac caacaaaaga gtggagatgc tgatacttat   4560
```

```
aatgcaaatt cagatagaac actgtgtgca ctcttgtctg aattaccatt ggagaaagca   4620

gtcatggtta catatggagg agatgactca ctgattgcgt ttcctagagg aacgcagttt   4680

gttgatccgt gtccaaagtt ggctactaag tggaatttcg agtgcaagat ttttaagtac   4740

gatgtcccaa tgttttgtgg gaagttcttg cttaagacgt catcgtgtta cgagttcgtg   4800

ccagatccgg taaaagttct gacgaagttg gggaaaaaga gtataaagga tgtgcaacat   4860

ttagccgaga tctacatctc gctgaatgat tccaatagag ctcttgggaa ctacatggtg   4920

gtatccaaac tgtccgagtc tgtttcagac cggtatttgt acaaaggtga ttctgttcat   4980

gcgctttgtg cgctatggaa gcatattaag agttttacag ctctgtgtac attattccga   5040

gacgaaaacg ataaggaatt gaacccggct aaggttgatt ggaagaaggc acagagagct   5100

gtgtcaaact tttacgactg gtaa                                          5124
```

<210> SEQ ID NO 52
<211> LENGTH: 320
<212> TYPE: DNA
<213> ORGANISM: Artificial Sequence
<220> FEATURE:
<223> OTHER INFORMATION: TRV Ppk20 RNA2 5' replication element containing sequence

<400> SEQUENCE: 52

```
ataaaacatt gcacctatgg tgttgccctg gctggggtat gtcagtgatc gcagtagaat     60

gtactaattg acaagttgga gaatacggta gaacgtcctt atccaacaca gcctttatcc    120

ctctccctga cgaggttttt gtcagtgtaa tatttctttt tgaactatcc agcttagtac    180

cgtacgggaa agtgactggt gtgcttatct ttgaaatgtt actttgggtt tcggttcttt    240

aggttagtaa gaaagcactt gtcttctcat acaaaggaaa acctgagacg tatcgcttac    300

gaaagtagca atgaaagaaa                                                320
```

<210> SEQ ID NO 53
<211> LENGTH: 394
<212> TYPE: DNA
<213> ORGANISM: Artificial Sequence
<220> FEATURE:
<223> OTHER INFORMATION: TRV Ppk20 RNA2 3' replication element containing sequence
<220> FEATURE:
<221> NAME/KEY: misc_feature
<222> LOCATION: (258)..(258)
<223> OTHER INFORMATION: n is a, c, g or t

<400> SEQUENCE: 53

```
atgtcccgaa gacattaaac tacggttctt taagtagatc cgtgtctgaa gttttaggtt     60

caatttaaac ctacgagatt gacattctcg actgatcttg attgatcggt aagtcttttg    120

taatttaatt ttctttttga ttttatttta aattgttatc tgtttctgtg tatagactgt    180

ttgagatcgg cgtttggccg actcattgtc ttaccatagg ggaacggact ttgtttgtgt    240

tgttatttta tttgtatnta ttaaaattct caacgatctg aaaaagcctc gcggctaaga    300

gattgttggg gggtgagtaa gtacttttaa agtgatgatg gttacaaagg caaaaggggt    360

aaaacccctc gcctacgtaa gcgttattac gccc                                394
```

<210> SEQ ID NO 54
<211> LENGTH: 1026
<212> TYPE: RNA
<213> ORGANISM: Arabidopsis thaliana

<400> SEQUENCE: 54
auggcuccga cuuugcaagg ccaguggauc aaggugggc agaaaggagg aacgggacca 60
ggaccuagaa guucacacgg cauagccgcg gucggagaca agcucuacag uuucggcggc 120
gaguuaacac caaacaaaca caucgacaaa gaccucuacg ucuuugacuu caacacucaa 180
acuuggucaa ucgcucaacc caaaggagac gccccaacug uauccugcuu aggcgugcgc 240
augguggccg ugggaacuaa gaucuauauc uuuggaggcc gcgaugagaa ccgcaacuuc 300
gaaaacuuuc gcuccuacga uacggugaca uccgagugga cauuccugac gaagcuugau 360
gaggugggag gacccgaggc ucguacuuuc cauucgaugg cuucggauga aaaccaugug 420
uauguauucg guggggugag caaaggcggu acuaugaaua cucccacgcg guucaggaca 480
aucgaggcgu auaacauugc ugaugggaaa ugggcucagc uaccggaucc aggagauaac 540
uucgagaaaa gaggaggagc gggauucgcu gugguacaag ggaagauuug ggugguuuau 600
ggguuugcga ccucgauugu gcccggaggc aaagaugacu augagucuaa ugcugugcaa 660
uucuaugauc cggcuuccaa aaaguggacc gaaguagaga cuacaggagc gaaaccuucc 720
gcaaggagcg uguuugccca ugcgguagug ggaaaguaua uaauaauauu ugcaggugag 780
guauggccug aucucaaugg gcauuauggu cccgggacgc uguccaauga gggauaugcg 840
uuggacaccg agacacuggu gugggaaaag uugggagaag aaggugcacc agccauacca 900
cgagguugga cugccuauac ugcugccacu gucgauggaa agaauggccu ccucaugcau 960
ggcggaaagc uuccgaccaa cgagcgaacu gaugaucucu acuucuaugc ggucaauuca 1020
gcuuaa 1026

<210> SEQ ID NO 55
<211> LENGTH: 1041
<212> TYPE: RNA
<213> ORGANISM: Arabidopsis thaliana

<400> SEQUENCE: 55
auggcuuuaa aacauaugca aaucuuucuc uucgucgcua uauuuucauc auucuguuuc 60
uccaucacuc uuucucgucc acucgacaau gaacucauca ugcaaaagag gcacaucgag 120
uggaugacua aacacggccg ugucuacgcg gaugugaagg aggaaaacaa ucgcuacguu 180
guguucaaaa acaacgucga acgcauugaa cauuuaaaua gcauucccgc cggaagaacu 240
uucaaacuug cgguaaauca guuugcugau uuaaccaaug acgaauuucg uuccauguac 300
acugguuuca aaggugucuc ggcauuaucu agccaaagcc aaacuaaaau gucgccguuu 360
agguaccaaa acguuucuuc uggugcuuug ccgguuucug uugacuggag gaagaaagga 420
gcugugaccc cuaucaagaa ucaaggcagc ugcggauguu guugggcguu uucagcgguu 480
gcggcuauug aaggagcaac acaaauaaag aaagggaaac uuauaucuuu gucagaacaa 540
cagcuuguug auugcgacac aaacgauuuu ggcugcgaag gcgguuuaau ggauacugcg 600
uuugagcaua uaaaagcgac uggcggcuug acaacugagu caaauuaucc uuacaaaggc 660
gaagacgcua cuugcaauuc caaaaagacc aauccaaaag caacuucuau uacagguuau 720
gaggaugucc cgguuaauga ugagcaagca cugaugaagg caguggcaca ccaaccgguu 780
agcguuggaa uugaaggagg ugguuuugau uuccaauucu auucgucugg uguguucacu 840
ggagagugca cuacguaucu ugaucaugca guaacugcga uuggauacgg cgaaucuacu 900
aacggaucaa aguauuggau caucaagaau ucaugggga caaaaugggg agaaagugga 960
uauaugagga uucaaaaaga ugucaaggau aaacaaggac uauguggucu ugccaugaaa 1020
gcuucuuacc caacuauaug a 1041

<210> SEQ ID NO 56
<211> LENGTH: 1626
<212> TYPE: RNA
<213> ORGANISM: Arabidopsis thaliana

<400> SEQUENCE: 56
auggacgauu gucgauucga gacgagugag uugcaagcuu cgguaaugau aucgacuccu 60
uuauuuaccg auucuuggag uucaugcaac accgcaaauu gcaacgggag uauaaagauc 120
caugacaucg ccgggauuac auacguugcu auaccggcgg uaucgaugau ucaguugggg 180
aaucuugugg gcuugccagu caccggagau guucuuuucc ccggcuuauc cuccgaugaa 240
ccucuaccua uggucgacgc ugccauacuc aaacucuuuc uucaguuaaa gaucaaggaa 300
ggauuggaau uggaauuguu agguaaaaag cugguggaga uaaccggcca uucaaccggc 360
ggcgcauugg ccgcuuucac cgcacuuugg cuucuaucuc aaucuucucc gccgucauuc 420
cgcgucuuuu guaucaccuu uggcucuccu cugcucggaa accaaucucu cuccaccuca 480
auuucacgau cacguuuagc acacaacuuc ugccacgugg ucuccaucca cgaccucguu 540
ccuagaagca gcaaugaaca auucuggccc uuuggaacuu acuuguucug uuccgacaaa 600
ggaggugucu gucuagacaa cgcugguucu guucgucuga uguuuaauau ccucaacacc 660
acagcaacuc aaaacaccga ggaacaucag agguacggac acuauguguu cacacuuuca 720
cacauguuuc uuaaaucuag aagcuuucuu gguugggagua ucccgacaa uagcuaccaa 780 gcugguguug cguuagccgu ugaagcucua gguuucucua acgaugacac aaguggcguu 840
uuagucaaag aauguauaga aacagcuaca agaauuguuc gggcuccuau ucugagguca 900
gcugaguuag ccaaugagcu ugcuagugus uugccagcaa gacucgagau ucaaugguac 960
aaagaucguu gcgaugcauc agaagagcag cuagguuacu acgauuucuu caaacgauau 1020
ucguugaaga gagacuuuaa agugaacaug agucgcauaa gacuagcuaa guuuugggac 1080
acagugauua aaauggugga gacgaaugag uuaccuuuug auuuucauuu aggaaagaaa 1140
uggauuuacg caucucaauu uuaucaacuc uuagccgagc cacucgacau ugcgaauuuc 1200
uacaaaaaca gagauauaaa gacuggcggg cauuacuugg aggggaauag accuaaaagg 1260
uaugagguga uugauaaaug gcagaaagga guuaaagugc cugaggagug ugugagaagc 1320
agauacgcga gcacaacgca agauacuugc uuuugggcua agcuugagca agcaaaagag 1380
ugguuggaug aggcgagaaa agagaguagu gauccccaga ggagaucuuu guuacgggaa 1440
aagauuguuc cauucgagag uuaugcgaau acauuggug cgaagaagga gguuucuuug 1500
gauguuaaag cgaagaacuc gaguuauagu gugugggagg cgaaucugaa agaguucaag 1560
ugcaaaaugg guuaugaaaa ugaaauugag augguuguug augagaguga cgcaauggag 1620
acuuag 1626

<210> SEQ ID NO 57
<211> LENGTH: 2420
<212> TYPE: RNA
<213> ORGANISM: Arabidopsis thaliana

<400> SEQUENCE: 57
auggaagccc uccuccuccc uccuucgccg gaaccccaaa aucaaaucac caauccggcg 60
aauucaaagc caaaucauca aucuggugac guacauaaag augagacgau gaugaugaag 120

-continued aagaagaagg auacgaaucc aucgaauuug gaaaagagaa aacucaaggg aaagaagaaa 180
gagauuaugg acaacgacga agcuucuucg uccuauuguu cuacaucuuc uaccucuaau 240
ucaaauucua cuaaaagggu uacgagagug guucauagau uacgaaaccc uaugcgguua 300
gguauggcuc gacgaagcgu uggugaacga caagcugaaa aauuggcgaa gccucugggc 360
uuuucacuug ccgcuuuugc uaauauggau auugcgagaa agaaugccgc aggucagaau 420
guuuauguug augaucuugu ugagaucuuu gcuacucuug ucgaagaauc auuagccaau 480
guuuauggua auaagcuugg uuccuuugcg accaacuuug agcaaacauu cagcaguacu 540
cuaaagaucc uuaaaauugac caaugaaugu gcaaauccac aucagucaaa caauaaugau 600
gguggagauu guaauuuaga ucgcucuacc auagacggau gcucagacac cgagcuauuu 660
gagagggaga cuucaucugc uacgucugcu uaugaaguga ugcaaggcag ugcaacagca 720
accucuuuga ugaaugagcu ugcccuuuuc gaagagacuc uacaacucuc uugugucccu 780
ccuagaaguu cagcaauggc uuugaccaca gacgaaaggu uuuuaaaaga gcaaacacga 840
gcaaacgacc uaaagaccgu ggagauuggu cuucaaauaa gagaguuaag gugcaaagag 900
acggcgcuag gauuaaaauu ugaaucaaac aaccuggga aagcggcgcu agaguuggau 960
guuucgaaag cugcauucag agcggagaaa uucaaaaccg aauuagaaga uacaaggcaa 1020
gagauguccu agguggaaag guagcugcau ggaaagauga ugauggagau ugguaugaga 1080
cuggguugca cauauucuuu ggggcuuacc caaauaugca gaaccuguuu ggagaacuag 1140
ggauaaauga ucgguugcag uggaaggaac auucaaugau auuugcgaug ccuaacaagc 1200
caggggaguu cagccgcuuu gauuuuccug aagcucuucc ugcgccauua aauggaauuu 1260
uggccauacu aaagaacaac gaaaugcuua cguggcccga aaaagucaaa uuugcuauug 1320
gacucuugcc agcaaugcuu ggagggcaau cuuauguuga agcucaagac gguuuaagug 1380
uuaaggacug gaugagaaag caaggugugc cugauagggu gacagaugag guguucauug 1440
ccaugucaaa ggcacuuaac uucauaaacc cugacgagcu uucgaugcag ugcauuuuga 1500
uugcuuugaa cagauuucuu caggagaaac augguucaaa aauggccuuu uuagauggua 1560
acccuccuga gagacuuugc augccgauug uugaacauau ugagucaaaa gguggccaag 1620
ucagacuaaa cucacgaaua aaaaagauug agcugaauga ggauggaagu gucaaauguu 1680
uuauacugaa uaauggcagu acaauuaaag gagaugcuuu uguguuugcc acuccagugg 1740
auaucuucaa gcuucuuuug ccugaagagu ggaaagagau cccauauuuc caaaaguugg 1800
agaagcuagu gggaguuccu gugauaaaug uccauauaug guuugacaga aaacugaaga 1860
acacaucuga uaaucugcuc uucagcagaa gcccauugcu caguguguau gcugacaugu 1920
cuguuacaug uaaggaauau uacaacccca aucagucuau guuggaauug guauuugcac 1980
cugcagaaga guggauaaau cguagugacu cagaaauuau ugaugcuaca augaaggaac 2040
uagcaaagcu uuucccugac gaaauuucgg cagaucagag caaagcaaaa auauugaagu 2100
aucacguugu caaaacucca aggucuguuu auaaaacugu gccagguugu gaacccuguc 2160
ggcccuugca aagaucuccu auugaggggu uuuauuuagc uggugacuac acaaaacaga 2220
aauacuuggc uucaauggaa ggugcugucu uaucaggaaa gcuuugugcc caagcuauug 2280
uacaggauua cgaguuacuu cuuggccgga gccagaagaa guuggcagaa gcaagcguag 2340
uuuagcaugg ugaacuaaaa uguugcuucu guacacuaaa uuuaagauga aggcggccac 2400
acugaauuag cguuguacac 2420

<210> SEQ ID NO 58
<211> LENGTH: 1614
<212> TYPE: RNA
<213> ORGANISM: Arabidopsis thaliana

<400> SEQUENCE: 58
augucaguag uuuuacucuc uucuacuucu gcaacaauca ccaaauccca auccaaaaag 60
auucccuuuu uaucucccac cacaaaauuc ccauuaaagg ucucaauuuc uccaucaaga 120
ucgaaacuuu uccacaaccc uuuacgcgug gcggcgccgc cgucuguacc cacuucggau 180
ucgacggagg agaagcggau cgaagaagaa uacggcggag auaaggaaga agaagggucu 240
gaguuuaagu ggagagauca uugguaucca guuucuuugg uugaggauuu ggauccgaau 300
gugccaaccc cguuccagcu cuugggucga gaccuuguac ucugguuuga ucggaaugau 360
cagaaauggg cagccuuuga ugaucucugc ccucaccggc ucgcuccuuu aucugaagga 420
agguuggaug agaauggaca cuugcaaugu ucguaucaug gauggucauu uggugggugu 480
ggaucuugca cuaggauucc ucaggcugcu acuucagguc cugaagcucg ugcuguuaaa 540
uccccgagag cuugugcuau uaaguucccg acaauggugu cucaaggucu ucucuuugug 600
uggccugaug aaaaugguug ggauagagcc aauucaauug aacccccuag guugccggau 660
gauuucgaua aaccggaauu uucgacggug acaauucaaa gggaucuuuu cuauggauau 720
gauacucuca uggaaaaugu aucugauccu ucccauauag auuuugcuca ucacaagguu 780
acaggaagaa gagacagagc caaaccauug ccguucaagg uggagucaag ugggccuugg 840
gguuuccaag gugcgaauga ugacagucca aggauaaccg caaaauuugu ugcuccgugc 900
uauucuauga acaaaauuga guuagaugcg aaacuaccaa ucgucgguaa ucaaaaaugg 960
gucauuugga uuugcucauu caauauacca auggcuccag gaaagacccg uuccaucguu 1020
ugcagcgccc guaacuucuu ucaguucucu guaccaggac cagcuuggug gcagguugua 1080
ccaagauggu augaacacug gacuucgaac uuagucuaug acggagacau gaucguacuu 1140
caaggacaag agaaaguauu ccucgcuaaa ucaauggagu caccagacua cgacgugaac 1200
aaacaguaca caaagcucac auucacucca acccaggcag accguuuugu ucuagcauuc 1260
agaaacuggc ucagacggca ugguaagagu cagccugaau gguucggcuc caccccgucu 1320
aaccaaccuc ucccuuccac ugucuuaacc aagcgucaga ugcuagauag auuugaucag 1380
cauacacaag uaugcucuuc cugcaaagga gcuuacaaca guuuccaaau ccucaagaag 1440
uuucucguug gcgcgacggu uuucugggcc gccacggcug guguuccuuc ugauguucag 1500
auucgacugg uucuugcugg uuuaucacug auaucagcug cuucugcaua ugcuuuacau 1560
gaacaagaga agaacuuugu guuuagagau uauguacauu cugaaaucga guag 1614

<210> SEQ ID NO 59
<211> LENGTH: 2880
<212> TYPE: RNA
<213> ORGANISM: Arabidopsis thaliana

<400> SEQUENCE: 59
augaugaaga aggggaaagg aaagaacagu ggcuuguuac cgaauuccuu uaagauuaua 60
ucuucuugcc uuaaaacugu aucggcuaac gccaccaacg uugcgucguc uguucguucc 120
gcuggugccu ccguugcugc uucaauuucc gcugcugaag augauaagga ucaggugacc 180
ugggcuggau uuggcauucu ugaacugggu caacauguca ccagacaugu ucucuuacuc 240
gguuaucaga auggcuuuca agucuuugau guugaggaug ccucuaauuu uaaugaacug 300

-continued

```
gucucuaaac gagguggucc aguuucauuc uuacagaugc agccauuacc ugcaaggucu    360
ggugaucaug aggguuuuug gaacucacau ccucuuuugc ugguuguugc uggggaugaa    420
acaaauggca cugguuuggg ucacaguuuu ucccagaaug guucauuagc aagagauggu    480
aguucagacu cuaaagccgg ggaugccauc aauuauccua ccacuguucg cuucuacucc    540
cuuagguccc acaguuaugu auauguccug agauuucggu caucuguuug caugauuaga    600
ugcagcuccc gaguagucgc uguuggccuu gcgaaucaaa uauauugugu ugacgcacuu    660
acucuggaaa auaaguucag uguucucacu uauccugucc cccagccagu gagacaaggg    720
acaaccagag uuaauguugg cuauggucg auggcuguag guccaaggug gcuugcauau    780
gcguccaaaa guuccaugac caugaaaaca gggcgccuaa gcccacagac guuuacuucu    840
ucacccaguc ucagcccaag uucaucauca gguggaagca guuuuauggc ccguuaugcc    900
auggagucua gcaagcaguu agccaaugga uuaaucaacc ugggggacau gggauacaaa    960
acauugucaa aauacuguca agauaugcuc ccugauggau cuacuucucc agcaucacca   1020
aaugcaaucu ggaaaguugg ugggguuucu ggaucagaug cagagaaugc cggaaugguu   1080
gcuguuaaag aucuuguuuc uggagcuuua guaucacagu ucaaggcuca uacgaguccu   1140
aucucagcac uuuguuuuga uccuagugga acucuauugg uuacugcuuc aguauguggg   1200
aacaauauca augucuuuca gaucaugcca ucucguucac auaaugcacc uggugaccua   1260
aguuaugagu gggaaucuuc ucaugugcau cucuucaaac ugcauagagg gaucacuuca   1320
gcuauugucc aggacauuug cuuuagucag cagagucagu ggguugcuau uauuucaucc   1380
aaggguacuu gccauauauu uguuuuaaac ucuucuggua gcgacgcugc guuucaaccu   1440
ugcgagggug aggagccuac ccgacuacca gcuucauccu ugccauggug guuuacucaa   1500
ucguugucaa guaaucagca gucuuuaucg ccaccaacag cuguugcccu uucuguugua   1560
agcagaauaa aguauagcag uuuugggugg cuuaacacag uaagcaaugc uacuacugcu   1620
gcuacuggaa aaguuuuugu accaucaggu gccguggcug cuguuuuuca uaaaucuguc   1680
acucaugacc uucagcugaa cucccggacu aacgcguugg agcauaucuu agucuauacu   1740
ccaucaggcc augugguca gcaugaacuu cugccaucag uuugcacaga aucaccugaa   1800
aaugguuuga gagugcaaaa aacaucacau guucaaguuc aggaggauga uuugaggguc   1860
aaaguugagc cuauucagug gugggaugua uguagaaggu cugacuggcu agagacugag   1920
gaacgacuuc ccaaaaguau cacugaaaag caauaugauu uagagacagu gucgaaucac   1980
uugacaagcc augaggaugc augucuuucc cuugacauga acagccauuu uagugaagau   2040
aaguauuuga aaagcuguuc ugagaagccc ccugaaagau cacauugcua ucuuucuaac   2100
uuugagguaa agguuaccuc ggggaugcua ccagugugc aaaauucaaa gauuucuuuu   2160
cauguuaugg auucuccaag agauaguagu uccacuggug gagaguuuga gauagaaaag   2220
guuccggccc augaacuuga aauaaaacag aaaaagcugc ugccaguuuu ugaccauuuc   2280
cacagcacca aagcaacguu ggaagacagg uuuucaauga aaugcuauca cacauccgca   2340
acgggaucuc aucaaguuaa uggaaaaaua ugccaagaua uuaucaacug ucacucuaag   2400
ccaggaucaa uugaguccgc cgaaaguucu gaagaggguu caacaaaaca gauggagaau   2460
cuccaugauu cggaucauau gagcaacuca aucaagucuu cuuuaccccu uuacccaaca   2520
guaaauggga ucuacaagga aauagagaag aacaacgcaa augggguggau ggagaaaccc   2580
guaacagcca aacucucuac acucaaagaa acccggauca caaaugguuu uaccacacca   2640
ccuauacuca ccgauagugu caacgaacag augcucucua caggaaaacc uccuaugggc   2700
```

uuugguuuug cuuugcauga ggagcacugu aaagcaguag cagauccaaa agaagaacac 2760
cugaaaaaga aguuagauga aguuacuaau guucaucacu uaaacgucaa caacaacaac 2820
acagagaaac uacaaggaga caaaauggua caugguaugg uuuccuuugu aggugauuaa 2880

<210> SEQ ID NO 60
<211> LENGTH: 21
<212> TYPE: RNA
<213> ORGANISM: Artificial Sequence
<220> FEATURE:
<223> OTHER INFORMATION: Actin 2 siRNA-A antisense strand

<400> SEQUENCE: 60
ggcaucacac uuucuacaau u 21

<210> SEQ ID NO 61
<211> LENGTH: 21
<212> TYPE: RNA
<213> ORGANISM: Artificial Sequence
<220> FEATURE:
<223> OTHER INFORMATION: Actin 2 siRNA-B antisense strand

<400> SEQUENCE: 61
cgagaagaac uaugaauuau u 21

<210> SEQ ID NO 62
<211> LENGTH: 21
<212> TYPE: RNA
<213> ORGANISM: Artificial Sequence
<220> FEATURE:
<223> OTHER INFORMATION: CHI1 siRNA-A antisense strand

<400> SEQUENCE: 62
ggagauagag gaacuggaau u 21

<210> SEQ ID NO 63
<211> LENGTH: 21
<212> TYPE: RNA
<213> ORGANISM: Artificial Sequence
<220> FEATURE:
<223> OTHER INFORMATION: CHI1 siRNA-B antisense strand

<400> SEQUENCE: 63
ggaacaucuu cuucugcaau u 21

<210> SEQ ID NO 64
<211> LENGTH: 21
<212> TYPE: RNA
<213> ORGANISM: Artificial Sequence
<220> FEATURE:
<223> OTHER INFORMATION: 18S siRNA-A antisense strand

<400> SEQUENCE: 64
gggagguagu gacaauaaau u 21

<210> SEQ ID NO 65
<211> LENGTH: 21
<212> TYPE: RNA
<213> ORGANISM: Artificial Sequence
<220> FEATURE:
<223> OTHER INFORMATION: 18S siRNA-B antisense strand

<400> SEQUENCE: 65
ggacgcauuu auuagauaau u 21

-continued

<210> SEQ ID NO 66
<211> LENGTH: 23
<212> TYPE: DNA
<213> ORGANISM: Artificial Sequence
<220> FEATURE:
<223> OTHER INFORMATION: Actin 2 DNA encoding siRNA-A antisense strand

<400> SEQUENCE: 66
aaggcatcac actttctaca att 23

<210> SEQ ID NO 67
<211> LENGTH: 23
<212> TYPE: DNA
<213> ORGANISM: Artificial Sequence
<220> FEATURE:
<223> OTHER INFORMATION: Actin 2 DNA encoding siRNA-B antisense strand

<400> SEQUENCE: 67
aacgagaaga actatgaatt att 23

<210> SEQ ID NO 68
<211> LENGTH: 23
<212> TYPE: DNA
<213> ORGANISM: Artificial Sequence
<220> FEATURE:
<223> OTHER INFORMATION: CHI1 DNA encoding siRNA-A antisense strand

<400> SEQUENCE: 68
aaggagatag aggaactgga att 23

<210> SEQ ID NO 69
<211> LENGTH: 21
<212> TYPE: DNA
<213> ORGANISM: Artificial Sequence
<220> FEATURE:
<223> OTHER INFORMATION: CHI1 DNA encoding siRNA-B antisense strand

<400> SEQUENCE: 69
aaggaacatc ttcttctgca a 21

<210> SEQ ID NO 70
<211> LENGTH: 23
<212> TYPE: DNA
<213> ORGANISM: Artificial Sequence
<220> FEATURE:
<223> OTHER INFORMATION: 18S DNA encoding miRNA-A antisense strand

<400> SEQUENCE: 70
aagggaggta gtgacaataa att 23

<210> SEQ ID NO 71
<211> LENGTH: 23
<212> TYPE: DNA
<213> ORGANISM: Artificial Sequence
<220> FEATURE:
<223> OTHER INFORMATION: 18S DNA encoding siRNA-B antisense strand

<400> SEQUENCE: 71
aaggacgcat ttattagata att 23

FORMULATION AND METHODS FOR CONTROL OF WEEDY SPECIES

BACKGROUND OF THE INVENTION

The present technology is directed to a formulation and a method for controlling growth of plant species. More specifically, it is a formulation comprising a targeting construct and RNAi inducer to produce small interfering RNAs for use in non-stable expression in weedy plant species. Targeting constructs are designed to target endogenous genes in the weedy species while having no effect in off-target species.

DESCRIPTION OF THE RELATED ART

The impact of invasive and pest plant species has been called an "invisible tax" on our environment and economy. With ever increasing global transportation and travel has come an unprecedented spread of invasive and noxious plant species throughout the world. These weeds adapt quickly to new environments and go largely unchallenged by local flora and fauna. Many are unreachable by or have developed resistance to conventional control techniques. Invasive species cause direct economic losses in sectors such as forestry, ranching, and agriculture.

The current strategies for invasive species management consist of the application of different combinations of chemical herbicides and physical removal, coupled with bio-control techniques as available. The available chemicals are often toxic to a wide array of native plants, animals and insects and can have negative consequences for human health. Many cannot be used in riparian or aquatic environments as the compounds would quickly spread. In addition, they have a limited half-life and efficacy and must be reapplied year after year. Bio-control and physical removal are costly and labour intensive requiring large investments and again, often resulting in collateral damage to other organisms. Some invasive pest plants are now so well established that they are widely considered impossible to remove by any available technique, for example, Eurasian Milfoil. Others, having been subjected to years of treatment with chemicals, have developed resistance to them.

In an attempt to target the species of interest and reduce the damage done by spraying with broad spectrum herbicides, U.S. Pat. No. 7,805,884 discloses an injector system for injecting a dose of weed-killing fluid into the stem of a Japanese knotweed, including a fluid dispenser system with a fluid passage, a collared needle with a fluid delivery aperture in communication with the fluid dispenser system, and an actuator connected to the fluid dispenser system for actuating the transmission of fluid from the fluid dispenser system to the fluid delivery aperture. This employs chemical herbicides.

Control of insect pests is largely through the use of chemical insecticides. Some biological control methods also exist, for example, the use of pheromones in insect traps. These are relatively labour intensive as the traps have to be baited, set and removed.

Another example of biological control is the use of *Bacillus thuringiensis* toxin. It can be provided as a spray or produced in transgenic plants. In transgenic plants, the gene or genes are expressed in the plant, the plant produces the toxin, the foraging insect ingests the plant material and is killed. One could argue that these are quasi-chemical control methods, as toxic chemicals are still being produced and used to kill the insect pests.

Rather than using toxins, U.S. Pat. No. 7,943,819 provides methods for genetic control of insect infestations in plants and compositions thereof by inhibiting one or more biological functions by feeding one or more recombinant double stranded RNA molecules to the insect pest. This reportedly results in a reduction in pest infestation through suppression of gene expression.

U.S. Pat. No. 8,148,604 discloses methods and materials for conferring insect pest resistance to plants and controlling parasitic plant pests. Plants are stably transformed with a silencing construct homologous to a gene of a plant pest that is essential for the survival, development, or pathogenicity of the pest. This results in the plant producing RNA interference (RNAi), specifically short interfering RNA (siRNA) to the selected gene, which, when ingested by the insect pest results in silencing of the gene and a subsequent reduction of the pest's ability to harm the plant. In other embodiments, the pest's reduced ability to harm the plant is passed on to pest progeny. It is also suggested that parasitic plants pests, for example striga, dodder and mistletoe can also be controlled by stably transforming plants with a silencing construct homologous to a gene of the parasitic plant that is essential for survival or development.

Without being bound by theory, RNA interference (RNAi) is considered to be an ancient defense mechanism wherein the host organism recognizes as foreign a double-stranded RNA molecule and hydrolyzes it. The resulting hydrolysis products are small RNA fragments of 21-30 nucleotides in length, called siRNAs. The siRNAs then diffuse or are carried throughout the host, where they hybridize to the complementary Viral RNA or complementary endogenous polynucleotide sequences where they act as guides for RISC mediated hydrolysis and thus knock-down or dysregulation.

For example, the different Dicer-Like proteins (DCL) of *Arabidopsis* cleave dsRNA molecules into different sized (21-25 nt) small dsRNA products depending on which DCL is processing them. *Arabidopsis* encodes 10 Argonaute proteins (AGO1-10) which bind these small RNAs and, as a part of RISC, elicit different effects depending on which AGO the small RNA has been recruited into and the size of the recruited small RNA. AGO1 is largely responsible for the miRNA pathway and also post transcriptional gene silencing. The pathway it is involved in has been shown to result in both targeted degradation of mRNAs and transitivity (RNA-dependent RNA polymerase (RdRP) dependent generation of 2° siRNA products and amplification of the initial signal). It has previously been found that AGO1 prefers to recruit small dsRNAs that are 21 nt in length with a 2 nt, 3' overhang on each end and will prefer sequences with a 5' terminal U as the guide strand (the strand that is responsible for guiding complementary base pairing to a target mRNA sequence) (Mi et al. 2008. Sorting of small RNAs into *Arabidopsis* Argonaute Complexes Is Directed by the 5' Terminal Nucleotide. DOI 10.1016/j.cell.2008.02.034.)

A species-specific herbicide that can be used to kill, weaken or impair growth of a weed species is needed. This is accomplished through miRNA, siRNA, DNA, or single- or double-stranded RNA designed to elicit an RNAi response that spreads systemically once inside a plant cell (RNAi Payload). The RNAi inducer elements cause the payload to be processed producing siRNAs. A region of the RNAi payload contains sequence complementary to endogenous target genes (Targeting construct). siRNAs produced from this region direct the knock-down of those genes leading to cell death. This knock-down is strengthened by RdRP mediated transitivity, phasing, and systemic spread. The result is a herbicide that can be tuned to affect any number of plant species.

SUMMARY OF THE INVENTION

The present technology provides a non-chemical herbicide that can be used to kill, weaken or impair growth of weedy species. In general, the formulation is for application to a host plant to reduce, inhibit or impair one or more of growth and development of the host plant. The formulation comprises an interfering Ribonucleic Acid (RNAi) payload, and at least one of a liquid carrier, a surfactant, a binder and tackifier, a thickener, a colourant, a spreader, an antifreezing agent, a sticker, an anticaking agent, a stabilizer, a disintegrator, an emulsifier, a synergistic compound, an abrasive, an emulsifier, a penetrating agent and a preservative.

In the formulation, the RNAi payload may comprise an at least one sequence specific to the host plant.

The RNAi payload comprises at least 20 contiguous nucleotides of at least one sequence selected from the group consisting of SEQ ID NOs 1 to 66.

The formulation may comprise an RNAi payload, the liquid carrier and the surfactant. It may further comprise the abrasive and still further comprise a synergistic compound.

The formulation is in an exemplary embodiment, for stem injection, and comprises the liquid carrier and the penetrating agent.

A method of inhibiting or impairing plant growth and development is also provided. The method comprises delivering a formulation to a host plant, by spraying, imbibing, irrigating, or injecting the formulation, the formulation comprising an interfering Ribonucleic Acid (RNAi) payload, an at least one of a liquid carrier, a surfactant, a binder and tackifier, a thickener, a colourant, a spreader, an antifreezing agent, a sticker, an anticaking agent, a stabilizer, a disintegrator, an emulsifier, a synergistic compound, an abrasive, an emulsifier, a penetrating agent and a preservative, thereby inhibiting or impairing growth and development. The method comprises delivering the formulation to at least one of a leaf, a root, a stem, a petiole, a seed and a cotyledon. The RNAi payload may comprise a sequence selected from the group consisting of SEQ ID NOs 1 to 66.

The method comprises injecting the stem or petiole or spraying the host plant.

The method further comprises inducing expression of any of SEQ ID NOs 7, 8, 9, 10, 11 and 12 thereby producing any of SEQ ID NOs 1, 2, 3, 4, 5, and 6.

A method of weed control is also provided, the method comprising:

selecting a weed plant species to be controlled;

synthesizing or obtaining at least one RNAi or RNAi encoding sequence;

formulating a species-specific RNAi payload; and delivering the species-specific RNAi payload to the weed plant species while minimally impacting an at least one other plant species.

The RNAi payload comprises at least 20 contiguous nucleotides from or complementary to one or more of SEQ ID NOs 1 to 66.

The method may involve spraying the weed plant species or injecting the weed plant species A method of designing a species-specific construct for RNAi suppression of growth of a target plant species is also provided, the method comprising the steps of:

selecting a suitable gene for growth suppression;

identifying an at least one target site accessible to base pairing in the suitable gene;

identifying an at least one divergent site in the at least one target site;

designing a construct complementary to the at least one divergent site; and adding an at least one RNAi inducer element to the construct, thereby designing a species-specific gene construct for siRNA suppression of growth of the target plant species.

The method may further comprise adding an at least one helper sequence to the species specific gene construct.

The method may further comprise sequencing an at least one gene from the target plant to select the suitable gene.

In the method, the construct may include any one of SEQ. ID No. 1 to 66 or their complement.

A method of inhibiting or impairing plant growth and development of a target plant is also provided, the method comprising:

selecting a suitable gene for growth suppression;

identifying an at least one target site accessible to base pairing in the suitable gene;

identifying an at least one divergent site in the at least one target site;

designing a construct complementary to the at least one divergent site;

adding an at least one RNAi inducer element to the construct; and delivering the construct to the target plant.

The method may further comprise adding an at least one helper sequence to the species specific gene construct.

The method may further comprise sequencing an at least one gene from the target plant to select the suitable gene.

In the method, the construct may include any one of SEQ ID No. 1 to 66 or their complement.

DESCRIPTIONS OF THE PREFERRED EMBODIMENTS

Brief Description of the Sequences

Figure 1:
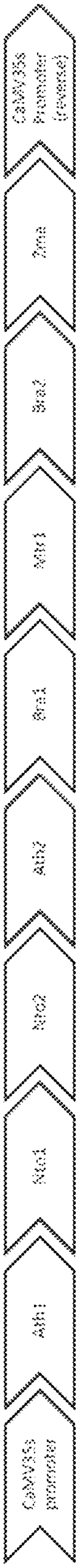
FIG. 1 shows a DPC targeting construct for photobleaching-based death in multiple species in accordance with an embodiment of the technology. Ath=*Arabidopsis thaliana*, Nto=*Nicotiana* tobacum, Bra=*Brassica napus*, Zma=*Zea mays*, Mtr=*Medicago truncatula.*

SEQ ID NO: 1 is the short interfering sequence Actin 2 siRNA-A used according to the present technology.

SEQ ID NO: 2 is the short interfering sequence Actin 2 siRNA-B used according to the present technology.

SEQ ID NO: 3 is the short interfering sequence CHLI siRNA-A used according to the present technology.

SEQ ID NO: 4 is the short interfering sequence CHLI siRNA-B used according to the present technology.

SEQ ID NO: 5 is the short interfering sequence 18S siRNA-A used according to the present technology.

SEQ ID NO: 6 is the short interfering sequence 18S siRNA-B used according to the present technology.

SEQ ID NO: 7 is the DNA sequence encoding the short interfering sequence Actin 2 siRNA-A used according to the present technology.

SEQ ID NO: 8 is the DNA sequence encoding the short interfering sequence Actin 2 si RNA-B used according to the present technology.

SEQ ID NO: 9 is the DNA sequence encoding the short interfering sequence CHLI siRNA-A used according to the present technology.

SEQ ID NO: 10 is the DNA sequence encoding the short interfering sequence CHLI siRNA-B used according to the present technology.

SEQ ID NO: 11 is the DNA sequence encoding the short interfering sequence 18S siRNA-A used according to the present technology.

SEQ ID NO: 12 is the DNA sequence encoding the short interfering sequence 18S siRNA-B used according to the present technology.

SEQ ID No. 13: Synthetic construct targeting CHLI1 in *A. thaliana, B. rapa, M. truncatula, Z mays*, and *N. Tobacum.*

SEQ ID No. 14: Synthetic construct targeting mGFP5er, Acd11, Acd2, Cat1, Cat2, and Lsd1 in *B. rapa pekinensis.*

SEQ ID No. 15: Synthetic construct targeting Atg5, Cat1, Jazh, MC2, and Beclin1 in *Nicotiana sylvestris.*

SEQ ID No. 16: Synthetic construct targeting Acd2, BI-1, Lls1, NbTCTP, and Beclin1 in *Nicotiana sylvestris.*

SEQ ID No. 17: Synthetic construct consisting of CaMV35s promoter, TRV Ppk20 RNA1, ribozyme sequence and NOS terminator.

SEQ ID No. 18: TRV RNA2-MCS for transcription in plant cells.

SEQ ID No. 19: Truncated T7 driven Tobacco Rattle Virus RNA1 (T7-RNA1 inducer).

SEQ ID No. 20: Synthetic sequence consisting of optimized TRV coat protein driven by T7 promoter and a strong Ribosome binding site (RBS), and Tobacco rattle virus (TRV) isolate Ppk20 RNA1 and ribozyme sequence driven by T7 promoter. All elements are in the pUC57 vector.

SEQ ID No. 21: Synthetic T7-RNA2-MCS inducer sequence.

SEQ ID No. 22: Synthetic T7 driven RNA2 with sample construct (C3) in MCS, ribozyme, NOS.

SEQ ID No. 23: Synthetic T7-RNA2-sgP-C3 sequence.

SEQ ID No. 24: Synthetic sequence consisting of pUC57 MCS flanked by Pea Early Browning virus (PEBV) subgenomic promoters, all of which are flanked by T7 promoters.

SEQ ID No. 25: Synthetic RNA1 of TRV Ppk20 sequence.

SEQ ID No. 26: Synthetic RNA2 of pTRV2 with C3 insert sequence.

SEQ ID NO 27: Synthetic sequence consisting of SEQ ID NO 15 flanked by PEBV subgenomic promoters SEQ ID NO 28: Synthetic pRNAi-GG sequence.

SEQ ID No. 29: Synthetic pRNAi-GG with SEQID 14 inserts.

SEQ ID No. 30: Human cytomegalovirus immediate early enhancer and promoter sequence.

SEQ ID No. 31: Synthetic TRV coat protein CDS DNA from pTRV2 sequence.

SEQ ID No. 32: Synthetic Tobacco Rattle Virus Codon-optimized Coat Protein mRNA sequence.

SEQ ID No. 33: Tomato Bushy Stunt Virus P19 suppressor protein CDS from Tomato Bushy Stunt Virus M21958.1 sequence. SEQ ID No. 34: *Papaya* Ringspot Virus strain P isolate pFT3-NP HCpro peptide CDS sequence.

SEQ ID NO 35: Tobacco Mosaic Virus TMV 30 kDa movement protein CDS sequence.

SEQ ID No. 36: *Arabidopsis thaliana* TOR gene CDS (TAIR accession AT1G50030).

SEQ ID No. 37: *Arabidopsis thaliana* ATG5 sequence.

SEQ ID NO 38: *Arabidopsis thaliana* Beclin 1 sequence.

SEQ ID No. 39: *Nicotiana attenuata* ZIM domain protein h mRNA sequence.

SEQ ID NO. 40: *Nicotiana benthamiana* Bax inhibitor 1 mRNA sequence.

SEQ ID No. 41: *Nicotiana sylvestris* Acd2 partial transcript sequence derived from *N. sylvestris* transcriptome.

SEQ ID No. 42: *Lycopersicon esculentum* lethal leaf spot 1-like protein mRNA sequence.

SEQ ID NO 43: *Nicotiana* tobacum mRNA for catalase 1 (cat1 gene), cultivar NC89 sequence.

SEQ ID NO 44: *Arabidopsis thaliana* MC2 sequence.

SEQ ID No. 45: *Nicotiana benthamiana* NbTCTP mRNA for translationally controlled tumor protein sequence.

SEQ ID No. 46: *Arabidopsis thaliana* Lsd1 sequence.

SEQ ID No. 47: *Arabidopsis thaliana* Acd11 sequence.

SEQ ID No. 48: *Nicotiana sylvestris* PDS gene target construct.

SEQ ID No. 49: T7 driven RNA2 with NSYL PDS target construct in MCS.

SEQ ID No. 50: T7 driven truncated PPK20 RNA1 consisting of 5' sequence, replicase CDS, PUC57 MCS, 3' sequence, ribozyme and NOS terminator.

SEQ ID No. 51: TRV PPK20 RNAI replicase CDS.

SEQ ID No. 52: TRV PPK20 RNA2 5' replication element containing sequence

SEQ ID No. 53: TRV Ppk20 RNA2 3' replication element containing sequence

SEQ ID No. 54: *Arabidopsis thaliana* ESR gene CDS.

SEQ ID No. 55: *Arabidopsis thaliana* SAG12 (senescence associated gene 12) CDS.

SEQ ID No. 56: *Arabidopsis thaliana* PAD4 (phytoalexin deficient 4) gene CDS.

SEQ ID No. 57: *Arabidopsis thaliana* CPR5 (constitutive expression of PR genes 5) gene CDS.

SEQ ID No. 58: *Arabidopsis thaliana* ACD1 (accelerated cell death 1) gene CDS.

SEQ ID No. 59: *Arabidopsis thaliana* ATG18 (homolog of yeast autophagy gene 18 G) gene CDS.

Additional sequences included in this application are from *Arabidopsis*. Each line provides the gene symbol, genes name and *Arabidopsis* accession number.

Starvation:

SEQ ID No. 60: HDH (HISTIDINOL DEHYDROGENASE) AT5G63890

SEQ ID No. 61: ATHMEE2 (MATERNAL EFFECT EMBRYO ARREST 2/=SHI KIMATE DEHYDROGENASE) AT3G06350

SEQ ID No. 62: ICDH (ISOCITRATE DEHYDROGENASE) AT1G54340

Early Senescence:

SEQ ID No. 63: APG 9 (AUTOPHAGY 9) AT2G31260

SEQ ID No. 64: ATG 2 (AUTOPHAGY 2) AT3G19190

SEQ ID No. 65: SRI (SIGNAL RESPONSIVE 1) AT2G22300

SEQ ID No. 66: APG7 (AUTOPHAGY 7) AT5G45900

Definitions

RNAi Payload means a payload consisting of at least one specific nucleic acid sequence or analogue sequence that, when introduced into the body of a plant, will trigger or initiate an RNAi cascade.

Cell (or host plant cell) means a cell or protoplast of a plant cell and includes isolated cells and cells in a whole plant, plant organ, or fragment of a plant. It also includes non-isolated cells.

Double stranded region means a region of a polynucleotide wherein the nucleotides or analogues are capable of hydrogen bonding to each other. Such hydrogen bonding can be intramolecular or intermolecular (e.g. single transcription unit forming a double stranded region with the so-called hairpin or two transcription units that align appropriately for complementary sequences to hydrogen bond). To be a double stranded region, according to the present invention, it is not necessary for 100% of the nucleotides to be complementary and hydrogen bonded within a region. It is merely necessary for sufficient base pairing to occur to give the RNA a substantial double stranded character (e.g. an indicative melting point).

RNAi Inducer means at least one specific nucleic acid sequence or analogue sequence that, when introduced into the body of a plant, will trigger or initiate an RNAi cascade. This can be, for example, but is not limited to DNA, dsRNA, ssRNA, siRNA, and miRNA sequences. RNAi inducers are usually capable of activating RNAi in a number of species.

Targeting constructs are added to the RNAi inducer sequence to direct the RNAi response against specific endogenous polynucleotides.

Targeting construct means a region of nucleic acid sequence that is complementary to one or more endogenous or exogenous polynucleotides. siRNAs released from the processing of a targeting construct direct RNAi machinery to knock-down endogenous polynucleotides.

RdRP means a RNA-dependent RNA polymerase. An RdRP creates a complementary strand of RNA using RNA as a template. Endogenous RdRPs include components of RISC machinery, and DNA-dependent RNA polymerases when recruited by special RNA sequences/structures. Exogenous RdRPs come from virus, retrotransposons, or are harvested from another organism.

Exogenous gene means a gene that is not normally present in a given host genome in the present form. In this respect, the gene itself may be native to the host genome, however the exogenous gene will comprise the native gene altered by the addition or deletion of one or more different regulatory elements or additional genes.

Gene or genes means nucleic acid sequences (including both RNA or DNA) that encode genetic information for the synthesis of a whole RNA, a whole protein, or any functional portion of such whole RNA or whole protein sufficient to possess a desired characteristic.

Marker gene means a gene that, when its activity is altered, imparts a distinct phenotype.

Essential gene means a gene that, when inhibited, results in a negative effect on at least one of plant growth and development. They are required for normal plant growth and reproduction.

Heterologous polynucleotide means any polynucleotide that is introduced (transiently or stably) into a non-transformed host plant. A polynucleotide is not excluded from being a heterologous polynucleotide by the presence of matching endogenous polynucleotide sequences.

Homologous means having sequence similarity sufficient to allow hybridization in vivo, in vitro, and/or ex vivo under low stringency conditions between the antisense sequence and the sense gene mRNA.

Inhibition of gene expression means a decrease in the level of protein and/or RNA product from a target gene. The consequences of inhibition can be confirmed by examination of the outward properties of the cell or organism (as presented below in the examples) or by biochemical techniques such as RNA solution hybridization, nuclease protection, Northern hybridization, polymerase chain reaction (PCR), reverse transcription (RT) reverse transcription PCR(RT/PCR), gene expression monitoring with a microarray, antibody binding, enzyme linked immunosorbent assay (ELISA), Western blotting, radioimmunoassay (RIA), other immunoassays, and fluorescence assisted cell sorting (FACS).

Substantially complementary, with respect to the sense and antisense sequences means sufficiently complementary to allow for formation of a double stranded molecule.

Transcript means RNA encoded by DNA. In the context of sense and antisense transcripts of the present invention, such sense and antisense transcripts can be part of the same polynucleotide or they can be 2 separate polynucleotides (i.e., each having its own 5' and 3' end).

Treating a weed plant means a method to cause a deleterious effect on the weed, for example, but not limited to, interfering with development, reducing growth, triggering programmed cell death such as apoptosis, senescence, or autophagy, reducing vigour, interfering with reproductive viability, or result in death.

hpRNA is hairpin RNA, produced through inverted repeats with or without a single stranded loop region.

RISC is an RNA-induced silencing complex.

dsRNA is double stranded RNA. siRNA is short interfering RNA.

miRNA is microRNA and is a small non-coding RNA molecule (ca. 22 nucleotides) found in plants and animals. They function in transcriptional and post-transcriptional regulation of gene expression.

pTRV1 and pTRV2 are well proven RNAi inducers. One skilled in the art can use other virus based sequences to create an inducer by placing the virus sequence between a suitable promoter and terminator and incorporating an MCS into it.

Weeds mean members of the Amaranthaceae family, such as green pigweed and redroot pigweed, members of the Anacardiaceae family, such as western poison-oak, central poison-ivy, eastern poison-ivy, rydberg's poison-ivy, and poison sumac, members of the Asclepiadaceae family, such as common milkweed, black dog-strangling vine, and dog-strangling vine, members of the Balsaminaceae family such as spotted jewelweed, members of the Berberidaceae family such as common barberry, members of the Boraginaceae family such as blueweed, and stickseed, members of the Caryophyllaceae family such as purple cockle, mouse-eared chickweed, bouncingbet, night-flowering catchfly, white cockle, bladder campion, corn spurry, chickweed, grass-leaved stichwort, and cow cockle, members of the Chenopodiaceae family such as Russian pigweed, lamb's quarters, *Kochia*, and Russian thistle, members of the Compositae family (Asteraceae) such as common yarrow, Russian knapweed, common ragweed, perennial ragweed, giant ragweed, stinking mayweed, common burdock, woolly burdock, absinth, biennial wormwood, mugwort, New England aster, nodding beggarticks, tall beggarticks, plumeless thistle, nodding thistle, diffuse knapweed, brown knapweed, spotted knapweed, black knapweed, chicory, Canada thistle, bull thistle, Canada fleabane; smooth hawk's-beard, narrow-leaved hawks-beard, Philadelphia fleabane, rough fleabane, spotted Joe-Pye weed, hairy *galinsoga*, orange hawkweed, mouse-eared hawkweed, king devil hawkweed, spotted cat's-ear, elecampane, poverty weed, false ragweed, prickly lettuce, blue lettuce, nipplewort, fall hawkbit, ox-eye daisy, pineapple weed, scentless chamomile, black-eyed Susan, tansy ragwort, Canada goldenrod, perennial sow-thistle, spiny annual sow-thistle, annual sow-thistle, tansy, dandelion, goat's-beard, meadow goat's-beard, colt's-foot, and cocklebur, members of the Convolvulaceae family such as field bindweed, and field dodder, members of the Crassulaceae family such as mossy stonecrop, members of the Cruciferae family (Brassicaceae) such as garlic mustard, yellow rocket, hoary *alyssum*, Indian mustard, bird rape, small-seeded false flax, shepherd's purse, lens-podded hoary cress, hare's-ear mustard, flixweed, wood whitlow-grass, dog mustard, wormseed mustard, tall wormseed mustard, dame's-rocket, field pepper-grass, common pepper-grass, poor-man's pepper-grass, ball mustard, wild radish, creeping yellow cress, wild mustard, tumble mustard, tall hedge mustard, and stinkweed, members of the Cucurbitaceae family such as wild cucumber, members of the Cyperaceae family such as yellow nut sedge, members of the Equisetaceae family such as field horsetail, members of the Euphorbiaceae family such as three-seeded mercury, cypress spurge, leafy spurge, and hairy-stemmed spurge, members of Gramineae family (Poaceae) such as wild oats, smooth brome, downy brome, smooth crab grass, large crab grass, barnyard grass, quack grass, foxtail barley, Persian darnel, witch grass, common reed, annual blue grass, Kentucky blue grass, green foxtail, and yellow foxtail, members of the Guttiferae family such as St. John's-wort, member of the Haloragaceae family such as Eurasian water-milfoil, members of the Hydrocharitaceae family such as European frogbit, members of the Labiatae family such as *ajuga*, American dragonhead, hemp-nettle, ground-ivy, motherwort, catnip, heal-all, andmarsh hedge-nettle, members of the Leguminosae family (Fabaceae) such as hog-peanut, bird's-foot trefoil, black medick, white sweet-clover, yellow sweet-clover, crown vetch, white clover, and tufted vetch, members of the Liliaceae family such as false hellebore, showy false hellebore, smooth camas, and meadow camas, members of the Lythraceae family such as purple loosestrife, members of the Malvaceae family such as velvetleaf, round-leaved mallow, and common mallow, members of the Onagraceae family such as fireweed, and yellow evening-primrose, members of the Oxalidaceae family such as European wood-sorrel, members of the Plantaginaceae family including narrow-leaved plantain, broad-leaved plantain, hoary plantain, and Rugel's plantain, members of the Polygonaceae family such as Tartary buckwheat, striate knotweed, prostrate knotweed, wild buckwheat, pale smartweed, lady's-thumb, green smartweed, sheep sorrel, curled dock, long-leaved dock, field dock, serrate-valved dock, and broad-leaved dock, members of the Pteridaceae family such as bracken, members of the Portulacaceae family such as purslane, members of the Ranunculaceae family such as tall buttercup, and creeping buttercup, members of the Rhamnaceae family such as European buckthorn, members of the Rosaceae such as silvery cinquefoil, rough cinquefoil, sulfur cinquefoil, narrow-leaved meadowsweet, and hardhack, members of the Rubiaceae family such as smooth bedstraw, members of the Scrophulariaceae family such as dwarf snapdragon, yellow toadflax, Dalmation toadflax, moth mullein, common mullein, and thyme-leaved speedwell, members of the Solanaceae family such as climbing nightshade, and eastern black nightshade, members of the Typhaceae family such as narrow-leaved cattail, and cattail, members of the Umbelliferae (Apiaceae) family such as goutweed, caraway, western water-hemlock, spotted water-hemlock, poison-hemlock, wild carrot, giant hogweed, wild parsnip, and water-parsnip, and members of the Urticaceae family such as stinging nettle.

In addition, the following weeds will be controlled, if not already listed above:

*Abutilon theophrasti* (Velvetleaf), *Acroptilon repens* (Russian Knapweed), *Aegilops cylindrica* (Jointed Goatgrass), *Agropyron repens* (Quackgrass), *Alyssum*, Hoary (Berteroa *incana*), *Amaranthus retroflexus* (Redroot Pigweed), *Anchusa officinalis* (Common Bugloss), Annual Bluegrass (*Poa annua*), Annual Sow-thistle (*Sonchus oleraceus*), Annual Sow-thistle, Spiny (*Sonchus asper*), *Anthriscus sylvestris* (Wild Chervil), *Arctium* spp. (Burdock), *Asclepias speciosa* (Showy Milkweed), *Avena fatua* (Wild Oats), Baby's-Breath (*Gypsophila paniculata*), Barley, Foxtail (*Hordeum jubatum*), Barnyardgrass (*Echinochloa crusgalli*), Beggar-Ticks, Nodding (*Bidens cernua*), Berteroa *incana* (Hoary *Alyssum*), *Bidens cernua* (Nodding Beggar-Ticks), Bindweed, Field (*Convolvulus arvensis*), Bladder Campion (*Silene cucubalus*), Bluegrass, Annual (*Poa annua*), Blueweed (*Echium vulgare*), Bog Rush (*Juncus effusus*), Broad-Leaved Plantain (*Plantago major*), Buckwheat, Tartary (*Fagopyrum tataricum*), Buckwheat, Wild (*Polygonum convolvulus*), Bugloss, Common (*Anchusa officinalis*), Bull Thistle (*Cirsium vulgare*), Burdock (*Arctium* spp.), Buttercup, Creeping (*Ranunculus repens*), Canada Thistle (*Cirsium arvense*), *Capsella bursa-pastoris* (Shepherd's-Purse), *Cardaria* spp. (Hoary Cress), *Carduus nutans* (Nodding Thistle, a.k.a. Musk Thistle), *Carduus acanthoides* (Plumeless Thistle), *Centaurea diffusa* (Diffuse Knapweed), *Centaurea pratensis* (Meadow Knapweed), *Centaurea solstitialis* (Yellow Starthistle), *Centaurea maculosa* (Spotted Knapweed), Chamomile, Scentless (*Matricaria maritima*), *Chenopodium album* (Lamb's-Quarters), *Cichorium intybus* (Chicory), *Cirsium palustre* (Marsh Plume Thistle), Chervil, Wild (*Anthriscus sylvestris*), Chicory (*Cichorium intybus*), *Chondrilla juncea* (Rush Skeletonweed), *Chrysanthemum leucanthemum* (Oxeye Daisy), *Cicuta douglasii* (Water Hemlock), Cinquefoil, Sulphur (*Potentilla recta*), *Cirsium arvense* (Canada Thistle), *Cirsium vulgare* (Bull Thistle), Cleavers (*Galium aparine*), Cluster Tarweed (*Madia glomerata*), Common Bugloss (*Anchusa officinalis*), Common Tansy (*Tanacetum vulgare*), Common Mallow (*Malva neglecta*), Common Chickweed (*Stellaria media*), *Convolvulus arvensis* (Field Bindweed), Corn Spurry (*Spergula arvensis*), Creeping Buttercup (*Ranunculus repens*), *Crupina vulgaris* (*Crupina*), Cudweed (*Gnaphalium uliginosum*), Curled Dock (*Rumex crispus*), *Cytisus scoparius* (Scotch Broom), Dalmatian Toadflax (*Linaria dalmatica*), Diffuse Knapweed (*Centaurea diffusa*), Dodder, (*Cuscuta* spp.), Field Bindweed (*Convolvulus arvensis*), Field Scabious (*Knautia arvensis*), Foxtail Barley (*Hordeum jubatum*), Giant Hogweed (*Heracleum mantegazzianum*), Gorse (*Tragopogon dubius*), Green Foxtail (*Setaria viridis*), Groundsel (*Senecio vulgaris*), *Gypsophila paniculata* (Baby's-Breath), Hemp-Nettle (*Galeopsis tetrahit*), Henbit (*Lamium amplexicaule*), *Heracleum mantegazzianum* (Giant Hogweed), Himalayan Balsam (*Impatiens glandulifera*), Hoary *Alyssum* (Berteroa *incana*), Hoary Cress (*Cardaria* spp.), *Hordeum jubatum* (Foxtail Barley), Horsetail, Field (*Equisetum arvense*), Hound's-tongue (*Cynoglossum officinale*), *Hypericum perforatum* (St. John's-Wort), *Impatiens glandulifera* (Himalayan Balsam), Japanese Knotweed (*Polygonum cuspidatum*), Jointed Goatgrass (*Aegilops cylindrica*), *Juncus effusus* (Bog Rush), Knapweed, Meadow (*Centaurea pratensis*), Knapweed, Spotted (*Centaurea maculosa*), Knapweed, Russian (*Acroptilon repens*), Knapweed, Diffuse (*Centaurea diffusa*), *Knautia arvensis* (Field Scabious), *Kochia scoparia* (*Kochia*), Lady's-Thumb (*Polygonum persicaria*), Lamb's-Quarters (*Chenopodium album*), *Lamium amplexicaule* (Henbit), Leafy Spurge (*Euphorbia esula*), *Lepidium latifolium* (Perennial Pepperweed), *Linaria dalmatica* (Dalmatian Toadflax), *Linaria vulgaris* (Yellow Toadflax), *Lychnis alba* (White Cockle), *Lythrum salicaria* (Purple Loosestrife), *Madia glomerata* (Cluster Tarweed) *Malva neglecta* (Common Mallow), Marsh Plume Thistle (*Cirsium palustre*), *Matricaria maritima* (Scentless Chamomile), *Matricaria matricariodes* (Pineappleweed), Meadow Knapweed (*Centaurea pratensis*), Meadow Hawkweed (*Hieracium pilosella*), Milkweed, Showy (*Asclepias speciosa*), Mullein (*Verbascum thapsus*), Mustard, Wild (*Sinapsis arvensis*), Narrow-Leaved Plantain (*Plantago lanceolata*), Night-Flowering Catchfly (*Silene noctiflora*), Nightshade (*Solanum* spp.), Nodding Thistle, a.k.a. Musk Thistle (*Carduus nutans*), Nodding Beggar-Ticks (*Bidens cernua*), Nutsedge, Purple (*Cyperus rotundus*), Nutsedge, Yellow (*Cyperus esculentus*), *Onopordum acanthium* (Scotch Thistle), Orange Hawkweed (*Hieracium aurantiacum*), Oxeye Daisy (*Chrysanthemum leucanthemum*), *Panicum capillare* (Witchgrass), Perennial Pepperweed (*Lepidium latifolium*), Perennial Sowthistle (*Sonchus arvensis*), Pigweed, Redroot (*Amaranthus retroflexus*), Pineappleweed (*Matricaria matricariodes*), *Plantago lanceolata* (Narrow-Leaved Plantain), *Plantago major* (Broad-Leaved Plantain), Plumeless Thistle (*Carduus acanthoides*), *Poa annua* (Annual Bluegrass), *Polygonum convolvulus* (Wild Buckwheat), *Polygonum cuspidatum* (Japanese Knotweed), *Polygonum persicaria* (Lady's-Thumb), *Potentilla recta* (Sulphur Cinquefoil), Puncture vine (*Tribulus terrestris*), Purple Nutsedge (*Cyperus rotundus*), Purple Loosestrife (*Lythrum salicaria*), Quackgrass (*Agropyron repens*), *Ranunculus repens* (Creeping Buttercup), *Rumex acetosella* (Sheep Sorrel), *Rumex crispus* (Curled Dock), Rush Skeletonweed (*Chondrilla juncea*), Russian Knapweed (*Acroptilon repens*), Russian Thistle (*Salsola kali*), Scentless Chamomile (*Matricaria maritima*), Scotch Broom (*Cytisus scoparius*), Scotch Thistle (*Onopordum acanthium*), *Senecio jacobaea* (Tansy Ragwort), Sheep Sorrel (*Rumex acetosella*), Shepherd's-Purse (*Capsella* bursa-*pastoris*), Sulphur Cinquefoil (*Potentilla recta*), Spotted Knapweed (*Centaurea maculosa*), St. John's-Wort (*Hypericum* perforatum), Stinkweed (*Thlapsi arvense*), Tansy Ragwort (*Senecio jacobaea*), Tartary Buckwheat (*Fagopyrum tataricum*), Tarweed, Cluster (*Madia glomerata*), Thistle, Bull (*Cirsium vulgare*), Thistle, Canada (*Cirsium arvense*), Nodding Thistle a.k.a. Musk Thistle (*Carduus nutans*), Plumeless Thistle (*Carduus acanthoides*), Russian Thistle (*Salsola kali*), Scotch Thistle (*Onopordum acanthium*), *Thlapsi arvense* (Stinkweed), Dalmatian Toadflax (*Linaria dalmatica*), Yellow Toadflax (*Linaria vulgaris*), *Tragopogon dubius* (Western Goat's-Beard), *Tribulus terrestris* (Puncture vine), *Ulex europaeus* (Gorse), Velvetleaf (*Abutilon theophrasti*), *Verbascum thapsus* (Mullein), Water Hemlock (*Cicuta douglasii*), Western Goat's-Beard (*Tragopogon dubius*), White Cockle (*Lychnis alba*), Wild Chervil (*Anthriscus sylvestris*), Wild Mustard (*Sinapsis arvensis*), Wild Buckwheat (*Polygonum convolvulus*), Wild Oats (*Avena fatua*), Witchgrass (*Panicum capillare*), Yellow Hawkweed (*Hieracium pratense*), Yellow Starthistle (*Centaurea solstitialis*), Kudzu (*Pueraria lobata*), Japanese dodder (*Cuscuta japonica*), water hyacinth (*Eichhornia* spp.) and Yellow Nutsedge (*Cyperus esculentus*).

Underlying the various embodiments of the present invention is treating a weed by introducing a heterologous polynucleotide or analogue into the weed plant, the heterologous polynucleotide comprising: 1) an RNAi inducer capable of recruiting RISC machinery to the sequence and 2) a targeting construct comprising (a) an antisense sequence having homology to an essential gene, or a marker gene, or (b) a sense sequence substantially complementary to said antisense sequence; wherein said sense and antisense sequences are capable of hybridizing to each other to form a double-stranded region.

DESCRIPTION

Except as otherwise expressly provided, the following rules of interpretation apply to this specification (written description, claims and drawings): (a) all words used herein shall be construed to be of such gender or number (singular or plural) as the circumstances require; (b) the singular terms “a”, “an”, and “the”, as used in the specification and the appended claims include plural references unless the context clearly dictates otherwise; (c) the antecedent term “about” applied to a recited range or value denotes an approximation within the deviation in the range or value known or expected in the art from the measurements method; (d) the words “herein”, “hereby”, “hereof”, “hereto”, “hereinbefore”, and “hereinafter”, and words of similar import, refer to this specification in its entirety and not to any particular paragraph, claim or other subdivision, unless otherwise specified; (e) descriptive headings are for convenience only and shall not control or affect the meaning or construction of any part of the specification; and (f) “or” and “any” are not exclusive and “include” and “including” are not limiting. Further, The terms “comprising,” “having,” “including,” and “containing” are to be construed as open-ended terms (i.e., meaning “including, but not limited to,”) unless otherwise noted. To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Overview:

An RNAi payload is introduced into a host plant, for example, a weed by application of a formulation comprising the payload. Application methods include spraying, irrigating, injecting (extracellular as opposed to microinjection), abrading or otherwise causing entry of the formulation into, for example, but not limited to, a seed, a seedling, a sapling, a mature plant, a reproducing plant or a senescing plant. Application methods do not include stable transformation methods. The RNAi payload comprises one or more RNAi inducer elements encouraging its processing by dicer. The RNAi payload also contains a targeting region complementary to corresponding essential genes, or marker genes or both. When the RNAi payload is processed it releases siRNAs against those genes. The siRNAs direct RISC machinery to knock down those genes.

A list of genes used to build targeting constructs is provided. For each gene, one or more of double stranded RNA fragments and the DNA coding sequences or analogues that generate them are provided. These fragments have sequences that allow them to initiate the RNAi cascade, hence the DNA sequences will have, in addition, suitable promoters, for example, but not limited to, constitutive promoters that result in a high level of expression, and a suitable transcriptional stop element. The DNA sequences may be provided as crude viral or bacterial extracts, plasmid or viral DNA with the sequence and regulatory regions inserted therein, or may be synthesized. Each target in the targeting construct comprises at least about 19 nucleotides or at least about 50 nucleotides, or at least about 100 nucleotides, or at least about 150 nucleotides, and all sub ranges therebetween. During the knock-down process RdRPs ‘transcribe’ the target mRNAs. These transcripts are processed into more siRNAs targeting the whole mRNA. These are transported through the plant where they spread the cascade.

In the context of the present invention, there are three important steps to an effective RNAi herbicide. Firstly, the RNAi payload (DNA, RNA, or synthetic oligos) is delivered to the plant or part of the plant. Application methods affect delivery, with stem injection, spray, and vector-aided delivery (without stable transformation) being common techniques. Once applied, the inducer is introduced to the cytoplasm of the target cells. This may be mediated by, for example, but not limited to, additives, chemical modification of the inducer, or vectors such as viral coat protein, or nano-cages.

Secondly, a build-up of RNA occurs that can spread from cell to cell. This can happen prior to the RNAi response if exogenous RNA polymerases (such as viral RdRPs) are included as RNAi inducer elements, or if endogenous RNA polymerases (including DNA dependant RNA polymerases) are recruited to replicate the payload. It can also happen during the RNAi response if the inducer triggers RNAi-associated RdRPs. The entire inducer can be replicated, or only specific regions (using internal RNA promoters such as viral subgenomic promoters). Inducers can use one or both of these pathways for replication. Viral RNAi suppressor proteins can be included to increase the amount of RNA present before RNAi is triggered. Cell-to-cell spread can be accelerated using viral movement proteins and by targeting key plant genes.

Finally, the RNAi inducer elements elicit an RNAi response that targets RISC machinery to degrade critical endogenous RNAs. This is accomplished by complementarity between regions of the inducer and the target RNAs. Once the inducer is processed into siRNAs they are used by RISC to target further RNA. siRNAs produced from the targeting construct are complementary to endogenous target genes. These are knocked down as “Collateral damage” while the plant clears the payload.

In addition to the sequences for essential genes, the payload will include RNA fragments that will silence genes that modulate the RNAi cascade. These will be synthetic or virally derived RNA fragments targeting components of the RNAi pathway. Without being bound by theory, it is believed that the RNA payload used in the present technology will target and silence, knock-down, or dysregulate genes that are necessary for the proper growth and development and optimally, the survival of the weed.

Elements

Target genes: Apoptosis; Autophagy; Senescence; Starvation; Accessory (RISC components)

RNAi inducers: Replicase/promoter pairs; (Viral replicase and promoter/subgenomic promoter pairs; Recruitment and co-option of endogenous RNA polymerases; and Action of endogenous rdRPs [siRNA asymmetries, single base mismatches]); Recruitment of DNA ligases for RNA ligation; and that recruit dicer for RNAi processing (dsRNA regions [Inverted repeats; Hairpins; and Direct repeats])

Functional elements: Promoters; Terminators; Ribosome binding sites; Internal ribosome entry sites; Hammerhead ribozymes; Recruitment and co-option of endogenous DNA ligase to ligate RNA; and Cap stealing or RNA capping sequences.

Exogenous helper genes: Coat proteins; Movement Proteins; and RNAi suppressor proteins.

Without being bound to theory, there are three primary ways to kill plants using an RNAi cascade. The first way knocks down production of essential cellular components. This causes cells to starve, or to structurally degrade. Target genes include EPSP synthese, chalcone synthase, starch synthase, cellulose synthase, acetyl-COA reductase, transaminase, 18S rRNA, eEF-IB gamma, SAP130b, TRPT, PAI1, PDS, DGL The second way is to induce apoptotic programmed cell death by knocking out key repressors in the pathway. This results in Hypersensitive response like (HR) and necrotic lesions. It is quicker than starvation but may in some situations be too quick, killing cells before the RNAi cascade can spread. Runaway hypersensitive response can also be elicited in this manner Target genes include BECLIN1 PI3K/VPS30 ATG3 ATG7 CAT1 ACD2, NbTCTP, LLS1.

The final way is by inducing senescence, again by knocking out key repressors of that pathway. Once senescence is triggered cells undergo a slower, more regulated cell death. Target genes to induce senescence include: APG 9 (Autophagy 9), ATG 2 (Autophagy 2), SRI (Signal responsive 1, APG7 (Autophagy 7)

Autophagy can be triggered along with any of these responses. During autophagy plant cells engulf and digest their organelles.

Helper genes include the following:

Protein coding sequences for:

a. Viral movement proteins that interact with coat protein (VIGS based inducer)

b. Viral movement proteins that do not require coat protein c. Viral coat proteins Production of RNA is achieved through transcription of a DNA template, either in a cell such as *E. coli* or in vitro. DNA is produced in cells, or through PCR. Promoter-polymerase combinations such at the T7 system can be used for tight control of transcription and high yield. Eukaryotic expression systems such as yeast are also viable production factories. Viral coat proteins or other protective structures may be produced in the same cells or added later to purified RNA.

The simplest RNAi inducers are siRNAs. They are recognised by RISC machinery and used directly to guide knockdown of endogenous polynucleotides. If properly formatted they also encourage endogenous RdRPs to amplify the silencing signal and cause transitivity. The siRNA sequence is also the simplest targeting construct. Longer targeting constructs can be grouped together on an RNA. Using secondary structure such as hairpins, or by transcribing both DNA strands into RNA, large dsRNA regions are created. These are recognised and processed by RISC machinery. The dsRNA replication intermediate of many virus is a trigger for RNAi, allowing many virus to act as RNAi inducers. Incorporating a targeting construct into such a virus results in a functional RNAi herbicide. Finally, single stranded RNA or DNA transcribed in plant cells can trigger RNAi if the RNA is replicated. This is achieved by including coding sequences for exogenous RdRPs, or through RNA sequences that recruit endogenous RdRPs.

Examples of the RNAi payloads used in the present technology follow and were designed to target the sequences as shown:

```
                                        SEQ ID NO: 1
Actin 2 siRNA-A (target sequence:
5'-GGCATCACACTTTCTACAA-3');

                                        SEQ ID NO: 2
Actin 2 siRNA-B (target sequence:
5'-CGAGAAGAACTATGAATTA-3');

                                        SEQ ID NO: 3
CHLI siRNA-A (target sequence:
5'-GGAGATAGAGGAACTGGAA-3');

                                        SEQ ID NO: 4
CHLI siRNA-B (target sequence:
5'-GGAACATCTTCTTCTGCAA-3');

                                        SEQ ID NO: 5
18S siRNA-A (target sequence:
5'-GGGAGGTAGTGACAATAAA-3');
and

                                        SEQ ID NO: 6
18S siRNA-B (target sequence:
5'-GGACGCATTTATTAGATAA-3').
```

The RNAi payloads used in die present technology were designed to target the sequences as shown:

```
                                                SEQ ID NO: 7
Actin 2 siRNA-A
(target sequence: 5'-GGCATCACACTTTCTACAA-3');

                                                SEQ ID NO: 8
Actin 2 siRNA-B
(target sequence: 5'-CGAGAAGAACTATGAATTA-3');

                                                SEQ ID NO: 9
CHLI siRNA-A
(target sequence: 5'-GGAGATAGAGGAACTGGAA-3');

                                               SEQ ID NO: 10
CHLI siRNA-B
(target sequence: 5'-GGAACATCTTCTTCTGCAA-3');

                                               SEQ ID NO: 11
18S siRNA-A
(target sequence: 5'-GGGAGGTAGTGACAATAAA-3');
and

                                               SEQ ID NO: 12
18S siRNA-B
(target sequence: 5'-GGACGCATTTATTAGATAA-3').
```

Design: For the target genes, siRNAs were designed with reference to the literature, the target site accessibility web tool, RNAxs and BLAST searches.

The genes chosen were essential genes or marker genes, which, when knocked down would be expected to provide an easily identifiable phenotype.

The first siRNAs were designed to be incorporated into Argonaute protein (AGO1). They were 21 nt in length with a UU, 3' overhang on each end and a 5' terminal U. A 5' phosphate was added to the guide strand of the siRNA.

Other designs include one or more of targeting different AGO complexes, using a different 5' nucleotide, using chemically modified siRNA to increase stability, using different 3' overhang nucleotides, and including a 5' phosphate on both strands.

As the mRNA target site should be accessible, the RNAxs webserver was used to search through a given mRNA sequence and identify those sites based on the 2° structure of the mRNA and thermodynamic asymmetry and folding energies associated with the siRNAs themselves.

siRNA means “small interfering RNA” which are also commonly referred to as “short interfering RNA” or alternatively as “silencing RNA”.

Details of the process used to produce targeting constructs in *Nicotiana sylvestris* were as follows (this process applies to designing targeting constructs for any plant): Target gene mRNAs were run through the RNAxs program using standard settings.

The top 20-25 hits (lowest "worst rank") were mapped to the original mRNA sequence When available, homologous mRNA sequences from other *N. sylvestris* (or *Solanacea* spp. or *Arabidopsis thaliana*) were also run through RNAxs and have their highest 20-25 hits mapped.

The homologues were then aligned to compare the regions of highest effective siRNA target concentration.

For the present technology, regions with numerous "good" targets that also have perfect (or at most 2 mismatches in a stretch of 21 nt) sequence identity to the *N. sylvestris* sequence were sought.

*N. sylvestris* was used as the reference sequence for all targets, therefore the whole construct had perfect sequence identity to *N. sylvestris.*

Regions of effective targets were cut from the original mRNA sequence to make smaller target regions of various lengths (21-120 nt). The 18-24 nt regions can be used directly as siRNA constructs (which have both RNAi inducer and targeting construct activity). Otherwise, the process to build longer, multi-gene targeting constructs is as follows:

Sequences complementary to the most accessible mRNA regions were pulled out were trimmed to remove intervening sequences where no effective siRNAs are predicted.

Multiple trimmed segments were joined together to make an approx. 120 nt targeting cluster that consist of 10s of predicted high-effectiveness siRNAs targeting a gene of interest.

Other considerations included that the target sites should not cover splice junctions or start or stop codons and should avoid sites of single nucleotide polymorphisms between sequenced transcript variants.

Longer RNAi payloads require RNAi inducer elements to induce the processing of the payload into siRNAs. These mostly involve the production of a dsRNA region in the RNAi payload.

Synthesis: For using siRNAs directly as RNAi payloads the selected siRNAs were synthesized chemically. A 5' phosphate was added to the guide strand of the siRNA.

Longer RNAi payloads are transcribed from DNA, either in vitro, in plantae, or in another organism such as *Escherichia coli*. The DNA sequences encoding longer RNAi payloads may also be synthesized or produced using standard cloning techniques and PCR, or a combination of both.

DNA production: The selected DNA encoding the RNAi payloads were cloned using standard cloning techniques, in, for example, but not limited to a replication system in *E. coli*, using vectors that comprise, for example, but are not limited to, pBR322, pUC series, M13 mp series, pACYC184, etc., and pCAMBIA 1201. The DNA sequence was inserted into the vector at a suitable restriction site. The resulting plasmid was used for transformation into *E. coli*. The *E. coli* cells were cultivated in a suitable nutrient medium, then harvested, lysed and optionally lyophilyze and used directly, or the plasmid was recovered and used as such, or the specific sequence and the promoter and the transcription stop were recovered and used.

There are a wide number of promoters that can be employed, including constitutive inducible, and tissue or temporally specific promoters. Plant promoters include but are not limited to ribulose-1,6-bisphosphate (RUBP) carboxylase small subunit (ssu), beta-conglycinin promoter, beta-phaseolin promoter, ADH promoter, heat-shock promoters, the enhanced CaMV 35S promoter and tissue specific promoters.

Transcription stops include but are not limited to nopaline synthase (NOS) gene transcription stop, the Cauliflower mosaic virus (CaMV) 35S gene transcription stop, and the Rubisco small subunit (SSU) gene transcription stop.

Those skilled in the art will be aware of additional promoter sequences and terminator sequences suitable for use in performing the invention. Such sequences may readily be used without any undue experimentation.

Embodiments of the present invention are taught herein where it is desirable to have more than one terminator. Examples of such are embodiments are where the sense and antisense sequences are to be contained on separate transcripts (i.e. each having its own 3' and 5' end).

Delivery:

The RNAi payloads are delivered to the weed as a formulation by spraying, irrigating, injecting, or abrading a seedling, a sapling, a mature plant, a reproducing plant or a senescing plant. Both the stem and the petiole will be injected. Leaves will be specifically targeted in addition to delivering the formulation to the entire plant. Seeds will also treated by dipping or imbibition. Roots will be treated by irrigation.

In addition to the RNAi payload, accessory targeting constructs, and helper genes, the formulations include any or all of a liquid carrier, a surfactant, a binder and tackifier, a thickener, a colourant, a spreader, an antifreezing agent, a sticker, an anticaking agent, a stabilizer, a disintegrator, an emulsifier, a synergistic compound, an abrasive, an emulsifier, a penetrating agent and a preservative.

The liquid carrier includes, for example, alcohols including monohydric alcohols such as methanol, ethanol, propanol, isopropanol, butanol and the like and polyhydric alcohols such as ethylene glycol, diethylene glycol, propylene glycol, hexylene glycol, poly(ethylene glycol), poly(propylene glycol), glycerol and the like; polyhydric alcohol-based compounds such as propylene glycol ether and the like; ketones such as acetone, methyl ethyl ketone, methyl isobutyl ketone, diisobutyl ketone, cyclohexanone and the like; ethers such as ethyl ether, dioxane, ethyleneglycol monoethyl ether, dipropyl ether, tetrahydrofuran and the like; aliphatic hydrocarbons such as normal paraffins, naphthenes, isoparaffins, kerosenes, minerals oil and the like; aromatic hydrocarbons such as benzene, toluene, xylene, solvent naphtha, alkylnaphthalenes and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as gamma-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water; and so on. These can be used singly or can be used as a combination of two kinds or more.

The penetrating agents include dimethyl sulphoxide (DMSO), Azone (1-dodecylazacycloheptan-2-one or laurocapran), N-methyl-2-pyrolidone, glycols (diethylene glycol and tetraethyleneglycol), fatty acids (lauric acid, myristic acid, oleic acid and capric acid), terpenes such as the essential oils of *eucalyptus, chenopodium* and ylang-ylang, sesquiterpenes, polyethylene glycol (PEG) and L-menthol.

The surfactant includes, for example, nonionic surfactants such as sorbitan fatty acid esters, polyoxyethylene sorbitan fatty acid esters, sucrose fatty acid esters, polyoxyethylene fatty acid esters, polyoxyethylene resinate esters, polyoxyethylene fatty acid diesters, polyoxyethylene alkyl ethers, polyoxyethylene alkylphenyl ethers, polyoxyethylene dialkyl phenyl ethers, polyoxyethylene alkyl phenyl ether-formalin condensate products, polyoxyethylene-polyoxypropylene block copolymers, alkyl polyoxyethylene-polypropylene block polymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, lignin sulfonate salts, alkylsulfosuccinate salts, naphthalenesulfonate salts, alkylnaphthalene sulfonate salts, salts of formalin condensate products of naphthalene sulfonic acid, salts of formalin condensate products of alkylnaphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylaminopropylamine acetate salts, alkylamine salts including alkyltrimethylammonium chloride and alkyldimethylbenzalkonium chloride and the like; ampholytic surfactants such as amino acid type- or betaine type-surfactants and the like; and so on. These surfactants can be used singly or can be used as a combination of two kinds or more.

The binder and tackifier include, for example, carboxymethylcellulose and a salt thereof, dextrin, water-soluble starch, xanthan gum, guar gum, sucrose, poly(vinylpyrrolidone), gum arabic, polyvinyl alcohol), polyvinyl acetate), sodium polyacrylate, poly(ethylene glycol) with an average molecular weight of 6000 to 20000, polyethylene oxide with an average molecular weight of 100000 to 5000000, phospholipid (for example, cephalin, lecithin and the like) and so on.

The thickener includes, for example, water-soluble polymers such as xanthan gum, guar gum, carboxymethylcellulose, poly(vinylpyrrolidone), carboxyvinyl polymers, acrylic polymers, starch-based compounds and polysaccharides; inorganic fine powders such as high-purity bentonite and fumed silica (white carbon); and the like.

The colourant includes, for example, inorganic pigments such as iron oxide, titanium oxide, and Prussian blue; organic dyes such as an alizarin dye, azo dye, and metal phthalocyanine dye; and the like.

The spreader includes, for example, silicone-based surfactants, cellulose powders, dextrin, modified starch, a polyaminocarboxylic acid chelate compound, crosslinked poly(vinylpyrrolidone), a copolymer of maleic acid with a styrene compound, a (meth)acrylic acid copolymer, a half ester of a polymer composed of polyhydric alcohol with dicarboxylic anhydride, a water-soluble salt of polystyrenesulfonic acid and the like.

The sticker includes, for example, paraffin, terpene, a polyamide resin, polyacrylate, polyoxyethylene, wax, polyvinyl alkyl ether, an alkylphenol-formalin condensate product, a synthetic resin emulsion and the like.

The antifreezing agent includes, for example, polyhydric alcohols such as ethylene glycol, diethylene glycol, propylene glycol, glycerol and the like, and so on.

The anticaking agent includes, for example, polysaccharides such as starch, alginic acid, mannose, galactose and the like; poly(vinylpyrrolidone), fumed silica (white carbon), ester gum, a petroleum resin and the like.

The disintegrator includes, for example, sodium tripolyphosphate, sodium hexametaphosphate, metal stearates, a cellulose powder, dextrin, a methacrylate copolymer, poly(vinylpyrrolidone), a polyaminocarboxylic acid chelate compound, a sulfonated styrene-isobutylene-maleic anhydride copolymer, a starch-polyacrylonitrile graft copolymer and the like.

The stabilizer includes, for example, desiccants such as zeolite, calcined lime, magnesium oxide and the like; antioxidants such as phenol compounds, amine compounds, sulfur compounds, phosphoric acid compounds and the like; ultraviolet absorbers such as salicylic acid compounds, benzophenone compounds and the like; and so on.

The preservative includes, for example, potassium sorbate, 1,2-benzthiazolin-3-one and the like.

The abrasives include carborundum, silica, calcium oxalate, microbeads, nanobeads, nanoparticles and the like.

In a number of cases it is advantageous to add emulsifiers to the formulation. A first preferred group of emulsifiers encompasses non-ionic surfactants such as, for example: products of the addition of 2 to 30 mol ethylene oxide and/or 0 to 5 mol propylene oxide onto linear or branched, saturated or unsaturated C. sub.8-22 fatty alcohols, onto C. sub.12-22 fatty acids and onto alkyl phenols containing 8 to 15 carbon atoms in the alkyl group; C. sub.12/18 fatty acid monoesters and diesters of addition products of 1 to 30 mol ethylene oxide onto glycerol; glycerol mono- and diesters and sorbitan mono- and diesters of saturated and unsaturated fatty acids containing 6 to 22 carbon atoms and ethylene oxide addition products thereof; addition products of 15 to 60 mol ethylene oxide onto castor oil and/or hydrogenated castor oil; polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable; addition products of 2 to 15 mol ethylene oxide onto castor oil and/or hydrogenated castor oil and/or other vegetable oils; partial esters based on linear, branched, unsaturated or saturated C. sub.6/22 fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose); mono-, di and trialkyl phosphates and mono-, di- and/or tri-PEG-alkyl phosphates and salts thereof; wool wax alcohols; polysiloxane/polyalkyl polyether copolymers and corresponding derivatives; mixed esters of pentaerythritol, fatty acids, citric acid and fatty alcohol and/or mixed esters of C. sub.6-22 fatty acids, methyl glucose and polyols, preferably glycerol or polyglycerol, polyalkylene glycols and alkyl and glycerol carbonates.

The formulation may be prepared as a mixture with components other than those listed above, such as, for example, another herbicide, a plant growth regulator, a fertilizer and the like. It is proposed that these adjuvants would increase the efficacy of the treatment or would have a synergistic effect.

When the aforementioned additional ingredient is contained in the formulation, a content thereof is selected in the range of, on a mass basis, usually 5 to 95% or, preferably, 20 to 90% as a carrier, usually 0.1 to 30% or, preferably, 0.5 to 10% as a surfactant, and 0.1 to 30% or, preferably, 0.5 to 10% as other additional ingredients.

The formulation can be employed as prepared in any desired formulations including liquid formulations, emulsifiable concentrates, wettable powders, dust formulations, oil solutions, water dispersible granules, flowable, emulsion waters, granules, jumbo formulations, suspended-emulsions, microcapsules and others.

FIG. 1 shows a DPC targeting construct for photobleaching-based death in multiple species in accordance with an embodiment of the technology. Ath=*Arabidopsis thaliana*, Nto=*Nicotiana* tobacum, Bra=*Brassica napus*, Zma=*Zea mays*, Mtr=*Medicago truncatula.*

Figure 2:
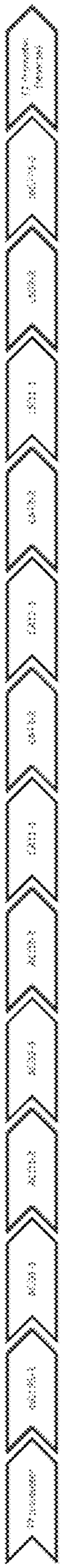
FIG. 2 shows an apoptosis targeting construct for *Brassica rapa* in accordance with an embodiment of the technology. Inserted into vector for *E. coli* production or transcribed in vitro. Resultant dsRNA is applied to plants.

FIG. 2 shows an apoptosis targeting construct for *Brassica rapa* in accordance with an embodiment of the technology. Inserted into vector for *E. coli* production or transcribed in vitro. Resultant dsRNA is applied to plants.

Figure 3:
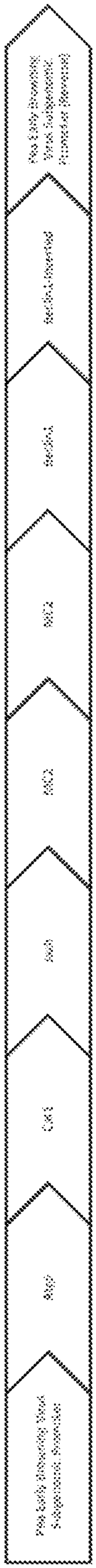
FIG. 3 shows an apoptosis targeting construct 2, for *Nicotiana sylvestris* in accordance with an embodiment of the technology. sgP=subgenomic promoter. Cloned into RNA2-MCS vectors or co-expressed with TRV replicase.

FIG. 3 shows an apoptosis targeting construct 2, for *N. sylvestris* in accordance with an embodiment of the technology. sgP=subgenomic promoter. Cloned into RNA2-MCS vectors or co-expressed with TRV replicase.

Figure 4:
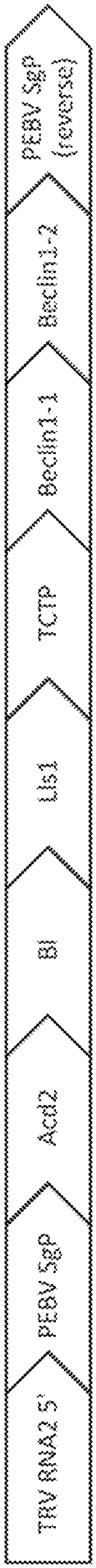
FIG. 4 shows an apoptosis targeting construct 3, for *Nicotiana sylvestris* inside TRV RNA2 in accordance with an embodiment of the technology. RNA applied to plants along with TRV RNA1.

FIG. 4 shows an apoptosis targeting construct 3, for *N. sylvestris* inside TRV RNA2 in accordance with an embodiment of the technology. RNA applied to plants along with TRV RNA1.

Figure 5:
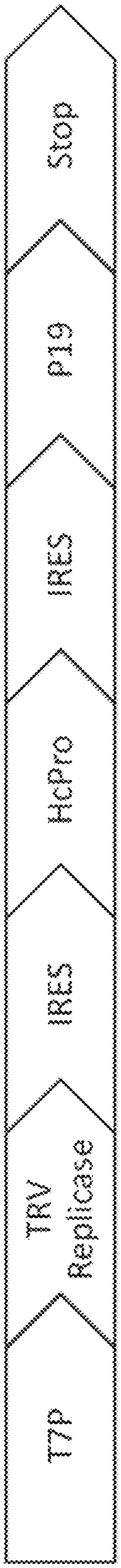
FIG. 5 shows a T7-driven helper construct in accordance with an embodiment of the technology. RNA is added directly to plants, or cloned into RNA2-MCS or RNA1-MCS vectors.

FIG. 5 shows a T7-driven helper construct in accordance with an embodiment of the technology. RNA added directly to plants, or cloned into RNA2-MCS or RNA1-MCS vectors.

Figure 6:
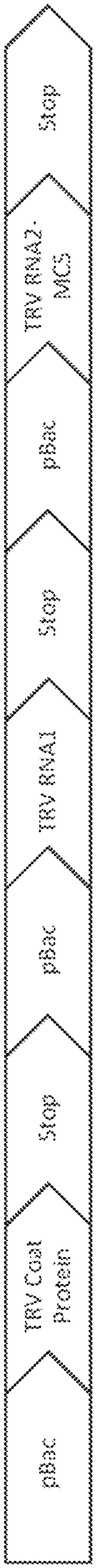
FIG. 6 shows an empty VIGS-based vector to produce coated RNA1 and 2 based RNAi inducers in *E. coli* in accordance with an embodiment of the technology. Targeting constructs such as FIG. 3 are cloned into the MCS contained in RNA2, usually with flanking subgenomic promoters.

FIG. 6 shows an empty VIGS-based vector to produce coated RNAI and 2 based RNAi inducers in *E. coli* in accordance with an embodiment of the technology. Targeting constructs such as FIG. 3 are cloned into the MCS contained in RNA2, usually with flanking subgenomic promoters.

Figure 7:
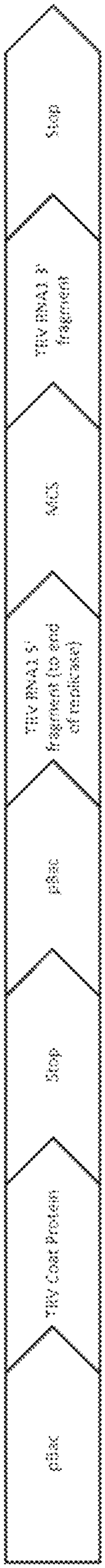
FIG. 7 shows an empty VIGS-based vector to produce coated RNAI and 2 based RNAi inducers in accordance with an embodiment of the technology. Targeting constructs such as FIG. 3 are cloned into the MCS contained in RNA2, usually with flanking subgenomic promoters.

FIG. 7 shows an empty VIGS-based vector to produce coated RNAI and 2 based RNAi inducers in accordance with an embodiment of the technology. Targeting constructs such as FIG. 3 are cloned into the MCS contained in RNA2, usually with flanking subgenomic promoters.

Figure 8:
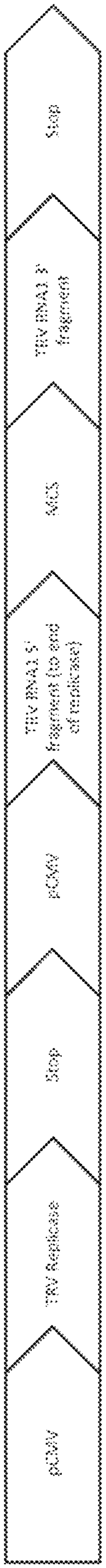
FIG. 8 shows an empty VIGS-based vector to produce coated RNAI and 2 based RNAi inducers in yeast in accordance with an embodiment of the technology. Targeting construct is cloned into the MCS contained in RNA2, usually with flanking subgenomic promoters.

FIG. 8 shows an empty VIGS-based vector to produce coated RNAI and 2 based RNAi inducers in yeast in accordance with an embodiment of the technology. A targeting construct is cloned into the MCS contained in RNA2, usually with flanking subgenomic promoters.

Figure 9:
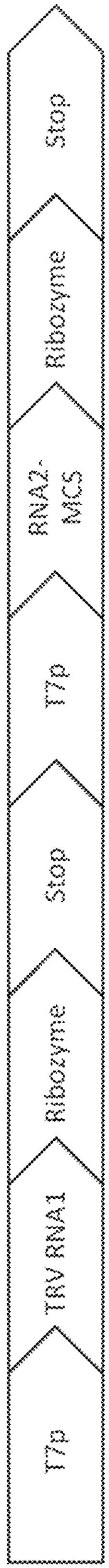
FIG. 9 shows an empty VIGS-based vector to produce naked TRV RNAI and RNA2 based RNAi inducers in accordance with an embodiment of the technology. Functional in *E. coli* with T7 Polymerase and for in vitro production. Ribozymes cleave the RNA into separate strands.

FIG. 9 shows an empty VIGS-based vector to produce naked TRV RNAI and RNA2 based RNAi inducers in accordance with an embodiment of the technology. Functional in *E. coli* with T7 Polymerase and for in vitro production. Ribozymes cleave the RNA into separate strands.

Figure 10:
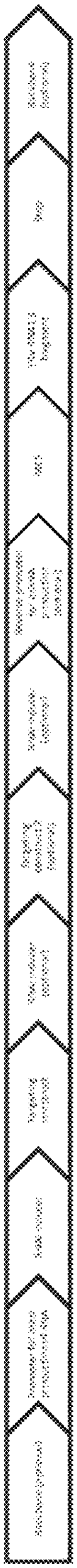
FIG. 10 shows a generic model of a DNA construct for an RNAi herbicide. The core of the herbicide is the targeting construct, tuned to affect one or a few plant species. RNAi inducer elements are either inserted into the targeting sequence (introns to make hairpins, direct or inverted repeats with/without base pairing mismatches), or are inserted around the targeting construct (subgenomic, viral, or endogenous RdRP promoters). This is all driven by either single or flanking promoters for RNA production in the chosen production species, and a circular or linear backbone for maintaining the construct in the production species.
Figure 11:
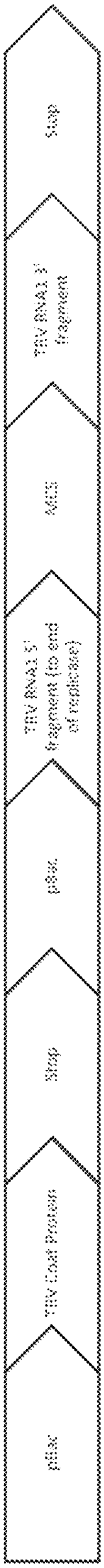
FIG. 11 shows a construct for producing an RNAi herbicide in *E. coli*, without a target construct. In bacteria the TRV coat protein is transcribed and translated. Targeting constructs are inserted into the MCS. The TRV RNAI fragments facilitate coating of the RNA. In target plants this RNA is transcribed to produce viral replicase, which produces dsRNA from the entire RNA. This induces the RNAi response.

FIG. 10 shows a generic model of a DNA construct for an RNAi herbicide. The core of the herbicide is the targeting construct, tuned to affect one or a few plant species. RNAi inducer elements are either inserted into the targeting sequence (introns to make hairpins, direct or inverted repeats with/without base pairing mismatches), or are inserted around the targeting construct (subgenomic, viral, or endogenous RdRP promoters). This is all driven by either single or flanking promoters for RNA production in the chosen production species, and a circular or linear backbone for maintaining the construct in the production species. FIG. 11 shows a construct for producing an RNAi herbicide in *E. coli*, without a target construct. In bacteria the TRV coat protein is transcribed and translated. Targeting constructs are inserted into the MCS. The TRV RNAI fragments facilitate coating of the RNA. In target plants this RNA is transcribed to produce viral replicase, which produces dsRNA from the entire RNA. This induces the RNAi response.

Treatment: By way of example, suitable exemplary treatments are outlined as follows:

Example 1

SEQ ID NO: 3 will be used to treat *Medicago truncatula* seeds by imbibition. This sequence targets the gene for the CHLI subunit of magnesium chelatase (SULFUR gene). Seeds will be imbibed in a solution containing SEQ ID NO: 3 and siRNA targeting AG06. The results will show that the seedlings, and more specifically, the cotyledons will be chlorotic in comparison to the controls.

Example 2

SEQ ID NO: 1 will be used to treat *Arabidopsis thaliana* plants, by abrading the leaves and delivering a solution of SEQ ID NO: 1, a surfactant, and siRNA targeting AG06. This sequence targets the Actin 2 gene. The results will show that the leaves senesce more rapidly than those of the controls.

Example 3

SEQ ID NO: 1 will be used to treat *Arabidopsis thaliana* plants, by abrading the leaves and applying a solution of SEQ ID NO: 1 and a surfactant. This sequence targets the Actin 2 gene. The results will show that the leaves senesce more rapidly than those of the controls.

Example 4

SEQ ID NO: 2 will be used to treat *Arabidopsis thaliana* plants, by spraying the leaves with a solution of SEQ ID NO: 2, an abrasive and a surfactant. This sequence targets the Actin 2 gene. The results will show that the leaves senesce more rapidly than those of the controls.

Example 5

SEQ ID NO: 4 will be used to treat *Medicago truncatula* plants, by injecting the stem or petiole with a solution of SEQ ID NO: 2,2,4-Dichlorophenoxyacetic acid (2,4-D) DMSO and siRNA targeting AG06. SEQ ID NO: 4 targets the gene for the CHLI subunit of magnesium chelatase. The results will show that the leaves become chlorotic more rapidly and to a greater extent than those of the controls. Similarly, the leaves will become chlorotic more rapidly and to a greater extent than those treated with the formulation of Example 1. Without being bound to theory, it is expected that there is a synergistic effect caused by the combination of the siRNA and the 2,4-D.

Example 6

SEQ ID NO: 2 will be used to treat *Physcomitrella patens*, by spraying the moss with a solution of SEQ ID NO: 2 and a surfactant. SEQ ID NO: 4 targets the Actin 2 gene. The results will show that the moss senesces more rapidly than those of the controls.

Example 7

SEQ ID NO: 5 will be used to treat *Medicago truncatula* plants by irrigating the roots with a solution of SEQ ID NO: 5. SEQ ID NO: 5 targets the 18S ribosomal RNA gene. The results will show that the plants senesce more rapidly than the controls.

Example 8

SEQ ID NO: 8 will be used to treat *Arabidopsis thaliana* seeds by coating the seeds prior to imbibition. The formulation will include a sticker such as a terpene or wax or a tackifier such as xanthan gum. SEQ ID NO: 8 targets the 18S ribosomal RNA gene. The results will show that the seedlings senesce, whereas the controls do not.

Example 9

Other sequences will be synthesized and tested. The following functions and genes will be targeted:

Regulating water content (Lock stomata open or closed)

Targets: Effectors that open stomata, Regulators of effectors that open/close stomata.

Gene: ABI1 (AT4G26080) (component of negative feedback loop in abscisic acid (ABA) signalling).

Result: Without being bound to theory, stomata stay closed contributing to the overall damage to the plant and forcing it to retain water.

Example 10: Deregulate Starch Breakdown

Targets: Starch synthesis genes and Repressors of starch breakdown genes (repressors of amylases).

Gene: ADP-glucose pyrophosphorylase (At5g48300).

Result: Without being bound to theory, increased concentration of simple sugars which will affect the energy state of the plant, alter the direction and volume of phloem transport, and make it more accessible to saprotrophs and other organisms.

Example 11

Gene targets that will limit the effectiveness of the RNAi cascade.

Targets: DCLs, AGOs, other RISC components etc.

Gene: AG06 (AT2G32940)

Result: Without being bound to theory, a subset of sRNA processing is ablated altering regulation across the plant and increasing the relative number of available intracellular RISC components.

Example 12

Limit ability of plasmodesmata to close (lock them open via an effector or an element from a component of the blue light response pathway).

Targets: Effectors that close plasmodesmata, or repressors of effectors that open plasmodesmata Gene: Cadmium-ion induced glycine rich protein cdiGRP homologues, an effector that closes plasmodesmata.

Result: Without being bound to theory, plasmodesmata will tend to be open thus maximizing the ability of the RNAi cascade to spread through the plant.

Example 13: Deregulate Cell Wall Modifying Enzymes

Targets: Repressors of cell wall modifying enzymes—specifically enzymes that break down main, load bearing and protective components of the cell wall (expansins, cellulases, proteases, glycoside hydrolases etc.). Gene: DREB binding factor homologues: an effector that negatively regulates leaf elongation.

Result: Without being bound to theory, in addition to contributing to the overall damage (lethality) to the plant, this will also make the plant matter easier to degrade by saprotrophs and other organisms.

Example 15

SEQ ID No. 13 is cloned into SEQ ID No. 28. DNA is grown in *E. coli* and then purified. *Arabidopsis thaliana, Brassica rapa, Medicago truncatula, Zea mays*, and *Nicotiana* leaves are treated with the resultant DNA. In all plants the result will be death through loss of chlorophyll production and chlorophyll degradation (photobleaching).

Example 16

SEQ ID No. 14 is cloned in between T7 promoters in a standard vector. DNA is grown in *E. coli* expressing T7 polymerase or transcribed in vitro. The resulting dsRNA is purified and applied directly to *Brassica rapa* subsp. *pekinensis*. Treated plants will undergo systemically spreading hypersensitive-response like cell death.

Example 17

SEQ ID No. 15 DNA is cloned into the MCS of the T7-RNA2-MCS inducer as shown in sequence ID No 26. The resultant DNA along with the T7-RNA1 inducer are transcribed in vitro. The resulting naked RNAs are applied directly to *Nicotiana sylvestris*. Viral replicase increases the amount of RNAi inducer and targeting construct present. Viral coat proteins and movement proteins initiate the systemic spread of the targeting construct before the RNAi response begins. Treated plants die from necrotic/HR-like lesions.

Example 18

T7 promoter driven RNA2 containing Seq ID NO 15 flanked by sgPs and T7 promoter driven RNAI are prepared and used on *Nicotiana sylvestris* as above. The subgenomic promoter sequences flanking the targeting construct cause it to be replicated by itself, further increasing the amount of targeting construct present before the RNAi response.

Example 19

A targeting construct flanked with sgPs is cloned into the MCS in FIG. 7. The resulting DNA is then cloned into a standard vector and grown in *E. coli*. Transcription results in production of coat protein mRNA and RNAI containing a targeting construct. Translation of the coat protein in *E. coli* results in monomers that recognise elements of the TRV RNAI sequences, coating the entire RNA. This adds stability and increases ease of transmission to target plants. Once inside the target plant, replicase is produced from the TRV RNAI fragment, replicating the entire fragment as well as producing dsRNA of the targeting construct.

Example 20

SEQ ID No. 13 is flanked by subgenomic promoters and cloned into the TRV1 RNAI fragment MCS of an RNAi inducer construct. Treatment of the above plants with the RNA produced will result in photobleaching of chloroplasts and resultant plant death through energy starvation.

Example 21

SEQ ID No. 14 is cloned in original and inverted orientation into an RNAi GG vector. This results in a hairpin with the two sequences separated by an intron. Treatment of plants with this DNA vector produces the hairpin RNA which is processed into siRNAs targeting the 5 endogenous genes. Treated plants die from spreading necrotic lesions as runaway apoptosis is initiated.

Example 22

SEQ ID No. 15 was cloned into the MCS of SEQ ID 18. The resulting DNA is delivered directly to plants along with a helper construct encoding a replicase (SEQ ID No. 17) Endogenous promoters transcribe the initial RNA, replicase is translated, and the construct RNA is replicated. Treated *Nicotiana sylvestris* die from runaway HR-associated apoptotic cell death.

Example 23

SEQ ID No. 16 was cloned into the MCS of SEQ ID 18. The resulting DNA is delivered directly to plants along with a helper construct encoding a replicase (SEQ ID No. 17) Endogenous promoters transcribe the initial RNA, replicase is translated, and the construct RNA is replicated. Treated *Nicotiana sylvestris* die from runaway HR-associated apoptotic cell death.

Example 24

SEQ ID No. 17 is a helper construct. Plants are treated with this helper construct DNA (linear or in a vector) in addition to a RNA2-MCS RNAi inducer containing a targeting construct (SEQ ID No. 13). Treated plants undergo photobleaching and death through energy starvation. SEQ id 17 contains elements such as replicase to produce dsRNA in plant cells.

Example 25

SEQ ID No. 18 is used to clone targeting construct (SEQ ID No. 16) directly. The resulting DNA is delivered directly to plants along with a helper construct encoding a replicase (SEQ ID No. 17) Endogenous promoters transcribe the initial RNA, replicase is translated, and the construct RNA is replicated. Treated *Nicotiana sylvestris* die from runaway HR-associated apoptotic cell death.

Example 26

SEQ ID No. 19 and SEQ ID No. 23 are transcribed in vitro (this DNA is used to produce TRV RNAI RNA in *E. coli* or in vitro). The resulting RNAs are delivered directly to plants with carborundum abrasive. Treated plants die from runaway HR like apoptotic cell death.

Example 27

SEQ ID No. 20 is co-transformed into *E. coli* containing inducible T7 polymerase along with a plasmid containing a targeting construct flanked with RNAI or 2 3' and 5' sequences and driven by T7 promoter (SEQ ID No. 21 containing SEQ ID No. 16 in the MCS). Upon induction the coat protein is translated and coats the two RNAs when they are transcribed. The resulting coated RNAs are delivered directly to plants. Treated plants exhibit a runaway HR-like apoptotic cell death phenotype.

Example 28

SEQ ID 16 is cloned into the MCS of SEQ ID No. 21. The product thereof is co-transformed into *E. coli* containing inducible T7 polymerase along with SEQ ID No. 20. Upon induction the coat protein is translated and coats the two RNAs when they are transcribed. The resulting coated RNAs are delivered directly to plants. Treated plants exhibit a runaway HR-like apoptotic cell death phenotype.

Example 29

SEQ ID No. 22 and SEQ ID 20 are transcribed in vitro using the T7 polymerase system. Coat protein from SEQ ID No. 20 isn't produced. The two RNAs that are produced are applied directly to *N. sylvestris*. Treated plants die from runaway HR like necrotic cell death.

Example 30

SEQ ID No. 23 and SEQ ID No. 20 are transcribed in vitro. Coat protein is not produced in vitro. Plants treated with the two RNAs die from runaway HR like necrotic cell death. The addition of the subgenomic promoter increases the amount of RNA produced in plant cells. This strengthens the RNAi signal.

Example 31

SEQ ID No. 15 is cloned into SEQ ID No. 24. The resultant sequence and SEQ ID 20 are transcribed in vitro. Coat protein is not produced in vitro. Plants treated with the two RNAs die from runaway HR like necrotic cell death. The addition of flanking subgenomic promoters results in the production of dsRNA of just the targeting construct region in addition to replication of the entire RNA. This strengthens the RNAi signal.

Example 32

SEQ ID No. 26 along with RNA produced from SEQ ID No. 23 is delivered directly to *N. sylvestris* with carborundum abrasive. Treated plants die from runaway HR like apoptotic cell death.

Example 33

SEQ ID No. 27 is cloned into the MCS of SEQ ID No. 24. The resultant sequence and SEQ ID No. 20 are transcribed in vitro. Coat protein is not produced in vitro. Plants treated with the two RNAs die from runaway HR like necrotic cell death. The addition of flanking subgenomic promoters results in the production of dsRNA of just the targeting construct region in addition to replication of the entire RNA. This strengthens the RNAi signal.

Example 34

SEQ ID No. 15 is cloned into SEQ ID No. 28 using Bsa1 sites. Plants treated with the resultant DNA transcribe a large hairpin RNA from it. This is processed into siRNAs that induce runaway HR like necrotic cell death.

Example 35

SEQ ID No. 29 is used to treat plants. Plants treated with this DNA transcribe a large hairpin RNA from it. This is processed into siRNAs that induce runaway HR like necrotic cell death.

Example 36

SEQ ID No. 30 will be used to drive transcription of RNAi herbicide components in eukaryotic platforms.

Example 37

SEQ ID No. 31 will be used in conjunction with full length TRV derived RNAs or RNA flanked with TRV RNA 3' and 5' ends. The protein produced coats such RNAs, protecting them and increasing the likelihood of them reaching plant tissues.

Example 38

SEQ ID No. 32 will be used in conjunction with full length TRV derived RNAs or RNA flanked with TRV RNA 3' and 5' ends. The protein produced coats such RNAs, protecting them and increasing the likelihood of them reaching plant tissues. Codon optimization has been used to create a sequence for optimal translation in *E. coli.*

Example 39

SEQ ID No. 33 will be used in helper constructs.

The protein produced suppresses RNAi temporarily in planta. This allows initial RNA elements time to replicate and reach a higher concentration before being processed by RNAi machinery.

Example 40

SEQ ID No. 34 will be incorporated in a plant expressible helper construct and DNA or RNA delivered directly to plants. It will lessen and slow the spread of the RNAi cascade.

Example 41

SEQ ID No. 35 will be incorporated into a plant-expressible helper construct and DNA or RNA applied directly to plant. It will aid in the spread of RNAs before RNAi is activated.

Example 42

SEQ ID No. 36 will be used to find homologues in other species. It is also a target gene used to build target constructs. Knockdown of this gene will result in autophagy.

Example 43

SEQ ID No. 37 will be used to find homologues in other species. It is also a target gene used to build target constructs. Knockdown of this gene will cause apoptosis.

Example 44

SEQ ID No. 38 will cause apoptosis. It is a target gene used to build target constructs. It will also be used to find homologues in other species.

Example 45

SEQ ID No. 39 It is a target gene used to build target constructs. It will also be used to find homologues in other species.

Example 46

SEQ ID No. 40 It is a target gene used to build target constructs. It will also be used to find homologues in other species.

Example 47

SEQ ID No. 41 It is a target gene used to build target constructs. It will also be used to find homologues in other species.

Example 48

SEQ ID No. 42 It is a target gene used to build target constructs. It will also be used to find homologues in other species.

Example 49

SEQ ID No. 43 It is a target gene used to build target constructs. It will also be used to find homologues in other species.

Example 50

SEQ ID No. 44 It is a target gene used to build target constructs. It will also be used to find homologues in other species.

Example 51

SEQ ID No. 45 It is a target gene used to build target constructs. It will also be used to find homologues in other species.

Example 52

SEQ ID No. 46 It is a target gene used to build target constructs. It will also be used to find homologues in other species.

Example 53

SEQ ID No. 47 It is a target gene used to build target constructs. It will also be used to find homologues in other species.

Example 54

*Nicotiana sylvestris* was chosen as the target weed. *Medicago truncatula* was chosen as the non-target plant. The sequences for both species are publically available. Genes from the target list that act as negative regulators of apoptosis were selected and the *Nicotiana sylvestris* homologues were run through RNAxs. The most accessible sequence regions were compared to homologous stretches of *Medicago truncatula* genes to confirm divergence. Suitable sequences were incorporated into SEQ ID No. 15. This construct was then cloned into the MCS of SEQ ID No. 21 in an *E. coli* backbone (pUC57). SEQ ID No. 20 was also cloned into the *E. coli* backbone. *E. coli* containing inducible T7 polymerase was transformed with this construct. Transformed *E. coli* were grown up, spun down, lysed, and the lysate rubbed onto plants with carborundum. The lysate contains RNA1 and 2 from TRV, with the targeting construct inside the MCS of RNA2. These RNAs are coated with viral coat protein. Treated plants undergo spreading apoptotic cell death similar to a runaway hypersensitive response. Without being bound to theory, this is because replicase is produced from the TRV RNA1, which replicates both RNAs. This increases RNA concentration. Viral movement proteins aid in the spread of intact RNAs. Eventually the dsRNA replication intermediaries are recognized by RISC machinery and processed into siRNAs. The siRNAs produced from the targeting construct induce the knock-down of Atg5, Cat1, Jazh, MC2, and Beclin1. This tips the plant cell's regulatory machinery toward hypersensitive response. siRNAS produced from the targeting construct, as well as phased siRNAs produced from RdRP replication of target mRNAs by RISC machinery, are transported throughout the plant, spreading the phenotype. Treating *Medicago truncatula* did not affect the plant because processing of the targeting construct does not result in siRNAs targeting endogenous genes.

Example 55

SEQ ID No. 13 is a target construct generated as follows: The CHLI1 gene in *Arabidopsis* was used to find homologues in *Brassica rapa, Medicago truncatula, Zea mays*, and *Nicotiana* tobacum. These sequences were searched for regions accessible by RISC machinery using RNAxs. The best regions from each homologue were incorporated into the target construct. This construct was then cloned into the MCS of SEQ ID No. 21 in an *E. coli* backbone (pUC57). SEQ ID No. 20 was also cloned into the *E. coli* backbone. *E. coli* containing inducible T7 polymerase was transformed with this construct. Transformed *E. coli* were grown up, spun down, lysed, and the lysate rubbed onto plants with carborundum. The lysate contains RNA1 and 2 from TRV, with the target construct inside the MCS of RNA2. These RNAs are coated with viral coat protein. Replicase is produced from the TRV RNA1, which replicates both RNAs. Without being bound to theory, this increases RNA concentration. Viral movement proteins aid in the spread of intact RNAs. Eventually the dsRNA replication intermediaries are recognizes by RISC machinery and processed into siRNAs. The siRNAs produced from the targeting construct induce the knock-down of CHLI1. Plant growth is retarded, sometimes fatally, as damaged photosystems are not repaired. Off target plants are unaffected.

Example 56

A helper construct is constructed from SEQ IDs 33, 34 and 35. Sequences are driven by the T7 promoter producing polycistronic RNA. IRES elements are used to ensure translation in plant tissues. This is inserted into the MCS of SEQ ID No. 18. This along with SEQ ID No. 22 is transcribed in vitro. The resulting RNAs are applied directly to plants. Treated plants exhibit runaway HR-like apoptotic cell death. The 30 kda movement protein and the HCpro proteins aid in the movement of the unprocessed RNAs. The P19 protein suppresses the RNAi response until the RNAs have moved further from the application site.

Example 57

A targeting construct was designed to induce senescence in *Nicotiana sylvestris*. Genes from the senescence gene list were used to identify homologues of APG-9, ATG 2, SRI, and APG7 in *N. sylvestris*. These were run through RNAxs to identify RISC accessible regions. Sequences complementary to the most accessible regions were strung together to make the targeting construct RNA. DNA encoding this RNA is cloned into the MCS of SEQ ID No. 18. This and SEQ ID No. 17 are cloned into a binary vector maintained in plants and *E. coli*. The resulting construct is replicated and purified from *E. coli*, and the DNA applied directly to plants. In the plant the DNA is transcribed. The resultant RNAs are directly replicated after replicase is translated from RNAI. Treated plants undergo spreading senescence which eventually overwhelms them. As senescence takes a while to develop after induction, the signal has time to spread through the plant.

Example 58

A targeting construct was designed to starve cells of amino acids. Genes from the starvation list were used to identify homologues of HDH, AthMee2, and ICDH in *N. sylvestris*. These were run through RNAxs to identify RISC accessible regions. Sequences complementary to the most accessible regions were strung together to make the targeting construct RNA. DNA encoding this RNA is cloned into the MCS of SEQ ID No. 18. This and SEQ ID No. 17 are cloned into a binary vector maintained in plants and *E. coli*. The resulting construct is replicated and purified from *E. coli*, and the DNA delivered directly to plants. In the plant the DNA is transcribed. The resultant RNAs are directly replicated after replicase is translated from RNA1. Processing of these RNAs by RISC machinery leads to loss of production of a number of amino acids. Plants die due to being unable to replace degraded or damaged proteins.

Example 59

SEQ ID No. 48 is a target construct generated as follows: The *Arabidopsis* PDS gene was used to find the homologue in *Nicotiana sylvestris*. These sequences were searched for regions accessible by RISC machinery using RNAxs. The best regions containing no perfect matches to *Medicago truncatula* were incorporated into the target construct. DNA encoding this RNA is cloned into the MCS of SEQ ID 18. This and SEQ ID No. 17 are cloned into a binary vector maintained in plants and *E. coli*. The resulting construct is replicated and purified from *E. coli* and the DNA applied directly to plants. In the plant the DNA is transcribed. The resultant RNAs are directly replicated after replicase is translated from RNA1. Processing of the targeting construct results in siRNAs that knock down Phytoene desaturase. Plants turn white and plant growth is retarded, sometimes fatally, as damaged photosystems are not repaired. Off target plants such as *Medicago truncatula, Arabidopsis thaliana* and *Beta vulgaris* are unaffected.

Example 60

SEQ ID No. 49 is DNA containing TRV RNA2 loaded with the *Nicotiana sylvestris* anti-PDS targeting construct. This, along with SEQ ID No. 19 are used to produce RNAs in Vitro with T7 polymerase. The resulting RNAs are applied directly to plants. The RNAs are directly replicated after replicase is translated from RNA1. Processing of the targeting construct results in siRNAs that knock down Phytoene desaturase. Plants turn white and plant growth is retarded, sometimes fatally, as damaged photosystems are not repaired. Off target plants such as *Medicago truncatula, Arabidopsis thaliana* and *Beta vulgaris* are unaffected.

Example 61

SEQ ID No. 32 is used in conjunction with full length TRV derived RNAs or RNA flanked with TRV RNA 3' and 5' ends. The protein produced coats such RNAs, protecting them and increasing the likelihood of them reaching plant tissues. Codon optimization has been used to create a sequence for optimal translation in *E. coli.*

Example 62

The generalized steps for controlling a weed species are as follows:

Selecting a weed plant species to be controlled;

Sequencing genes from the target list in the weed and in non-target neighbor plants;

Designing a targeting construct complementary to accessible regions of target genes that are divergent in off-target plants;

Incorporating the target construct into an effective RNAi inducer;

Adding helper components as required to increase silencing efficiency and spread;

Producing the DNA or RNA to apply to plants;

Formulating the DNA or RNA for optimum penetration into plant tissues; and

Delivering the formulated DNA or RNA to plants.

Example 63

SEQ ID No. 48 was examined and found to have 0 off-target perfect matches in *Medicago truncatula, Brassica napus, Arabidopsis thaliana, Beta vulgaris, Gossypium* spp. and *Oryza sativa.*

Example 64

An accessory targeting construct was built targeting AB1, ADP-glucose pyrophosphorylase, AG06, cdiGRP, and DREB binding factor homologues in *Nicotiana sylvestris*. These were run through RNAxs to identify RISC accessible regions. Sequences complementary to the most accessible regions were strung together to make the targeting construct RNA. DNA encoding this RNA is cloned into the MCS of SEQ ID No. 19 (T7 RNA1) and applied in conjunction with SEQ ID No. 49: (T7 driven RNA2 with Nsy1 PDS targeting construct in MCS). RNA from these sequences was produced in vitro using the T7 system. Treated plants turn white and plant growth is retarded, sometimes fatally, as damaged photosystems are not repaired. ABI1 knock-down will cause stomata to stay closed contributing to the overall damage to the plant and forcing it to retain water. ADP-glucose pyrophosphorylase knock-down will cause increased concentration of simple sugars which will affect the energy state of the plant, alter the direction and volume of phloem transport, and make it more accessible to saprotrophs and other organisms. AG06 knockdown will ablate a subset of small RNA processing, freeing RISC machinery to process endogenous gene targets. cdiGRP knock-down will keep plasmodesmata open even during conditions of stress, increasing the rate of spread of the RNAi cascade. Knock-down of homologues of DREB binding factor caused unregulated leaf elongation, including increasing production of cell-wall degrading enzymes such as expansins. This contributes to the overall damage of the plant.

Example 65

The process for creating a RNAi herbicide against a specific species is as follows.

1. Obtain sequence data for target species
   a. Publically available,
   b. If no sequence data is available use PCR to amplify regions corresponding to genes in target list. Have those PCR fragments sequenced.
2. Select target regions based on RNA accessibility,
3. Obtain sequence data for other plants in area where herbicide will be applied a. Use public data where available, otherwise PCR and sequence as in 1.

4. Search for target region sequences with no more than 18 nt sequential complementarity to non-target plants.
   a. And preferably less than 18 nt complementarity or none.
5. Assemble 2 or more (usually at least 5) target regions into a targeting construct
6. Add an RNAi inducer to the targeting construct
   a. Replicase/promoter pairs
   b. Secondary structure elements (bulges, single base mismatches outside of core region, hairpins and inverted repeats)
7. Chose the most appropriate RNA production method
   a. In planta
      i. Construct flanked with plant expression promoters (CaMV35 for example) DNA added to plants.
   b. In prokaryotes
      i. Add prokaryotic promoters (one or flanking promoters) to produce single or double stranded RNA.
      ii. Add coating elements from virus (such as TRV) and co-express construct with bacterially translated coat protein.
   c. In other eukaryotes
      i. Same as i for prokaryotes
      ii. Express VIGS based RNAs along with viral replicase
         1. Results in production of coated RNAs containing construct
   d. In vitro Certain elements enhance the systemic spread of RNAi. Mismatched base pairs in the stem region of a dsRNA are a powerful way to ensure the derived siRNAs trigger RdRP activity at their targets. Mismatches at the 5" end of the siRNA are not tolerated. Moving from the 5' to the 3' end, mismatches become better tolerated. Using endogenous miRNA generating sequences such as tasi-RNA as backbones also aids in systemic spread.

Without being bound to theory, there are two reasons why the process described in this patent is generalizable to all known plant species. First, due to the degenerate nature of the genetic code there are many sequence level differences between species in genes that code for identical proteins. Because RNAi requires at least 18 nt of sequence complementarity (usually 21 nt) it is relatively easy to find stretches of RNA that are different in the target species and its neighbors. A single mismatch is usually sufficient to prevent knock-down in off-target plants. Sequences with 2 or more mismatches to off-target plants are sought to ensure knock-down does not occur. Plants can develop resistance to a specific targeting construct through mutation. The likelihood of developing enough spontaneous mutations in all the target genes simultaneously however is low. Even if resistance emerges those individuals can be sequenced and used to produce a new targeting construct.

Secondly, the core RISC machinery is highly conserved and RNAi is critical for defense against virus and pathogenic sequence elements. In order to develop resistance to this process a plant would have to shut down this response. Those plants would be highly susceptible to disease preventing them from gaining a foothold in the population.

List of potential genes of interest for use in this technology:

Essential Gene Targets
- 3-phosphoshikimate 1-carboxyvinyltransferase (EPSP synthase) AT2G45300
- Chalcone synthase (CHS) AT5G13930
- Starch synthase (SSI) AT5G24300
- Starch synthase 3 (SS3) AT1G11720
- Cellulose synthase 1 (CESA1) AT4G32410
- Cellulose synthase 8 (CESA8) AT4G18780
- Histidinol dehydrogenase (HDH) AT5G63890
- Maternal effect embryo arrest 2/Shikimate dehydrogenase (AthMEE2) AT3G06350
- Isocitrate dehydrogenase (ICDH) AT1G54340
- Hydroxyl methylglutaryl coA reductase 1 (HMG1) AT1G76490
- Pyruvate dehydrogenase E1 alpha subunit (PDH-E1 ALPHA) AT1G01090
- Branched chain amino acid transaminase 1 (BCAT1) AT1G10060
- Branched chain amino acid transaminase 2 (BCAT2) AT1G10070
- 18s ribosomal RNA (18S rRNA) 1005246134
- Eukaryotic elongation factor (eEF-IB beta) AT1G30230
- Spliceosome associated protein 130b (SAP130b) AT3G55220
- 2' tRNA phosphotransferase (TRPT) AT2G45330
- Phosphoribosylanthranilate isomerase 1 (PAI1) AT1G07780
- Phytoene desaturase (PDS) AT4G14210
- Dongle (DGL) AT1G05800

Apoptosis Gene Targets
- Beclin 1 (BECLIN1) AT3G61710
- Bax inhibitor 1 (B1-1) JX481914
- Phosphatidylinositol 3-kinase (PI3K/VPS30) AT1G60490
- Lesion simulating disease 1 (LSD1) AT4G20380
- Accelerated cell death 1 (ACD1) AT3G44880
- Autophagy related protein 3 (ATG3) AT5G61500
- Autophagy related protein 7 (ATG7) AT5G45900
- Accelerated cell death 11 (ACD11) AT2G34690
- Catalase 1 (CAT1) HF564631.1
- Accelerated cell death 2/Putative red chlorophyll catabolite reductase (ACD2) EU294213.1
- Translationally controlled tumor protein (NbTCTP) AB780363.1
- Jasmonate ZIM domain protein h (JazH) JQ172766.1
- Lethal leaf spot 1-like (LLS1) AF321984.1
- Metacaspase 2 (MC2) AT4G25110

Senescence and Autophagy
- Target of rapamycin (TOR) AT1G50030
- Autophagy 9 (APG9) AT2G31260
- Autophagy 2 (ATG2) AT3G19190
- Autophagy 5 (ATG5) AT5G17290
- Signal responsive 1 (SRI) AT2G22300
- Autophagy 7 (APG7) AT5G45900
- Senescence associated gene (SAG12) AT5G45890
- Phytoalexin deficient (PAD4) AT3G52430
- Constitutive expression of PR genes 5 (CPR5) AT5G64930
- Homologue of yeast autophagy gene 18 (ATG18) AT1G03380

Helper Elements
- Tobacco mosaic virus 30 kDa movement protein, V01408.1
- *Papaya* Ringspot virus HCpro peptide, JX448373.1
- Tomato bushy stunt virus P19 suppressor, AJ288943.1

Inducers
- pTRV2, AF406991.1
- pRNAi-GG, JQ085427.1
- TRV Ppk20 RNA1, AF314165.1

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiment. For example, other genes may be targeted, such as chloroplast and mitochondrial nuclear encoded genes, trafficking and translocation signal sequences, energy metabolism genes, high level regulatory sequences, regulators of cellulases and cell-wall remodelling enzymes and regulators of apoptosis.

What is claimed is:

1. A RNAi payload construct prepared by a method of designing a species-specific gene construct for RNAi suppression of growth of a target plant species, the method comprising the steps of:

selecting at least two target genes for growth suppression, wherein one of said at least two target genes is Beclin1, Accelerated cell death 2 (Acd2), Accelerated cell death 11 (Acd11), Catalase 1 (Cat1), Lesion stimulating disease 1 (Lsd1), Bax inhibitor 1 (BI-1), Lethal leaf spot 1-like (Lls1), Metacaspase 2 (MC2), said genes being from *Nicotiana sylvestris* or *Nicotiana* tobacum or having at least 95% nucleotide sequence identity to said genes from either one of *Nicotiana sylvestris* or *Nicotiana* tobacum across each one of the at least two target genes;

identifying at least one target site accessible to base pairing in each one of the at least two target genes;

identifying at least one divergent site in each one of the at least one target sites;

designing a nucleotide sequence targeting construct complementary to each one of the at least one divergent sites, the nucleotide sequence targeting construct being at least 21 nucleotides in length and being complementary to the at least one divergent site across at least 21 contiguous nucleotides; and incorporating at least one RNAi inducer to the nucleotide sequence construct, thereby designing a RNAi payload for RNAi suppression of growth of the target plant species.

2. The RNAi payload construct of claim 1, further comprising at least one helper nucleotide sequence in the nucleotide sequence construct wherein the helper nucleotide sequence comprises SEQ ID N0:30 or SEQ ID NO:31 or SEQ ID NO:32 or SEQ ID NO:33 or SEQ ID NO:34 or SEQ ID NO:35 or combinations thereof.

3. The RNAi payload construct of claim 1, wherein the nucleotide sequence of the targeting construct comprises the nucleotide sequence set forth in SEQ ID NO:14, or a nucleotide sequence having at least 95% nucleotide sequence identity thereto across each one of the at least two target genes.

4. The RNAi payload construct of claim 1, wherein the nucleotide sequence of the targeting construct comprises the nucleotide sequence set forth in SEQ ID NO:15, or a nucleotide sequence having at least 95% nucleotide sequence identity thereto across each one of the at least two target genes.

5. The RNAi payload construct of claim 1, wherein the nucleotide sequence of the targeting construct comprises the nucleotide sequence set forth in SEQ ID NO:16, or a nucleotide sequence having at least 95% nucleotide sequence identity thereto across each one of the at least two target genes.

6. The RNAi payload construct of claim 1, wherein the nucleotide sequence of the targeting construct comprises a nucleotide sequence set forth in a combination of SEQ ID NO:41, SEQ ID NO:43, SEQ ID NO:46, and SEQ ID NO:47, or a nucleotide sequence having at least 95% nucleotide sequence identity thereto across each one of the at least two target genes.

7. The RNAi payload construct of claim 1, wherein the nucleotide sequence of the targeting construct comprises a nucleotide sequence set forth in a combination of SEQ ID NO:37, SEQ ID NO:38, SEQ ID NO:39, SEQ ID NO:43 and SEQ ID NO:44, or a nucleotide sequence having at least 95% nucleotide sequence identity thereto across each one of the at least two target genes.

8. The RNAi payload construct of claim 1, wherein the nucleotide sequence of the targeting construct comprises a nucleotide sequence set forth in a combination of SEQ ID NO:38, SEQ ID NO:40, SEQ ID NO:41, SEQ ID NO:42 and SEQ ID NO:45, or a nucleotide sequence having at least 95% nucleotide sequence identity thereto across each one of the at least two target genes.

9. The RNAi payload construct of claim 1, wherein the nucleotide sequence of the targeting construct comprises a nucleotide sequence set forth in a combination of SEQ ID NO:38, SEQ ID NO:56, SEQ ID NO:57, SEQ ID NO:58 and SEQ ID NO:59, or a nucleotide sequence having at least 95% nucleotide sequence identity thereto across each one of the at least two target genes.

10. The RNAi payload construct of claim 1, wherein the nucleotide sequence of the targeting construct comprises a nucleotide sequence set forth in a combination of SEQ ID NO:38, SEQ ID NO:40, SEQ ID NO:42, SEQ ID NO:44 and SEQ ID NO:47, or a nucleotide sequence having at least 95% nucleotide sequence identity thereto across each one of the at least two target genes.

11. The RNAi payload construct of claim 1, wherein the nucleotide sequence of the targeting construct comprises a nucleotide sequence set forth in a combination of SEQ ID NO:38, SEQ ID NO:60, SEQ ID NO:61, SEQ ID NO:46 and SEQ ID NO:42, or a nucleotide sequence having at least 95% nucleotide sequence identity thereto across each one of the at least two target genes.

12. The RNAi payload construct of claim 1, wherein the at least two target genes comprise:

Accelerated cell death 11 (Acd11), Accelerated cell death 2 (Acd2), Catalase 1 (Cat1), Catalase 2 (Cat2), and Lesion stimulating disease 1 (Lsd1);

Autophagy related 5 (Atg5), Catalase 1 (Cat1), Jasmonate ZIM domain protein h (JazH), Metacaspase 2 (MC2) and Beclin1;

Accelerated cell death 2 (Acd2), Bax inhibitor (BI-1), Lethal leaf spot 1-like (Lls1), Translationally controlled tumor protein (NbTCTP) and Beclin1;

Acd2, Cat1, Lsd1 and Acd11;

Beclin1, Phytoalexin deficient 4 (Pad4), Constitutive expression of PR genes 5 (Cpr5), Accelerated cell death 1 (Acd1), and Autophagy gene 18 (Atg18);

Beclin1, BI-1, Lls1, MC2, and Acd11; or

Beclin1, Histidinol dehydrogenase (HDH), Maternal effect embryo arrest 2 (ATHMEE2), and Lsd1;

said genes being from *Nicotiana sylvestris* or *Nicotiana* tobacum or having at least 95% sequence identity to said genes from *Nicotiana sylvestris* or *Nicotiana* tobacum across each one of the at least two target genes.

13. The RNAi payload construct of claim 12, wherein the at least two target genes comprise Acd11, Acd2, Cat1, Cat2 and Lsd1.

14. The RNAi payload construct of claim 12, wherein the at least two target genes comprise Atg5, Cat1, JazH, MC2 and Beclin 1.

15. The RNAi payload construct of claim 12, wherein the at least two target genes comprise Acd2, BI-1, Lls1, NbTCTP and Beclin 1.

16. The RNAi payload construct of claim 12, wherein the at least two target genes comprise Acd2, Cat1, Lsd1 and Acd11.

17. The RNAi payload construct of claim 12, wherein the at least two target genes comprise Beclin1, Pad4, Cpr5, Acd1 and Atg18.

18. The RNAi payload construct of claim 12, wherein the at least two target genes comprise Beclin1, BI-1, Lls1, MC2, and Acd11.

19. The RNAi payload construct of claim 12, wherein the at least two target genes comprise Beclin1, HDH, ATHMEE2, and Lsd1.

20. The RNAi payload construct of claim 1, wherein the nucleotide sequence of the targeting construct comprises the nucleotide sequence of:

any one of SEQ ID NO:14, SEQ ID NO:15 or SEQ ID NO:16;

each one of: SEQ ID NO:41, SEQ ID NO:43, SEQ ID NO:46, and SEQ ID NO:47;
each one of: SEQ ID NO:37, SEQ ID NO:38, SEQ ID NO:39, SEQ ID NO:43 and SEQ ID NO:44;
each one of: SEQ ID NO:38, SEQ ID NO:40, SEQ ID NO:41, SEQ ID NO:42 and SEQ ID NO:45;
each one of: SEQ ID NO:38, SEQ ID NO:56, SEQ ID NO:57, SEQ ID NO:58 and SEQ ID NO:59;
each one of: SEQ ID NO:38, SEQ ID NO:40, SEQ ID NO:42, SEQ ID NO:44 and SEQ ID NO:47; or
each one of: SEQ ID NO:38, SEQ ID NO:60, SEQ ID NO:61, SEQ ID NO:46 and SEQ ID NO:42.

21. The RNAi payload construct of claim 1, wherein said genes have at least 99% nucleotide sequence identity to said genes from *Nicotiana sylvestris* or *Nicotiana* tobacum.

* * * * *